US008071607B2

(12) United States Patent
Coulter et al.

(10) Patent No.: US 8,071,607 B2
(45) Date of Patent: Dec. 6, 2011

(54) MNK1 OR MNK2 INHIBITORS

(75) Inventors: Thomas Stephen Coulter, Wantage (GB); Steven Taylor, Didcot (GB); Stephen Murfin, Didcot (GB); Valery Thammalaksa, Paris (FR); Babette Aicher, Frankfurt am Main (DE); Stefan Jaekel, Darmstadt (DE); Tanja Reuter, Darmstadt (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 529 days.

(21) Appl. No.: 11/722,484

(22) PCT Filed: Dec. 22, 2005

(86) PCT No.: PCT/EP2005/013907
§ 371 (c)(1),
(2), (4) Date: Dec. 19, 2008

(87) PCT Pub. No.: WO2006/066937
PCT Pub. Date: Jun. 29, 2006

(65) Prior Publication Data
US 2009/0163520 A1    Jun. 25, 2009

(30) Foreign Application Priority Data

Dec. 23, 2004  (EP) .................................... 04030674

(51) Int. Cl.
*A01N 43/90* (2006.01)
*A61K 31/519* (2006.01)
(52) U.S. Cl. .................................................. 514/262.1
(58) Field of Classification Search .......................... None
See application file for complete search history.

(56) References Cited

FOREIGN PATENT DOCUMENTS
CH          408945       3/1966
WO    WO2004/037159     5/2004
WO    WO2004/106340    12/2004

OTHER PUBLICATIONS

Wolff et. al., "Burger's Medicinal Chemistry and Drug Discovery," 5th Ed. Part 1, pp. 975-977 (1995).*
http://www.medterms.com/script/main/art.asp?articlekey=12063, last accessed on Aug. 24, 2010.*
Dorwald F. A. Side Reactions in Organic Synthesis, 2005, Wiley: VCH, Weinheim p. IX of Preface.*
Banker, et. al., Modern Pharmaceuticals, p. 596.*
Cheng, et al., "Potential Purine Antagonists, VI.", Journal of Organic Chemistry, American Chemical Society, Easton, US, vol. 21, Nov. 1, 1956, pp. 1240-1256.
Young, et al., "Purine Derivatives as Competitive Inhibitors of Human Erythrocyte Membrane Phosphatidylinositol 4-Kinase", Journal of Medicinal Chemistry, American Chemical Society. Washington, US, vol. 33, No. 8 Aug. 1, 1990, pp. 2073-2080.
Peat, et al., "Novel Pyrazolopyrimidine Derivatives as GSK-3 Inhibitors." Bioorganic & Medicinal Chemistry Letters. May 3, 2004, vol. 14, No. 9, pp. 2121-2125.
Traxler et al., "Use of a Pharmacophore Model for the Design of EGF-R Tyrosine Kinase Inhibitors: 4-(Phenylamino)Pyrazolo3,4-Dpyrimidines", Journal of Medicinal Chemistry, American Chemical Society, Washington, US, vol. 40, No. 22, 1997, pp. 3601-3616.

* cited by examiner

*Primary Examiner* — Jeffrey Murray
(74) *Attorney, Agent, or Firm* — Lando & Anastasi, LLP

(57) ABSTRACT

The present invention relates to the use of pyrazolopyrimidine compounds for the production of pharmaceutical compositions for the prophylaxis and/or treatment of diseases which can be influenced by the inhibition of the kinase activity of Mnk1 and/or Mnk2 (Mnk2a or Mnk2b) and/or variants thereof.

19 Claims, 8 Drawing Sheets

Fig. 1: Structural formulae of compounds of the invention
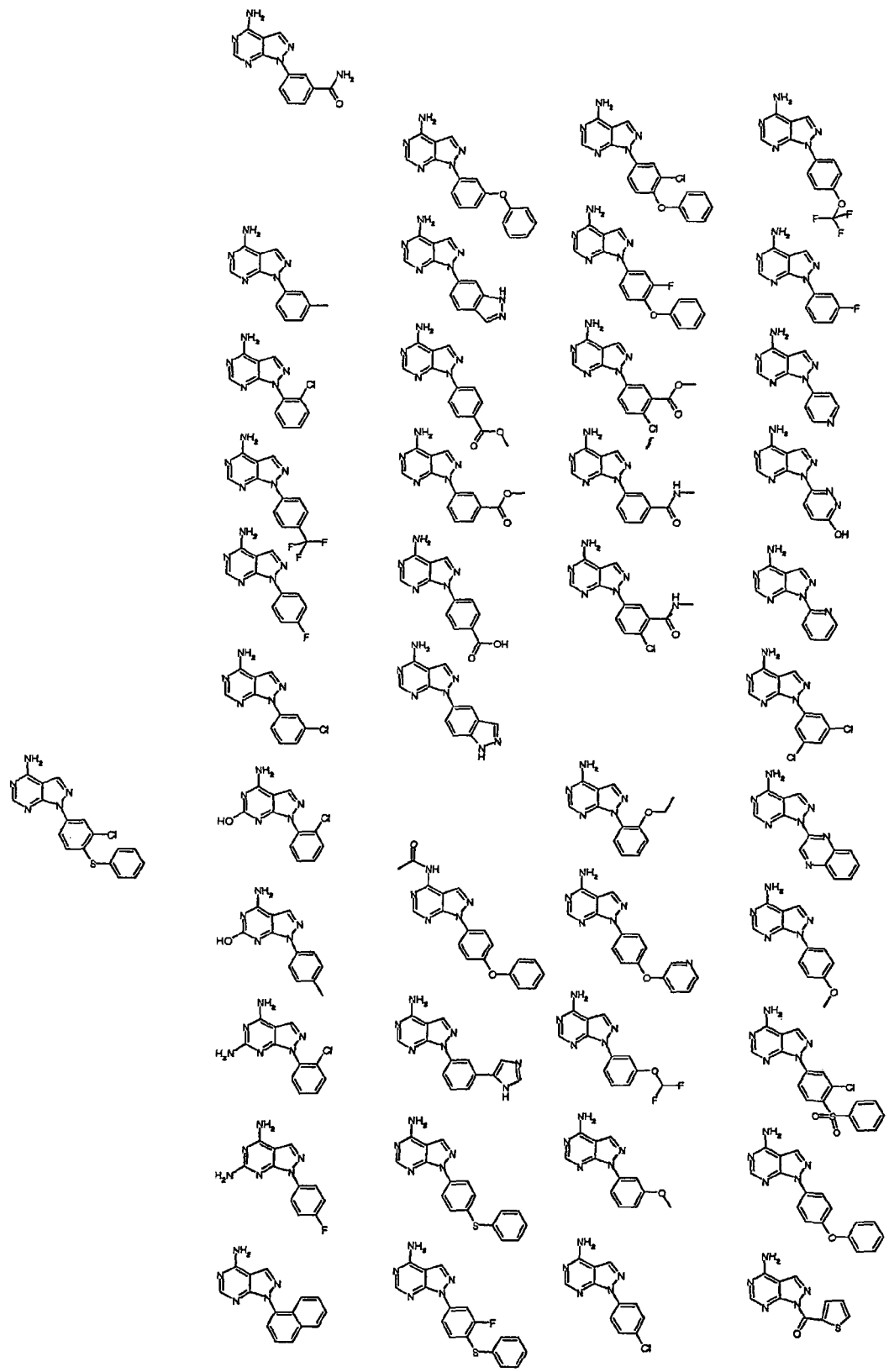

Fig. 1: continued
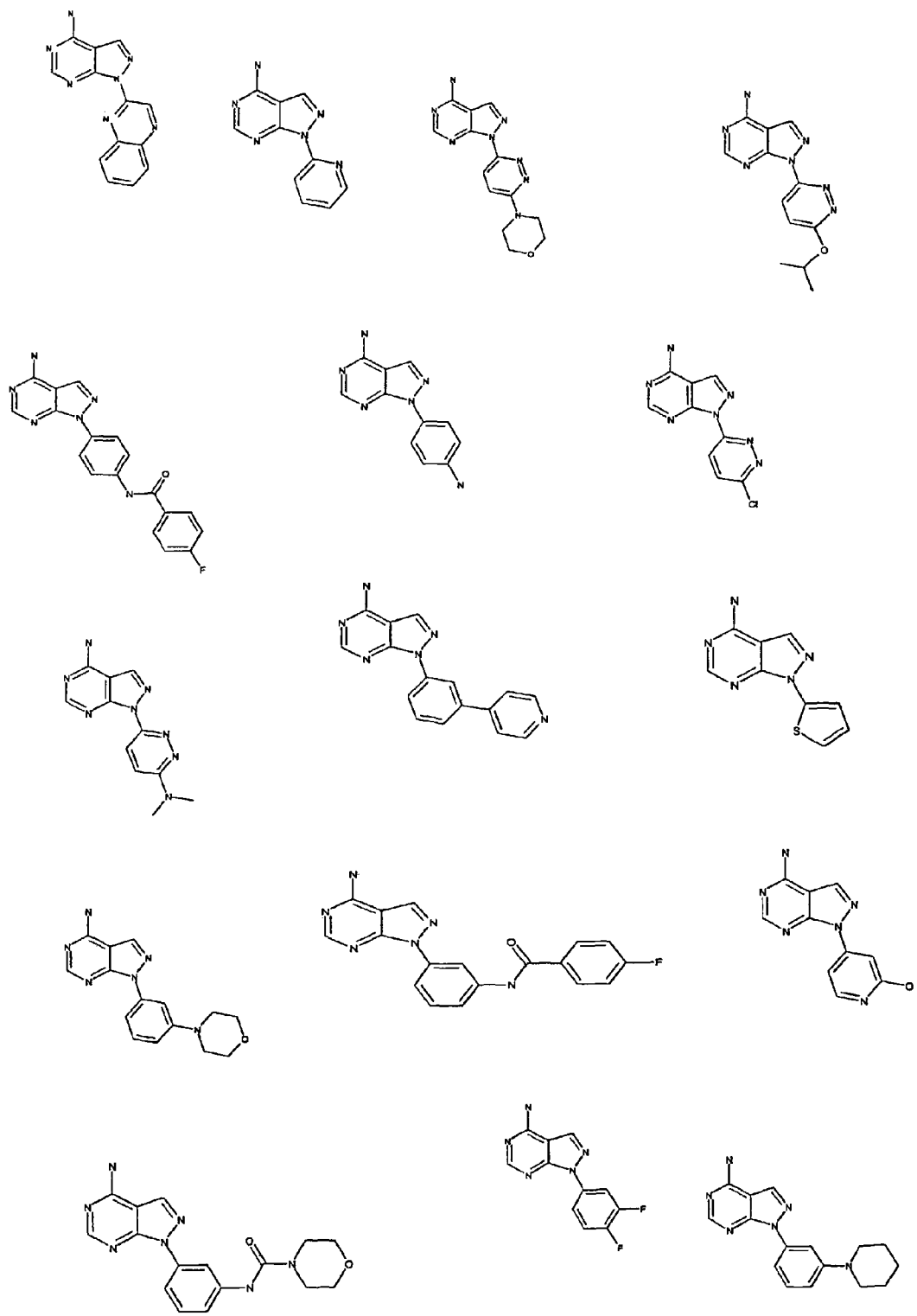

Fig. 1: continued
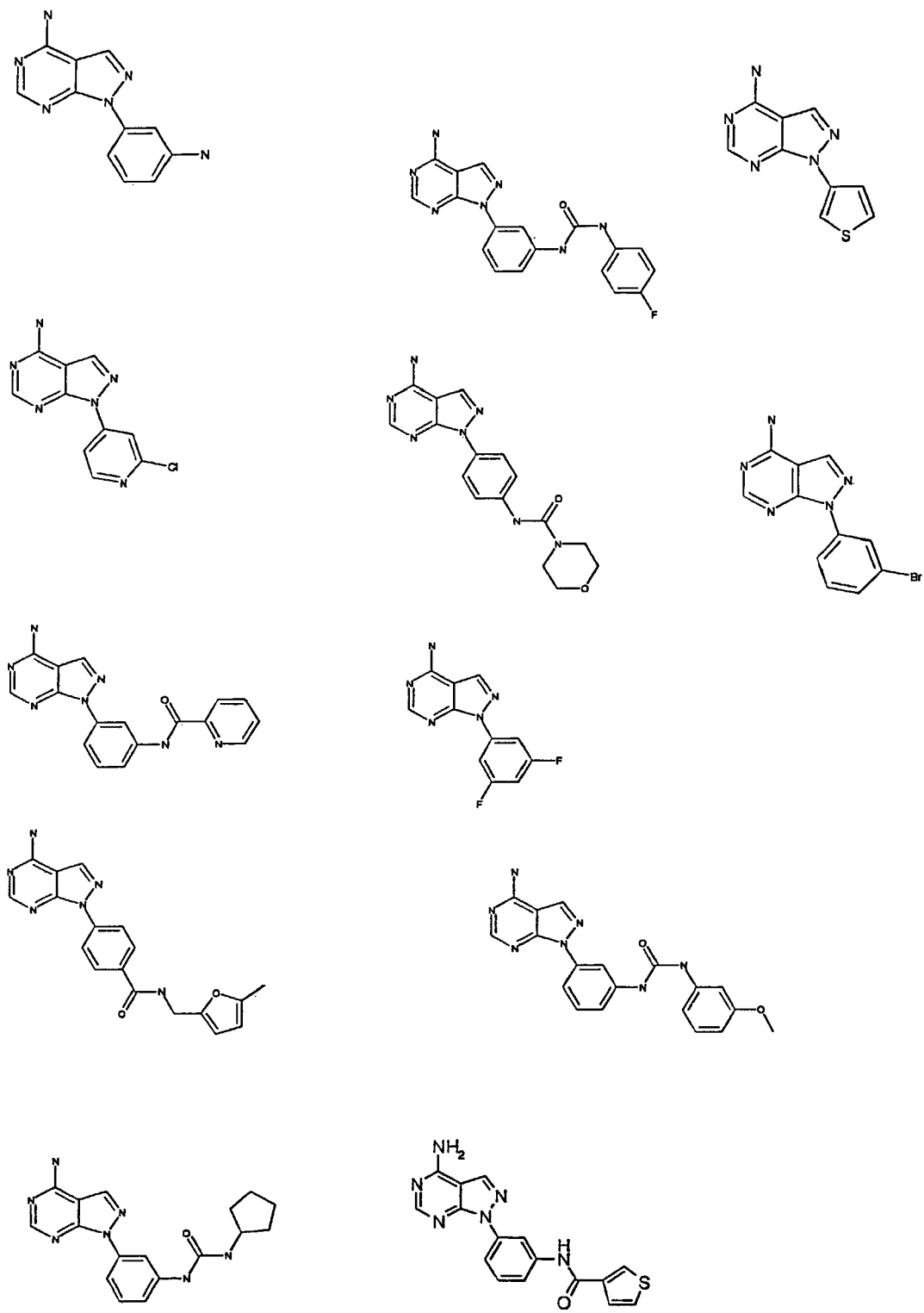

Fig. 1: continued
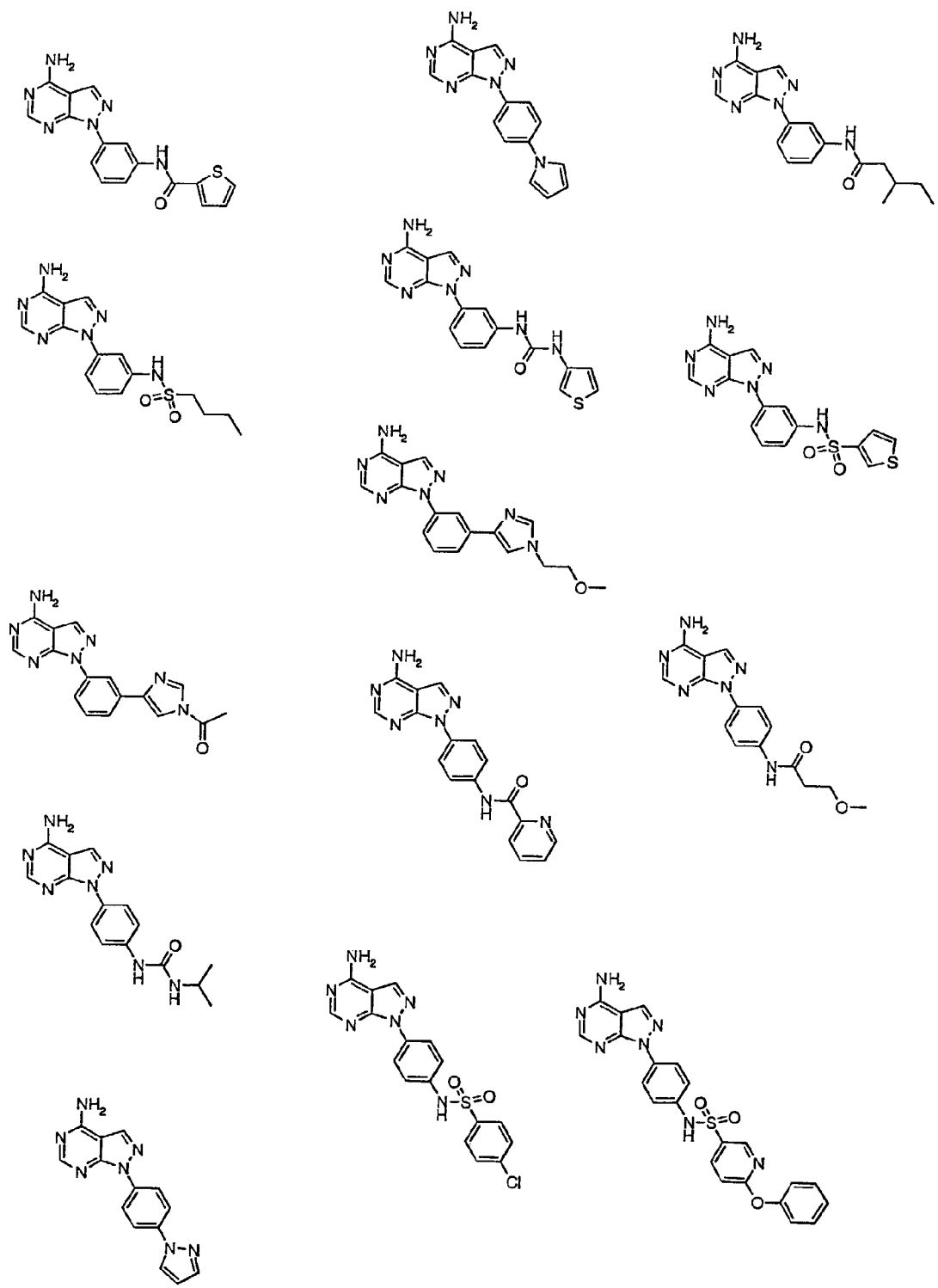

Fig. 1: continued
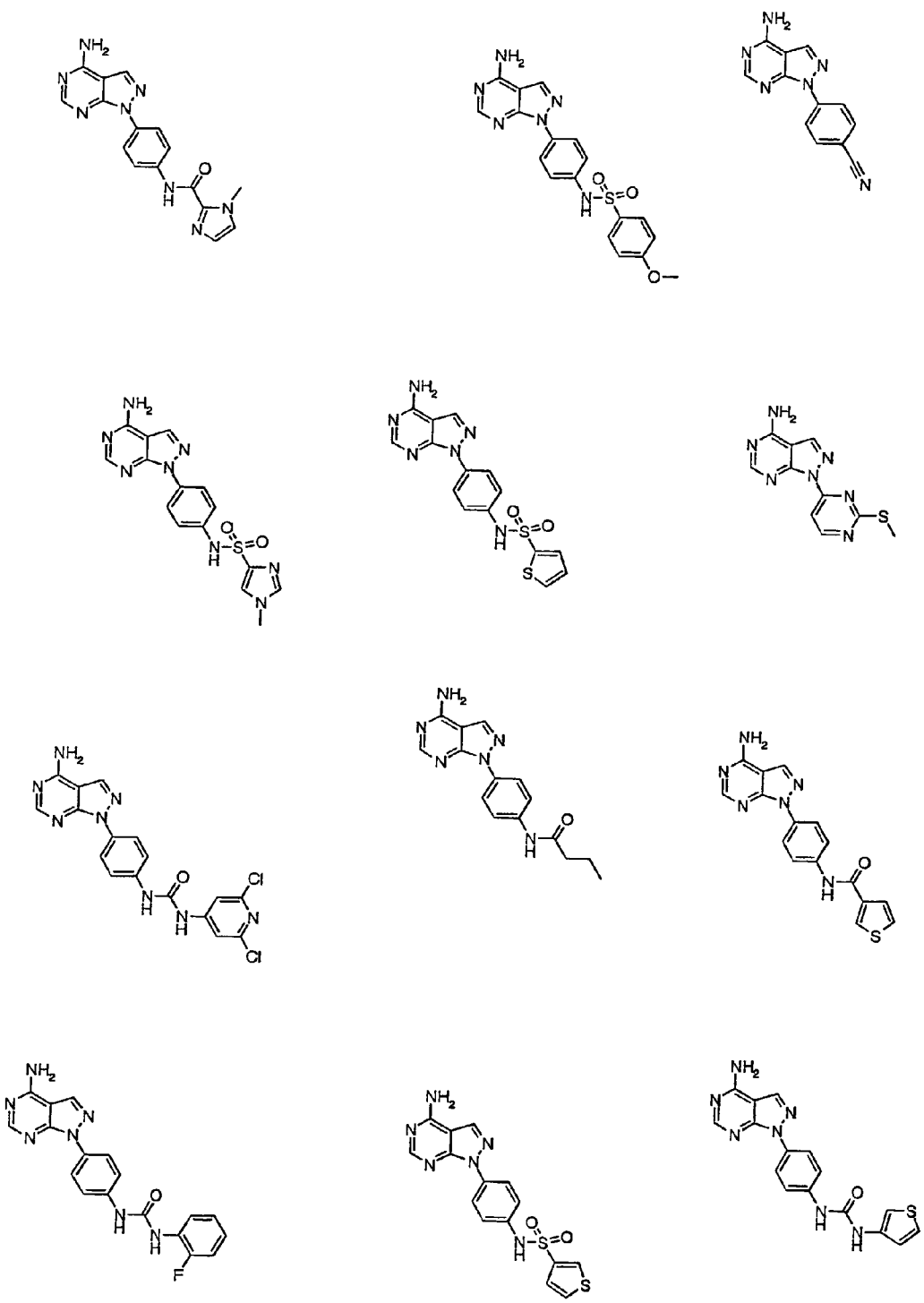

Fig. 1: continued
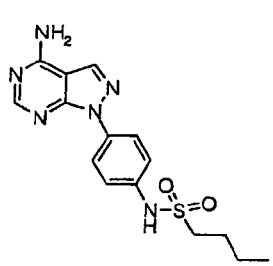 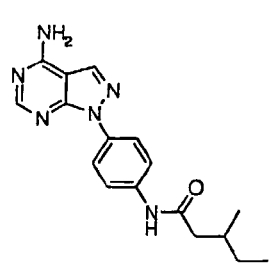 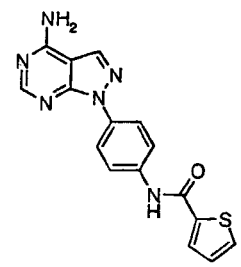
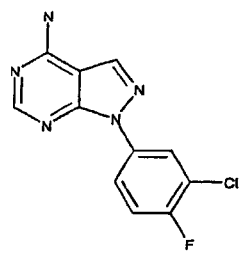 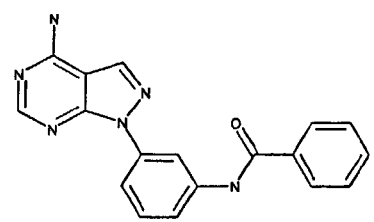
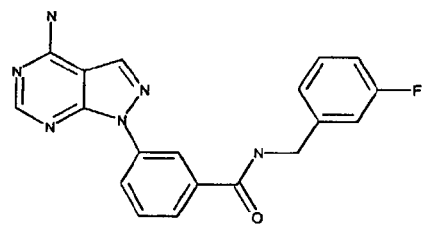 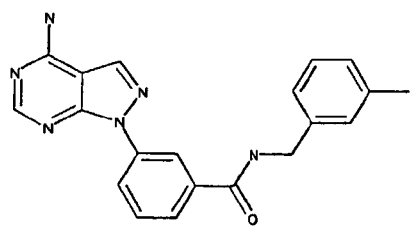
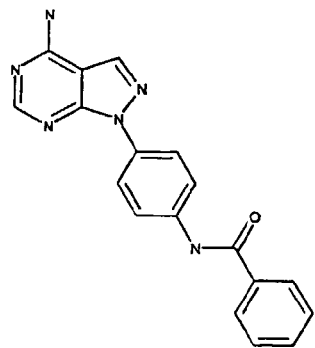 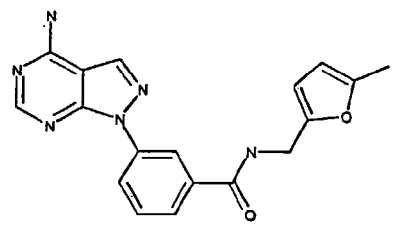

Fig. 1: continued
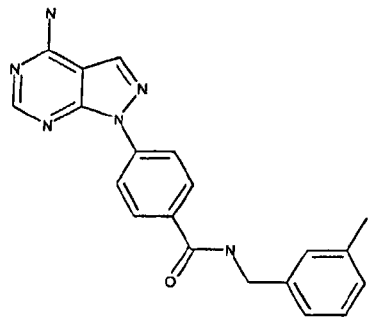
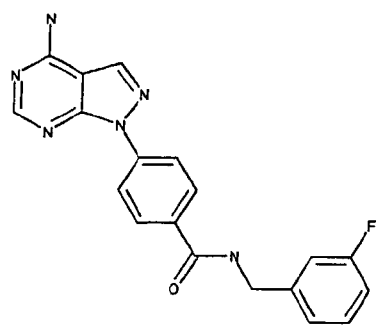
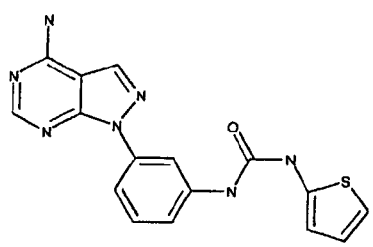
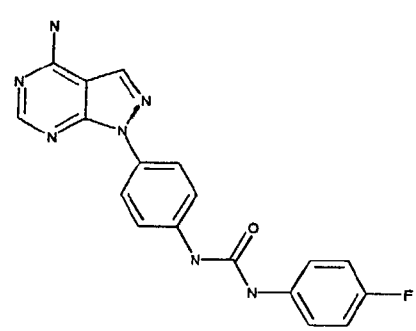
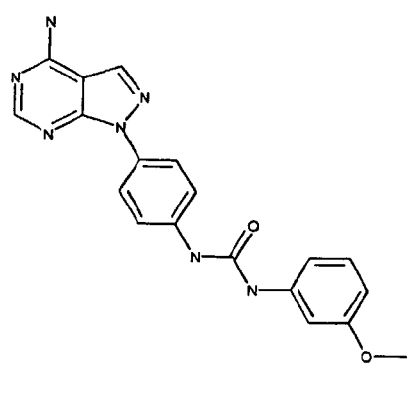
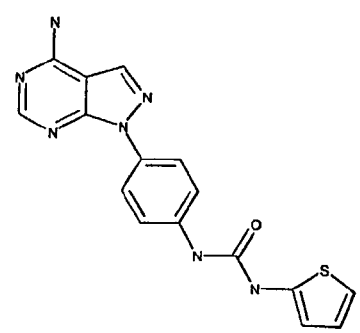
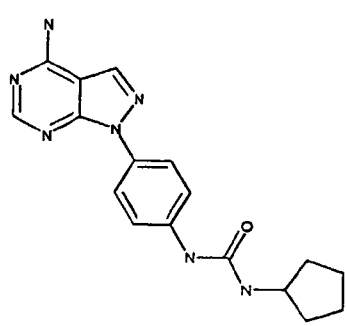
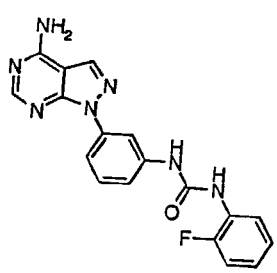

Fig. 1: continued
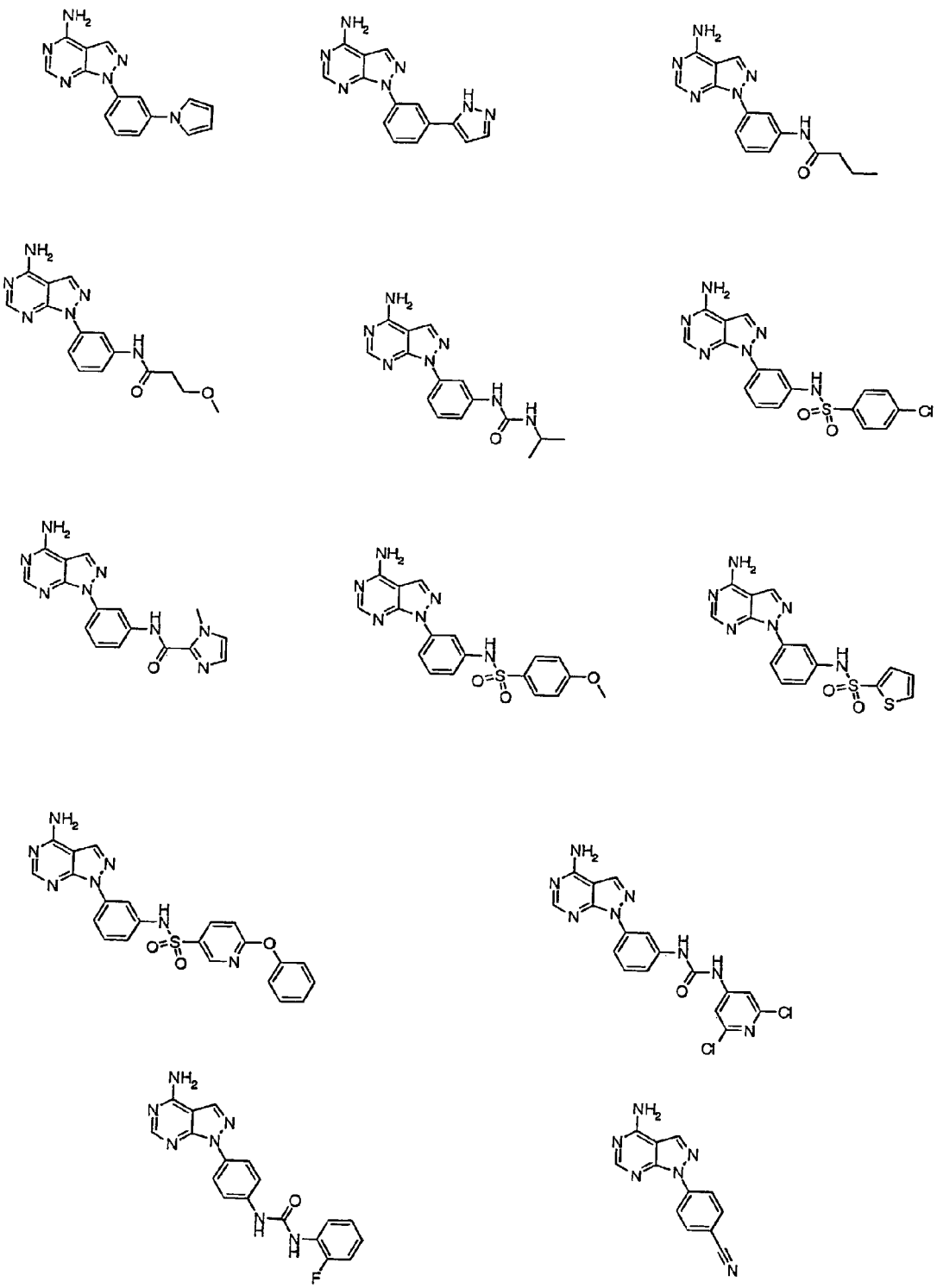

MNK1 OR MNK2 INHIBITORS

CROSS-REFERENCE TO RELATED APPLICATIONS

This application is a US national stage under 35 U.S.C. §371 of PCT/EP2005/013907 filed Dec. 22, 2005, which in turn claims priority to European application number 04030674.8 filed Dec. 23, 2004. These applications are herein incorporated by reference.

The present invention relates to the use of pyrazolopyrimidine compounds for the production of pharmaceutical compositions for the prophylaxis and/or treatment of diseases which can be influenced by the inhibition of the kinase activity of Mnk1 (Mnk1a or MnK1b) and/or Mnk2 (Mnk2a or Mnk2b) or further variants thereof.

Particularly, the present invention relates to the use of pyrazolopyrimidine compounds of the invention for the production of pharmaceutical compositions for the prophylaxis and/or therapy of metabolic diseases, such as diabetes, hyperlipidemia and obesity, hematopoietic disorders and cancer and their consecutive complications and disorders associated therewith.

Metabolic diseases are diseases caused by an abnormal metabolic process and may either be congenital due to an inherited enzyme abnormality or acquired due to a disease of an endocrine organ or failure of a metabolically important organ such as the liver or the pancreas.

The present invention is more particularly directed to the treatment and/or prophylaxis of in particular metabolic diseases of the lipid and carbohydrate metabolism and the consecutive complications and disorders associated therewith.

Lipid disorders cover a group of conditions which cause abnormalities in the level and metabolism of plasma lipids and lipoproteins. Thus, hyperlipidemias are of particular clinical relevance since they constitute an important risk factor for the development of atherosclerosis and subsequent vascular diseases such as coronary heart disease.

Diabetes mellitus is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

In one preferred embodiment of the present invention the compounds and compositions of the present invention are useful for the treatment and/or prophylaxis of metabolic diseases of the carbohydrate metabolism and their consecutive complications and disorders such as impaired glucose tolerance, diabetes (preferably diabetes type II), diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome, diabetic coma with or without ketoacidosis, diabetic hyperosmolar coma, hypoglycemic coma, hyperglycemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic angiopathies, diabetic peripheral angiopathy, diabetic ulcer, diabetic arthropathy, or obesity in diabetes.

In a further preferred embodiment the compounds and compositions of the present invention are useful for the treatment and/or prophylaxis of metabolic diseases of the lipid metabolism (i.e. lipid disorders) and their consecutive complications and disorders such as hypercholesterolemia, familial hypercholesterolemia, Fredrickson's hyperlipoproteinemia, hyperbetalipoproteinemia, hyperlipidemia, low-density-lipoprotein-type [LDL] hyperlipoproteinemia, pure hyperglyceridemia, endogenous hyperglyceridemia, isolated hypercholesterolemia, isolated hypertroglyceridemia, cardiovascular diseases such as hypertension, ischemia, varicose veins, retinal vein occlusion, atherosclerosis, angina pectoris, myocardial infarction, stenocardia, pulmonary hypertension, congestive heart failure, glomerulopaty, tubulointestitial disorders, renal failure, angiostenosis, or cerebrovascular disorders, such as cerebral apoplexy.

In a further preferred embodiment of the present invention the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AMMol), polycythemia vera, lymphoma, acute lymphocytic leukemia (ALL), chronic lymphocytic leukemia (CCL), Wilm's tumor, or Ewing's Sarcoma.

In a further preferred embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, corpus carcinoma, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, esophageal cancer, soft tissue sarcoma, cachexia, or pain.

Protein kinases are important enzymes involved in the regulation of many cellular functions. The LK6-serine/threonine-kinase gene of Drosophila melanogaster was described as a short-lived kinase which can associate with microtubules (J. Cell Sci. 1997, 110(2): 209-219). Genetic analysis in the development of the compound eye of Drosophila suggested a role in the modulation of the RAS signal pathway (Genetics 2000 156(3): 1219-1230). The closest human homologues of Drosophila LK6-kinase are the MAP-kinase interacting kinase 2 (Mnk2, e.g. the variants Mnk2a and Mnk2b) and MAP-kinase interacting kinase 1 (Mnk1) and variants thereof. These kinases are mostly localised in the cytoplasm. Mnks are phosphorylated by the p42 MAP kinases Erk1 and Erk2 and the p38-MAP kinases. This phosphorylation is triggered in a response to growth factors, phorbol esters and oncogenes such as Ras and Mos, and by stress signalling molecules and cytokines. The phosphorylation of Mnk proteins stimulates their kinase activity towards eukaryotic initiation factor 4E (eIF4E) (EMBO J. 16: 1909-1920, 1997; Mol Cell Biol 19, 1871-1880, 1990; Mol Cell Biol 21, 743-754, 2001). Simultaneous disruption of both, the Mnk1 and Mnk2 gene in mice diminishes basal and stimulated eIF4E phosphorylation (Mol Cell Biol 24, 6539-6549, 2004). Phosphorylation of eIF4E results in a regulation of the protein translation (Mol Cell Biol 22: 5500-5511, 2001).

There are different hypotheses describing the mode of the stimulation of the protein translation by Mnk proteins. Most publications describe a positive stimulatory effect on the cap-dependent protein translation upon activation of MAP kinase-interacting kinases. Thus, the activation of Mnk proteins can lead to an indirect stimulation or regulation of the protein translation, e.g. by the effect on the cytosolic phospholipase 2 alpha (BBA 1488:124-138, 2000).

WO 03/037362 discloses a link between human Mnk genes, particularly the variants of the human Mnk2 genes, and diseases which are associated with the regulation of body weight or thermogenesis. It is postulated that human Mnk genes, particularly the Mnk2 variants are involved in diseases such as e.g. metabolic diseases including obesity, eating disorders, cachexia, diabetes mellitus, hypertension, coronary heart disease, hypercholesterolemia, dyslipidemia, osteoarthritis, biliary stones, cancer of the genitals and sleep apnea, and in diseases connected with the ROS defense, such as e.g. diabetes mellitus and cancer. WO 03/03762 moreover discloses the use of nucleic acid sequences of the MAP kinase-interacting kinase (Mnk) gene family and amino acid sequences encoding these and the use of these sequences or of effectors of Mnk nucleic acids or polypeptides, particularly Mnk inhibitors and activators in the diagnosis, prophylaxis or therapy of diseases associated with the regulation of body weight or thermogenesis.

WO 02/103361 describes the use of kinases 2a and 2b (Mnk2a and Mnk2b) interacting with the human MAP kinase in assays for the identification of pharmacologically active ingredients, particularly useful for the treatment of diabetes mellitus type 2. Moreover, WO 02/103361 discloses also the prophylaxis and/or therapy of diseases associated with insulin resistance, by modulation of the expression or the activity of Mnk2a or Mnk2b. Apart from peptides, peptidomimetics, amino acids, amino acid analogues, polynucleotides, polynucleotide analogues, nucleotides and nucleotide analogues, 4-hydroxybenzoic acid methyl ester are described as a substance which binds the human Mnk2 protein.

Inhibitors of Mnk (referred to as CGP57380 and CGP052088) have been described (cf. Mol. Cell. Biol. 21, 5500, 2001; Mol Cell Biol Res Comm 3, 205, 2000; Genomics 69, 63, 2000). CGP052088 is a staurosporine derivative having an $IC_{50}$ of 70 nM for inhibition of in vitro kinase activity of Mnk1. CGP57380 is a low molecular weight selective, non-cytotoxic inhibitor of Mnk2 (Mnk2a or Mnk2b) or of Mnk1: The addition of CGP57380 to cell culture cells, transfected with Mnk2 (Mnk2a or Mnk2b) or Mnk1 showed a strong reduction of phosphorylated eIF4E.

The problem underlying the present invention is to provide potent and selective Mnk1 and/or Mnk2 inhibitors which may effectively and safely be used for the treatment of metabolic diseases and their consecutive complication and disorders.

It has now been surprisingly found that certain pyrazolopyrimidine compounds are potent inhibitors of the kinase enzymes Mnk1 and/or Mnk2 and/or variants thereof and as such may be useful in the prophylaxis and/or therapy of diseases which can be influenced by the inhibition of the kinase activity of Mnk1 and/or Mnk2 (Mnk2a or Mnk2b) and/or variants thereof.

The present invention relates to the use of pyrazolopyrimidine compounds of the general formula (I)

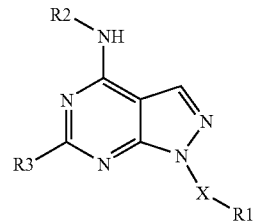

wherein $R^1$ is substituted aryl having 6 to 10 carbon atoms or optionally substituted heteroaryl having 5 to 10 ring atoms, wherein the substituents are one or more of $R^4$, wherein $R^4$ is independently halogen; CN; $COOR^5$; $OR^5$; $C(O)N(R^5R^{5a})$; $S(O)_2N(R^5R^{5a})$; $S(O)N(R^5R^{5a})$; $S(O)_2R^5$; $N(R^5)S(O)_2N(R^5R^{5a})$; $SR^5$; $N(R^5R^{5a})$; $OC(O)R^5$; $N(R^5)C(O)R^{5a}$; $N(R^5)S(O)_2R^{5a}$; $N(R^5)S(O)R^{5a}$; $N(R^5)C(O)N(R^{5a}R^{5b})$; $N(R^5)C(O)OR^{5a}$; $OC(O)N(R^5R^{5a})$; oxo (=O), where the ring is at least partially saturated; $C(O)R^5$; $T^1$; or $C_{1-6}$ alkyl, wherein $C_{1-6}$ alkyl is optionally substituted with one or more $R^6$;

$R^5$, $R^{5a}$ and $R^{5b}$ are independently selected from the group consisting of H; $T^1$; and $C_{1-6}$ alkyl, wherein $C_{1-6}$ alkyl is optionally substituted with one or more $R^7$;

$R^6$, $R^7$ are independently selected from the group consisting of halogen; CN; $COOR^8$; $OR^8$; $C(O)R^8$; $C(O)N(R^8R^{8a})$; $S(O)_2N(R^8R^{8a})$; $S(O)N(R^8R^{8a})$; $S(O)_2R^8$; $N(R^8)S(O)_2N(R^{8a}R^{8b})$; $SR^8$; $N(R^8R^{8a})$; $OC(O)R^8$; $N(R^8)C(O)R^{8a}$; $N(R^8)S(O)_2R^{8a}$; $N(R^8)S(O)R^{8a}$; $N(R^8)C(O)N(R^{8a}R^{8b})$; $N(R^8)C(O)OR^{8a}$; $OC(O)N(R^8R^{8a})$; and $T^1$;

$R^8$, $R^{8a}$, $R^{8b}$ are independently selected from the group consisting of H; $C_{1-6}$ alkyl; and $T^1$;

wherein $T^1$ is $C_{3-10}$ cycloalkyl; $C_{4-10}$ bicycloalkyl; $C_{4-10}$ heterocyclyl; $C_{4-10}$ heterobicyclyl; aryl having 6 to 10 carbon C atoms; heteroaryl having 5 to 10 ring atoms, wherein $T^1$ is optionally substituted with one or more $R^9$, wherein $R^9$ is independently halogen; CN; $COOR^{10}$; $OR^{10}$; $C(O)N(R^{10}R^{10a})$; $S(O)_2N(R^{10}R^{10a})$; $S(O)N(R^{10}R^{10a})$; $S(O)_2R^{10}$; $N(R^{10})S(O)_2N(R^{10a}R^{10b})$; $SR^{10}$;

N($R^{10}R^{10a}$); OC(O)$R^{10}$; N($R^{10}$)C(O)$R^{10a}$; N($R^{10}$)S(O)$_2$ $R^{10a}$; N($R^{10}$)S(O)$R^{10a}$; N($R^{10}$)C(O)N($R^{10a}R^{10b}$); N($R^{10}$)C(O)O$R^{10a}$; OC(O)N($R^{10}R^{10a}$); oxo (=O), where the ring is at least partially saturated; C(O)$R^{10}$; $C_{1-6}$ alkyl; phenyl; $C_{3-7}$ cycloalkyl; or heterocyclyl, wherein $C_{1-6}$ alkyl; phenyl; $C_{3-7}$ cycloalkyl; and heterocyclyl are optionally substituted with one or more halogen, which are the same or different;

$R^{10}$, $R^{10a}$ and $R^{10b}$ are independently selected from the group consisting of H, $C_{1-6}$ alkyl, phenyl, $C_{3-7}$ cycloalkyl, heteroaryl and heterocyclyl, wherein $C_{1-6}$ alkyl, phenyl, $C_{3-7}$ cycloalkyl and heterocyclyl are optionally substituted with one or more halogen, which are the same or different;

$R^2$ is hydrogen, $C_{1-4}$ alkyl, an acetyl group or a urea;

$R^3$ is hydrogen, a hydroxyl, $C_{1-4}$ alkyl; or amino group; and

X is a bond;

or a metabolite, prodrug or pharmaceutically acceptable salt thereof, and optionally a pharmaceutically acceptable carrier for the preparation of a pharmaceutical composition for inhibiting the activity of the kinase activity of Mnk1 or Mnk2 (Mnk2a, Mnk2b) or variants thereof.

In particular the present invention provides the use of the above identified compounds for the preparation of a pharmaceutical composition for the prophylaxis or therapy of metabolic diseases and hematopoietic disorders and their consecutive complications and disorders.

Diseases of the invention that are influenced by the inhibition of the kinase activity of Mnk1 and/or Mnk2 (Mnk2a or Mnk2b) and/or further variants thereof include diseases related to the regulation of metabolic diseases, such as obesity, eating disorders, cachexia, diabetes mellitus, metabolic syndrome, hypertension, coronary heart diseases, hypercholesterolemia, dyslipidemia, osteoarthritis, biliary stones and/or sleep apnea and diseases related to reactive oxygen compounds (ROS defence) such as diabetes mellitus, neurodegenerative diseases.

The pharmaceutical compositions of the invention are particularly useful for prophylaxis and treatment of obesity, diabetes mellitus and other metabolic diseases of the carbohydrate and lipid metabolism as stated above, in particular diabetes mellitus and obesity.

Thus is further preferred embodiments the present invention provides the use according to above for the prophylaxis or therapy of diseases of the carbohydrate and/or lipid metabolism and their consecutive complications and diseases, in particular for the prophylaxis or therapy of prophylaxis of metabolic diseases of the carbohydrate metabolism and their consecutive complications and disorders selected from impaired glucose tolerance, diabetes mellitus type II, LADA, diabetes mellitus type I, obesity, metabolic syndrome, eating disorders, chachexia, osteoarthritis, biliary stones, diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome diabetic coma with or without ketoacidosis, diabetic hyperosmolar coma, hypoglycaemic coma, hyperglycaemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic autonomic neuropathy, diabetic angiopathies, diabetic peripheral angiopathy, diabetic ulcer, diabetic arthropathy, or obesity in diabetes.

Moreover the present invention provides the use as described above for the treatment and/or prophylaxis of metabolic diseases of the lipid metabolism (i.e. lipid disorders) and their consecutive complications and disorders selected from hypercholesterolemia, dislipidemia familial hypercholesterolemia, Fredrickson's hyperlipoproteinemia, hyperbetalipoproteinemia, hyperlipidaemia, low-density-lipoprotein-type [LDL] hyperlipoproteinemia, pure hyperglyceridemia, endogenous hyperglyceridemia, isolated hypercholesterolemia, isolated hypertroglyceridemia, cardiovascular diseases selected from hypertension, ischemia, varicose veins, retinal vein occlusion, atherosclerosis, coronary heart disease, angina pectoris, myocardial infarction, stenocardia, pulmonary hypertension, congestive heart failure, glomerulopaty, tubulointestitial disorders, renal failure, angiostenosis, cerebrovascular disorders, or cerebral apoplexy.

Furthermore the present inventions provides the use of a pyrazolopyrimidine compound of the general formula (I)

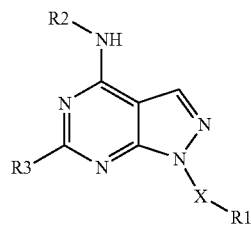

wherein $R^1$ is heteroaryl having 5 to 10 ring atoms, wherein heteroaryl is optionally substituted with one or more $R^4$, wherein $R^4$ is independently halogen; CN; COO$R^5$; O$R^5$; C(O)N($R^5R^{5a}$); S(O)$_2$N($R^5R^{5a}$); S(O)N($R^5R^{5a}$); S(O)$_2R^5$; N($R^5$)S(O)$_2$N($R^5R^{5a}$); S$R^5$; N($R^5R^{5a}$); OC(O)$R^5$; N($R^5$)C(O)$R^{5a}$; N($R^5$)S(O)$_2R^{5a}$; N($R^5$)S(O)$R^{5a}$; N($R^5$)C(O)N($R^{5a}R^{5b}$); N($R^5$)C(O)O$R^{5a}$; OC(O)N($R^5R^{5a}$); oxo (=O), where the ring is at least partially saturated; C(O)$R^5$; $T^1$; or $C_{1-6}$ alkyl, wherein $C_{1-6}$ alkyl is optionally substituted with one or more $R^6$;

$R^5$, $R^{5a}$ and $R^{5b}$ are independently selected from the group consisting of H; $T^1$; and $C_{1-6}$ alkyl, wherein $C_{1-6}$ alkyl is optionally substituted with one or more $R^7$;

$R^6$, $R^7$ are independently selected from the group consisting of halogen; CN; COO$R^8$; O$R^8$; C(O)$R^8$; C(O)N($R^8R^{8a}$); S(O)$_2$N($R^8R^{8a}$); S(O)N($R^8R^{8a}$); S(O)$_2R^8$; N($R^8$)S(O)$_2$N($R^{8a}R^{8b}$); S$R^8$; N($R^8R^{8a}$); OC(O)$R^8$; N($R^8$)C(O)$R^{8a}$; N($R^8$)S(O)$_2R^{8a}$; N($R^8$)S(O)$R^{8a}$; N($R^8$)C(O)N($R^{8a}R^{8b}$); N($R^8$)C(O)O$R^{8a}$; OC(O)N($R^8R^{8a}$); and $T^1$;

$R^8$, $R^{8a}$, $R^{8b}$ are independently selected from the group consisting of H; $C_{1-6}$ alkyl; and $T^1$;

wherein $T^1$ is $C_{3-10}$ cycloalkyl; $C_{4-10}$ bicycloalkyl; $C_{4-10}$ heterocyclyl; $C_{4-10}$ heterobicyclyl; aryl having 6 to 10 carbon C atoms; heteroaryl having 5 to 10 ring atoms, wherein $T^1$ is optionally substituted with one or more $R^9$, wherein $R^9$ is independently halogen; CN; COO$R^{10}$; O$R^{10}$; C(O)N($R^{10}R^{10a}$); S(O)$_2$N($R^{10}R^{10a}$); S(O)N($R^{10}R^{10a}$); S(O)$_2R^{10}$; N($R^{10}$)S(O)$_2$N($R^{10a}R^{10b}$); S$R^{10}$; N($R^{10}R^{10a}$); OC(O)$R^{10}$; N($R^{10}$)C(O)$R^{10a}$; N($R^{10}$)S(O)$_2$ $R^{10a}$; N($R^{10}$)S(O)$R^{10a}$; N($R^{10}$)C(O)N($R^{10a}R^{10b}$); N($R^{10}$)C(O)O$R^{10a}$; OC(O)N($R^{10}R^{10a}$); oxo (=O), where the ring is at least partially saturated; C(O)$R^{10}$; $C_{1-6}$ alkyl; phenyl; $C_{3-7}$ cycloalkyl; or heterocyclyl, wherein $C_{1-6}$ alkyl; phenyl; $C_{3-7}$ cycloalkyl; and heterocyclyl are optionally substituted with one or more halogen, which are the same or different;

R[10], R[10a] and R[10b] are independently selected from the group consisting of H, $C_{1-6}$ alkyl, phenyl, $C_{3-7}$ cycloalkyl, heteroaryl and heterocyclyl, wherein $C_{1-6}$ alkyl, phenyl, $C_{3-7}$ cycloalkyl and heterocyclyl are optionally substituted with one or more halogen, which are the same or different;

$R^2$ is hydrogen, $C_{1-4}$ alkyl, an acetyl group or a urea;

$R^3$ is hydrogen, a hydroxyl, $C_{1-4}$ alkyl; or amino group; and

X is a bond;

or a metabolite, prodrug or pharmaceutically acceptable salt thereof, and optionally a pharmaceutically acceptable carrier for the preparation of a pharmaceutical composition for the prophylaxis or therapy of cancer.

In a preferred embodiment $R^2$ is hydrogen.

In a further preferred embodiment the halogen atom is selected from chlorine and fluorine.

$R^1$ is preferably a phenyl group substituted with imidazolyl, a phenyl group substituted with condensed pyrazolo, a phenyl group substituted with trifluoromethyl, a phenyl thio or furanyl group.

Even more preferred is the use of compounds, wherein X is a bond and $R^1$ is a phenyl or substituted phenyl group, wherein the substituents are selected from halogen, carbamoyl, substituted carbamoyl, carboxyl, heterocyclyl and benzofused heterocyclyl or $R^1$ is a 5-13 membered mono- or bicyclic saturated or unsaturated optionally substituted heterocycle with 1-4 heteroatoms selected from N, S and O, wherein the substituents are selected from halogen, optionally substituted amino ($C_1$-$C_4$ alkyl or phenyl), carboxy, carbamoyl, $C_1$-$C_4$ alkoxycarbonyl, carboxymethyl, carbamoylmethyl, $C_1$-$C_4$ alkoxycarbonylmethyl, hydroxyl, phenoxy and $C_1$-$C_4$ alkyl.

In a further preferred embodiment the present invention relates to the use of are compounds wherein the group —X—$R^1$ is selected from: 3-chlorophenyl, 4-pyridyl, 5-indazolyl, 4-phenoxyphenyl, 3-carboxamidophenyl, (3-(3H-imidazol-4-yl)phenyl, 3-hydroxypyridaz-6-yl, 4-fluorophenyl, 6-indazolyl, 3-fluorophenyl, 4-chlorophenyl, 3-methoxyphenyl, 3-difluoromethoxyphenyl, 3,5-dichlorophenyl and 3-carboxyphenyl.

The following compounds are particularly preferred for inhibiting the activity of the kinase activity of Mnk1 or Mnk2 (Mnk2a, Mnk2b) or variants thereof, in particular for the prophylaxis or therapy of metabolic diseases and hematopoietic disorders and their consecutive complications and diseases.

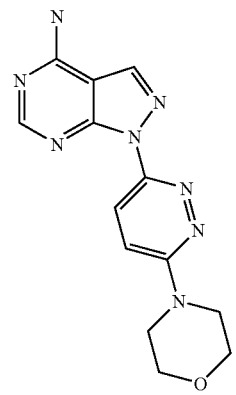
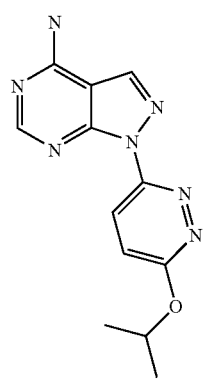
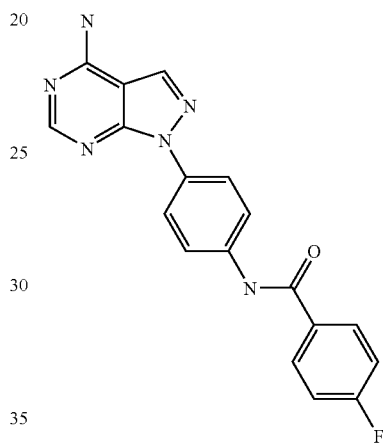
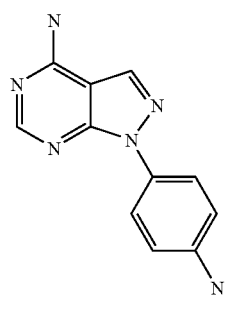
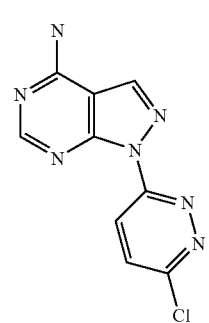
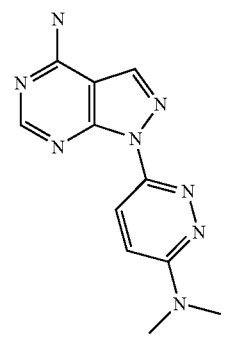
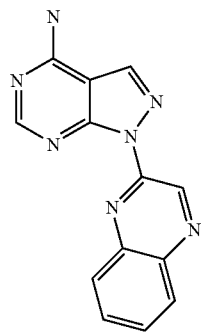
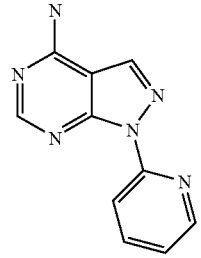
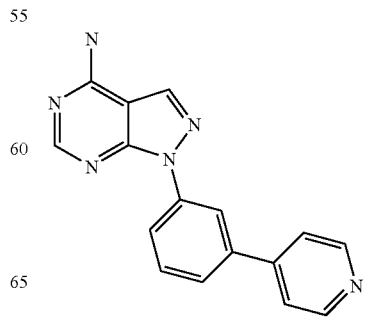
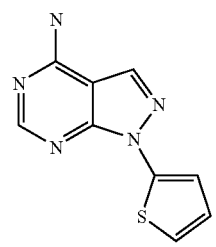

-continued
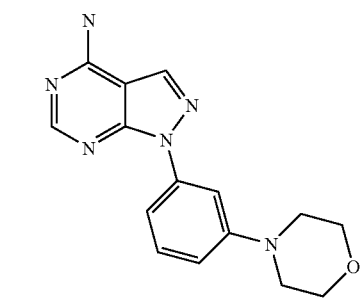
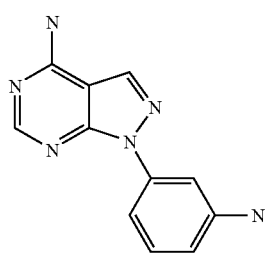
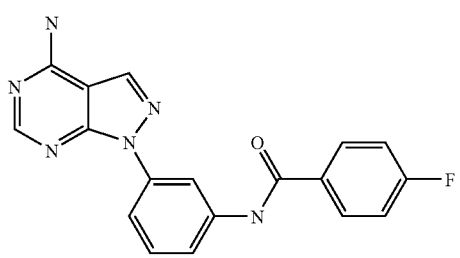
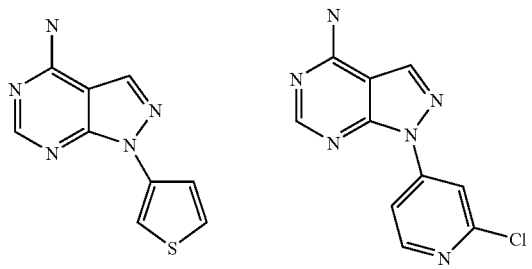
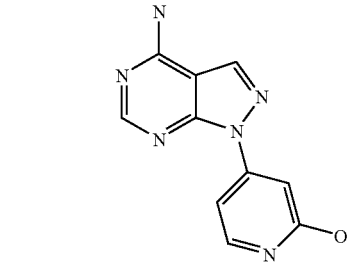
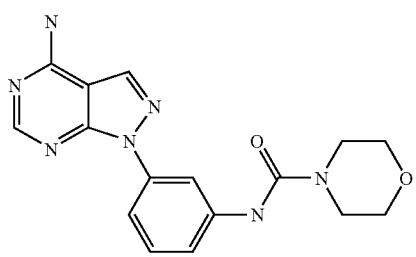
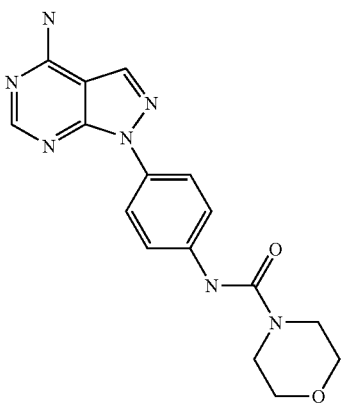
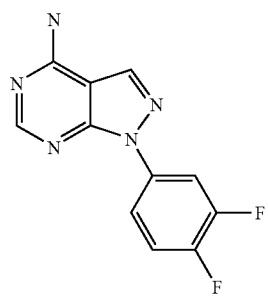
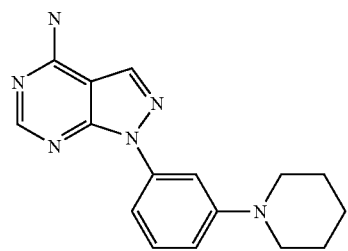
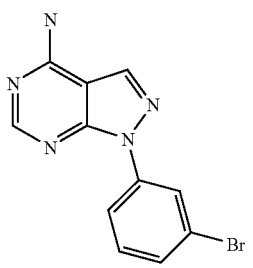

11
-continued
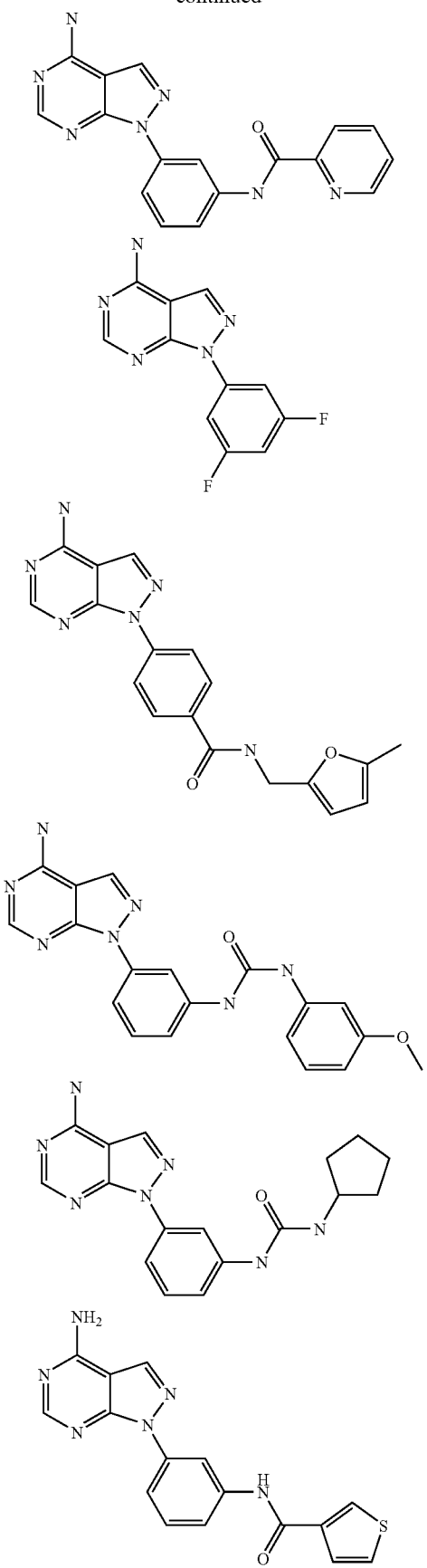
12
-continued
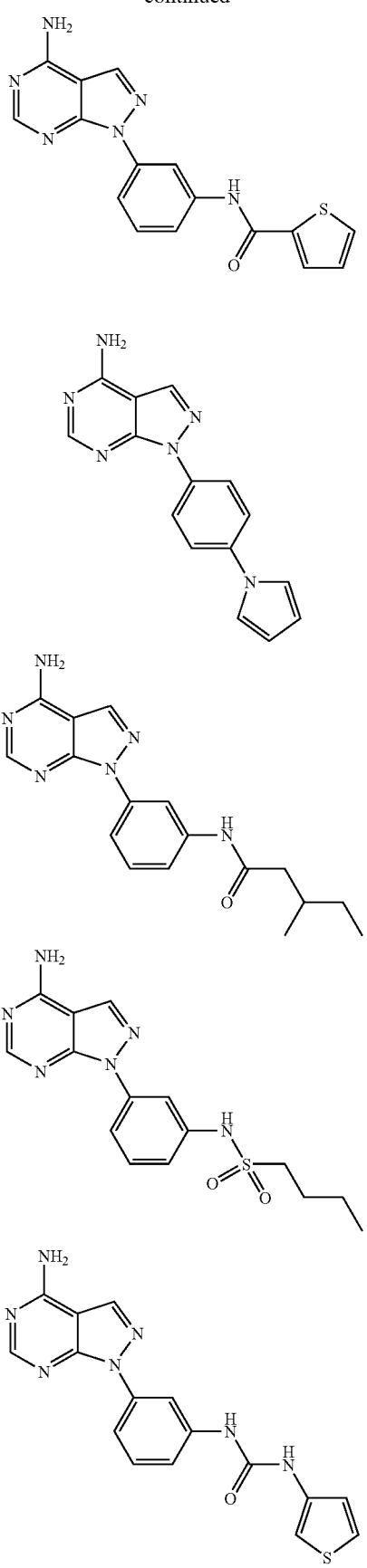

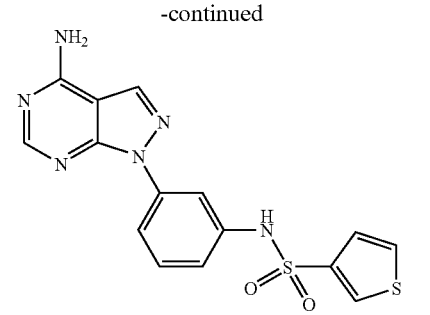
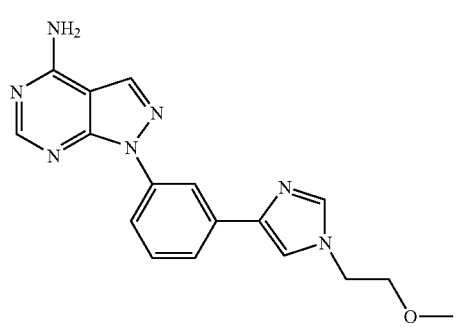
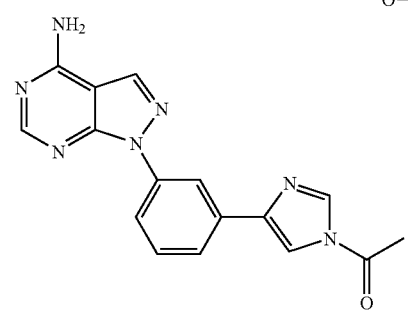
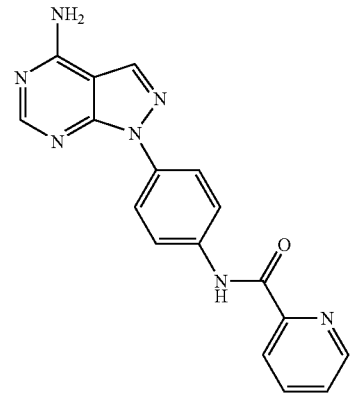
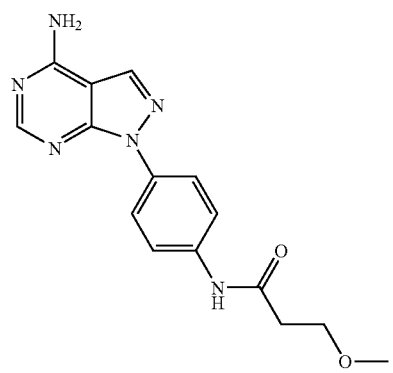
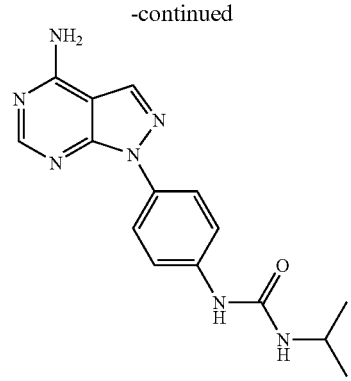
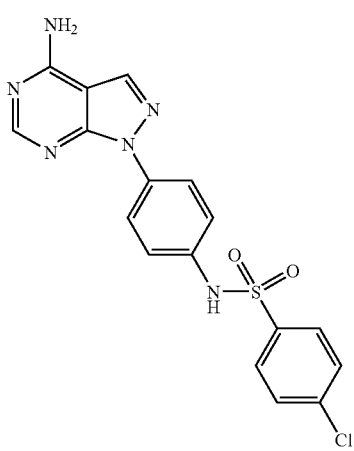
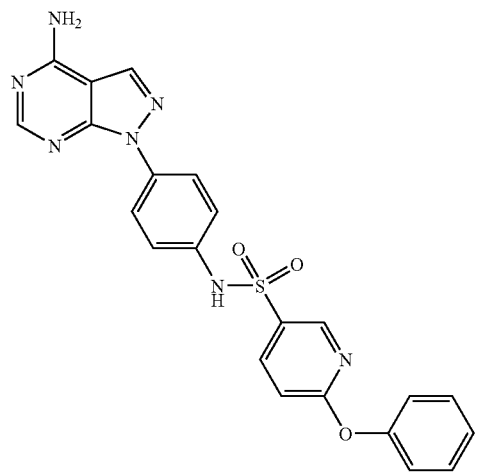
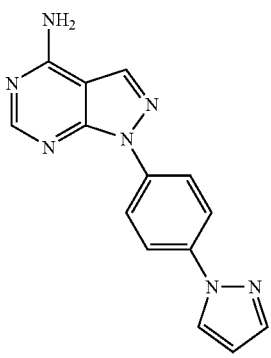

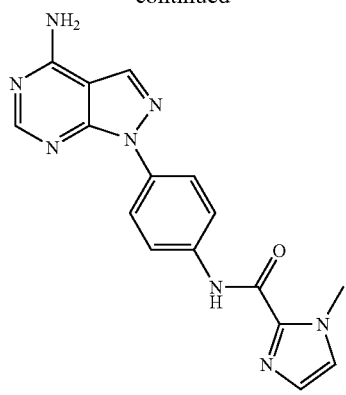
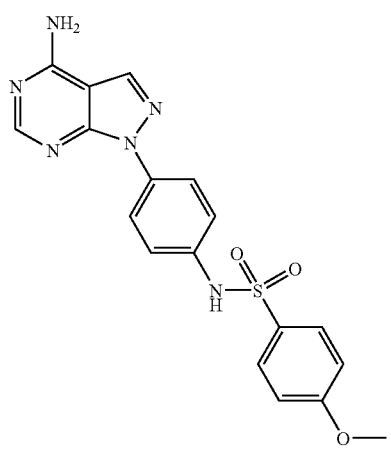
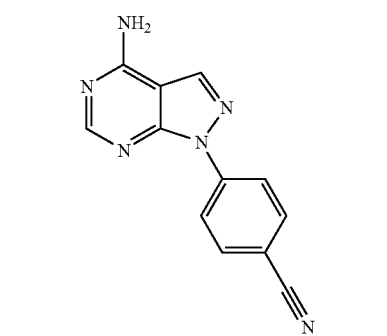
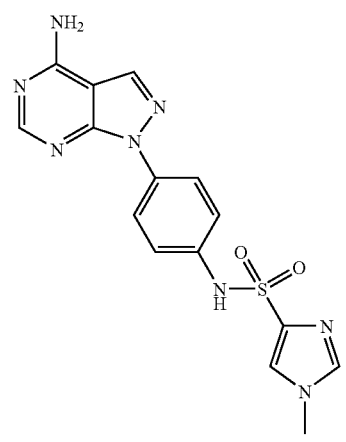
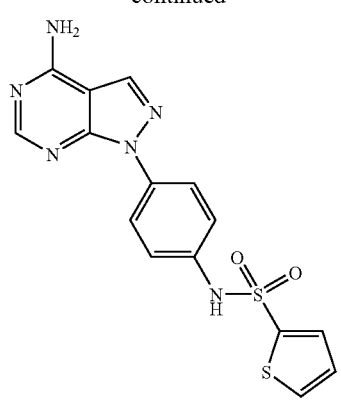
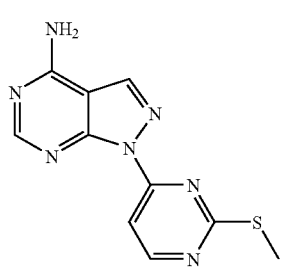
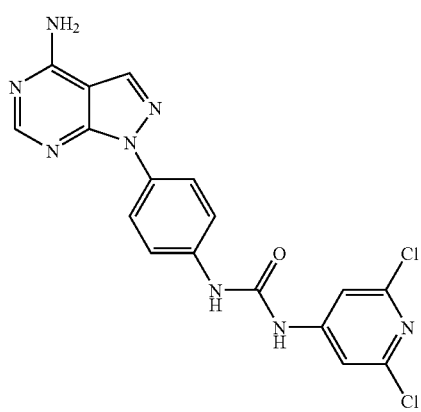
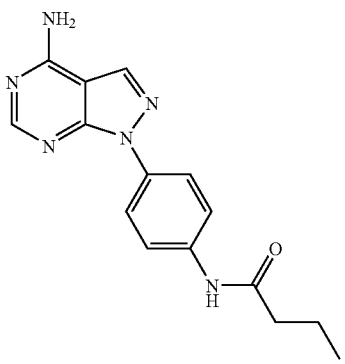

-continued
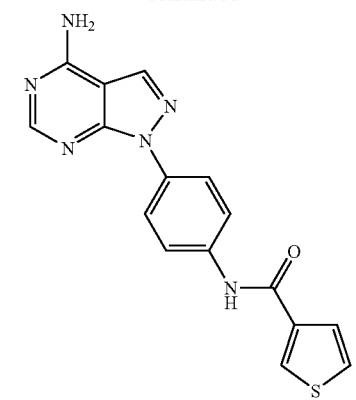
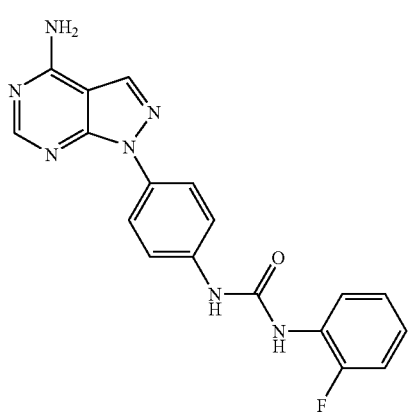
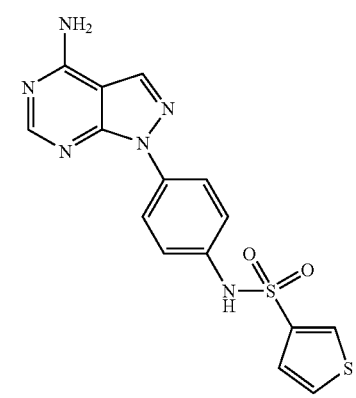
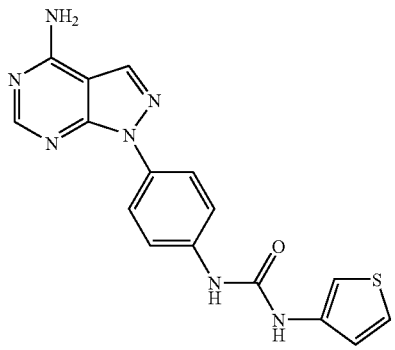
-continued
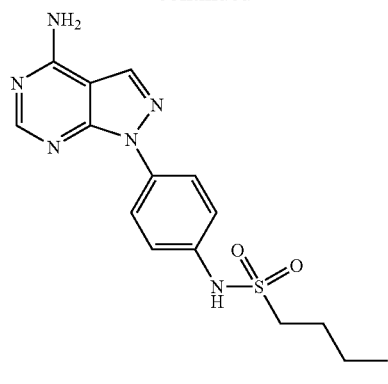
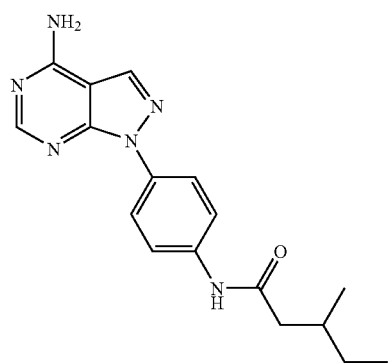
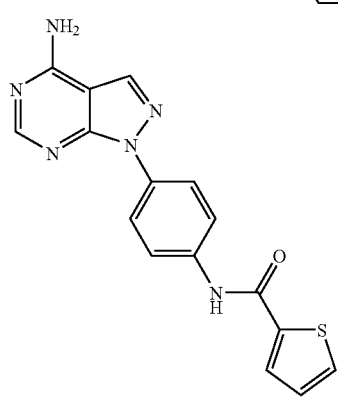
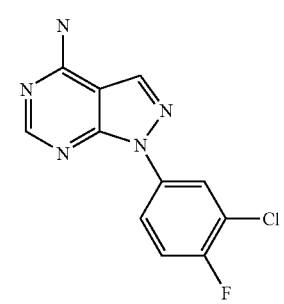
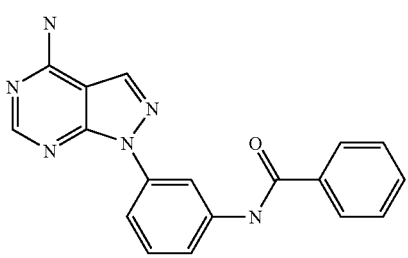

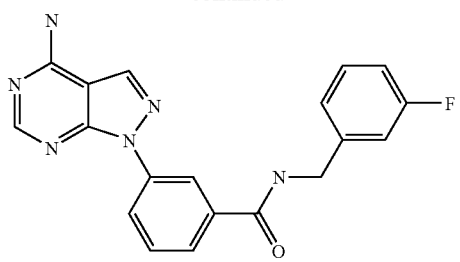
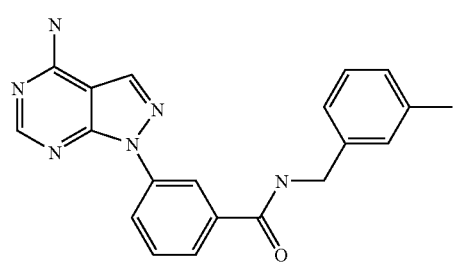
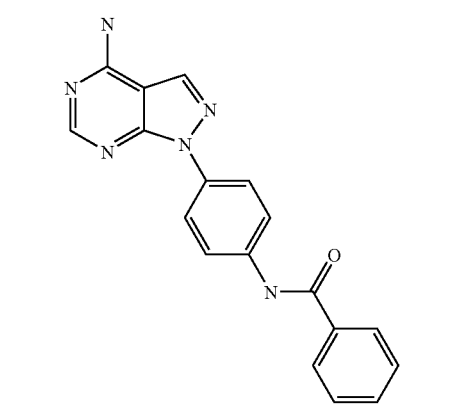
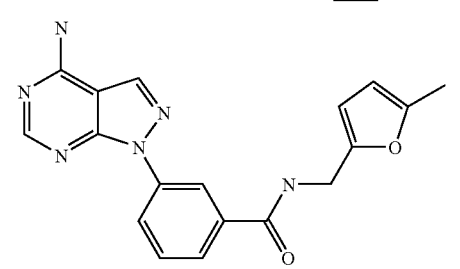
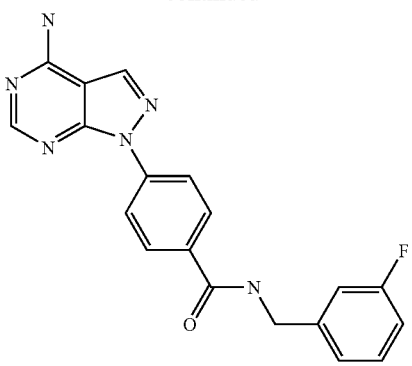
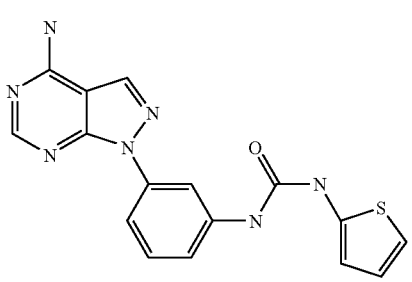
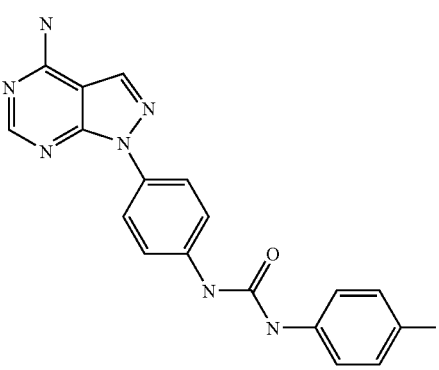
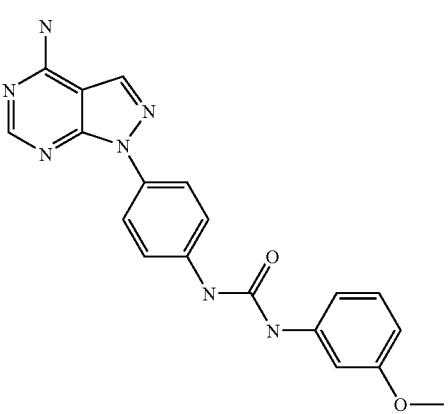

-continued
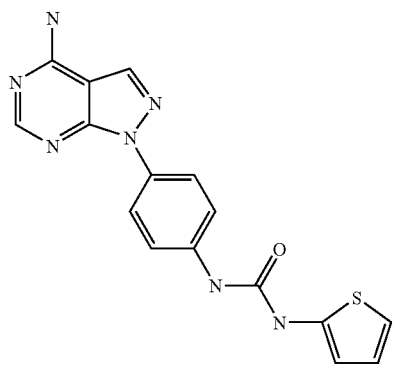
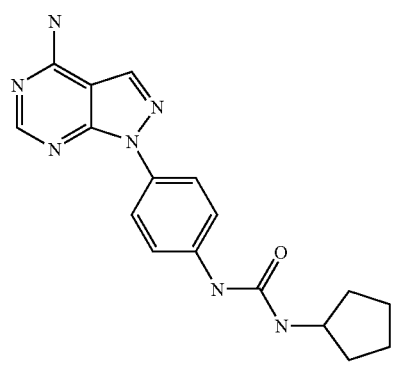
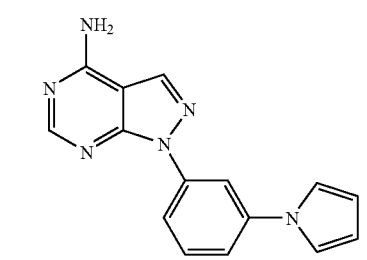
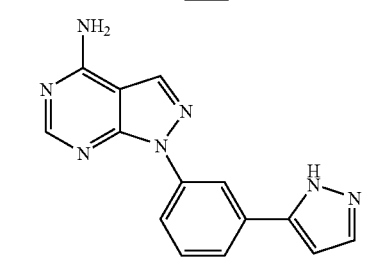
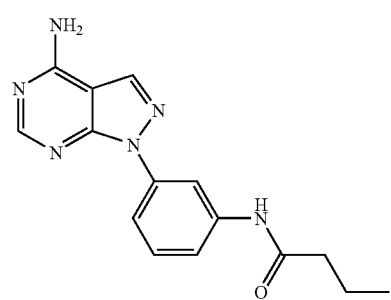
-continued
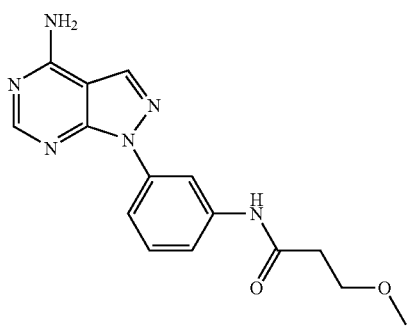
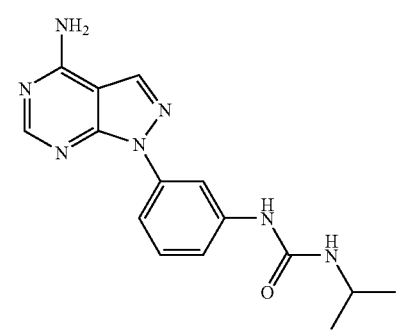
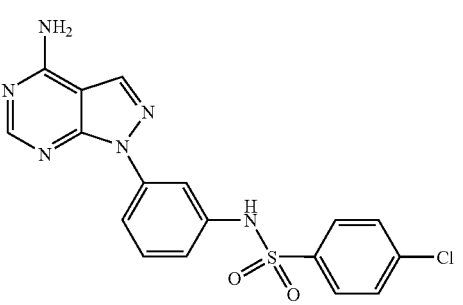
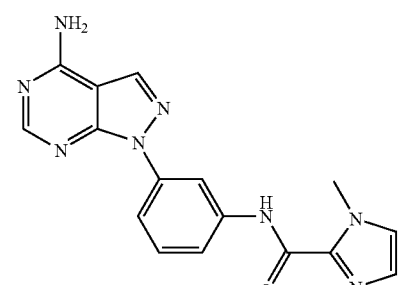
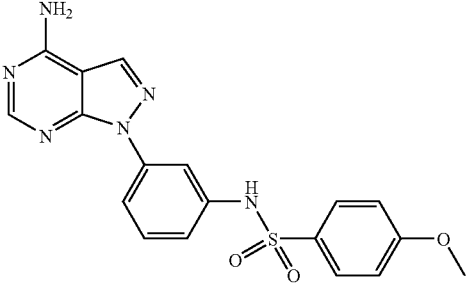

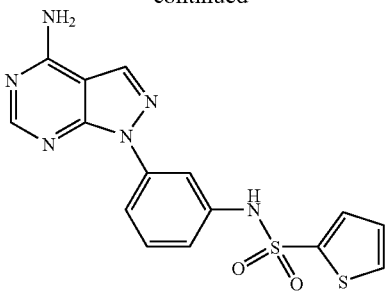

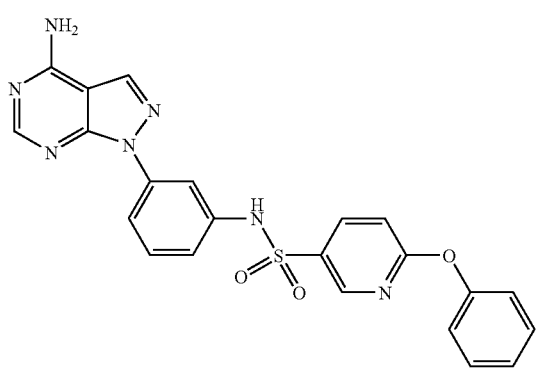

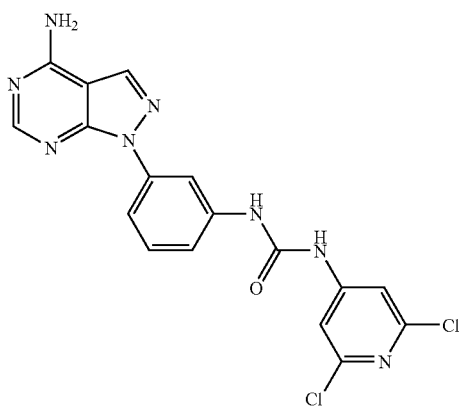

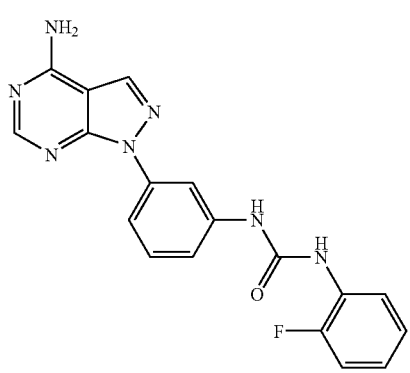

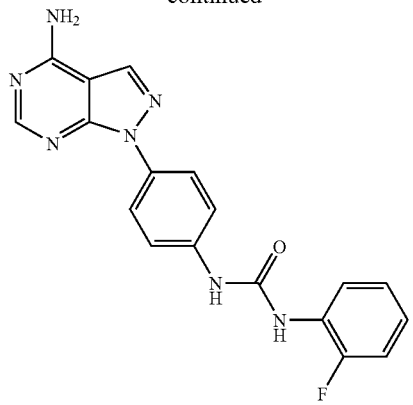

1-(1H-indazol-5-yl)-1H-pyrazolo[3,4-d]pyrimidin-4-ylamine,
1-(4-phenoxy-phenyl)-1H-pyrazolo[3,4-d]pyrimidin-4-ylamine,
3-(4-amino-pyrazolo[3,4-d]pyrimidin-1-yl)-bezamide,
1-[3-(3H-imidazol-4-yl)-phenyl]-1H-pyrazolo[3,4-d]pyrimidin-4-ylamine,
1-(4-fluoro-phenyl)-1H-pyrazolo[3,4-d]pyrimidin-4-ylamine,
1-(1H-indazol-6-yl)-1H-pyrazolo[3,4-d]pyrimidin-4-ylamine,
5-(4-amino-pyrazolo[3,4-d]pyrimidin-1-yl)-2-chloro-benzamide,
3-(4-amino-pyrazolo[3,4-d]pyrimidin-1-yl)-benzoic acid,
1-(3-difluoromethoxy-phenyl)-1H-pyrazolo[3,4-d]pyrimidin-4-ylamine,
1-(3-methoxy-phenyl)-1H-pyrazolo[3,4-d]pyrimidin-4-ylamine,
1-(3-fluoro-phenyl)-1H-pyrazolo[3,4-d]pyrimidin-4-ylamine,
1-pyridin-2-yl-1H-pyrazolo[3,4-d]pyrimidin-4-ylamine,
1-benzooxazol-2yl-1H-pyrazolo[3,4-d]pyrimidin-4-ylamine,
1-quinoxalin-2-yl-1H-pyrazolo[3,4-d]pyrimidin-4-ylamine,
1-benzothiazol-2-yl-1H-prazolo[3,4-d]pyrimidin-4-ylamine,
1-pyridin-4-yl-1H-pyrazolo[3,4-d]pyrimidin-4-ylamine,
1-(3,5-dimethyl-1H-pyrazol-4-yl)-1H-pyrazolo[3,4-d]pyrimidin-4-ylamine,
1-(4-methyl-oxazol-2-yl)-1H-pyrazolo[3,4-d]pyrimidin-4-ylamine,
1-thiazol-2-yl-1H-pyrazolo[3,4-d]pyrimidin-4-ylamine,
1-(4-methyl-thiazol-2-yl)-1H-pyrazolo[3,4-d]pyrimidin-4-ylamine,
1-(4-tert-butyl-thiazol-2-yl)-1H-pyrazolo[3,4-d]pyrimidin-4-yl-amine, 1-(4H-[1,2,4]triazol-3-yl)-1H-pyrazolo[3,4-d]pyrimidin-4-ylamine,
1-pyridin-3-yl-1H-pyrazolo[3,4-d]pyrimidin-4-ylamine,
1-pyrimidin-5-yl-1H-pyrazolo[3,4-d]pyrimidin-4-ylamine,
1-pyrimidin-2-yl-1H-pyrazolo[3,4-d]pyrimidin-4-ylamine,
1-pyrimidin-4-yl-1H-pyrazolo[3,4-d]pyrimidin-4-ylamine,
2-(4-amino-pyrazolo[3,4-d]pyrimidin-1-yl)-thiazole-4-carboxylic acid,
2-(4-amino-pyrazolo[3,4-d]pyrimidin-1-yl)-thiazole-4-carboxylic acid methyl ester,
2-(4-amino-pyrazolo[3,4-d]pyrimidin-1-yl)-thiazole-4-carboxylic acid amide,
2-(4-amino-pyrazolo[3,4-d]pyrimidin-1-yl)-thiazole-5-carboxylic acid,
2-(4-amino-pyrazolo[3,4-d]pyrimidin-1-yl)-thiazole-5-carboylic acid methyl ester,
2-(4-amino-pyrazolo[3,4-d]pyrimidin-1-yl)-thiazole-5-carboxylic acid amide,
[2-(4-amino-pyrazolo[3,4-d]pyrimidin-1-yl)-thiazol-4-yl]-acetic acid,
[2-(4-amino-pyrazolo[3,4-d]pyrimidin-1-yl)-thiazol-4-yl]-acetic acid methyl ester,
2-[2-(4-amino-pyrazolo[3,4-d]pyrimidin-1-yl)-thiazol-4-yl]-acetamide,
[2-(4-amino-pyrazolo[3,4-d]pyrimidin-1-yl)-thiazol-5-yl]-acetic acid,
[2-(4-amino-pyrazolo[3,4-d]pyrimidin-1-yl)-thiazol-5-yl]-acetic acid methyl ester,
[2-(4-amino-pyrazolo[3,4-d]pyrimidin-1-yl)-thiazol-5-yl]-acetamide,
1-benzo[b]thiophen-3-yl-1H-pyrazolo[3,4-d]pyrimidin-4-ylamine,
1-(5-fluoro-benzo[b]thiophen-3-yl)-1H-pyrazolo[3,4-d]pyrimidin-4-ylamine,
1-(6-chloro-benzo[b]thiophen-3-yl)-1H-pyrazolo[3,4-d]pyrimidin-4-ylamine,
1-(7-chloro-benzo[b]thiophen-3-yl)-1H-pyrazolo[3,4-d]pyrimidin-4-ylamine,
1-(5-chloro-benzo[b]thiophen-3-yl)-1H-pyrazolo[3,4-d]pyrimidin-4-ylamine,
1-benzofuran-3-yl-1H-pyrazolo[3,4-d]pyrimidin-4-ylamine,
1-(5-fluoro-benzofuran-3-yl)-1H-pyrazolo[3,4-d]pyrimidin-4-ylamine,
1-(5-chloro-benzofuran-3-yl)-1H-pyrazolo[3,4-d]pyrimidin-4-ylamine,
1-(6-chloro-benzofuran-3-yl)-1H-pyrazolo[3,4-d]pyrimidin-4-ylamine,
1-(7-chloro-benzofuran-3-yl)-1H-pyrazolo[3,4-d]pyrimidin-4-ylamine,
1-(1H-indol-3-yl)-1H-pyrazolo[3,4-d]pyrimidin-4-ylamine,
1-(5-fluoro-1H-indol-3-yl)-1H-pyrazolo[3,4-d]pyrimidin-4-ylamine,
1-(5-chloro-1H-indol-3-yl)-1H-pyrazolo[3,4-d]pyrimidin-4-ylamine,
1-(6-chloro-1H-indol-3-yl)-1H-pyrazolo[3,4-d]pyramidin-4-ylamine,
1-(7-chloro-1H-indol-3-yl)-1H-pyrazolo[3,4-d]pyrimidin-4-ylamine,
1-(1H-pyrrolo[2,3-b]pyridin-3-yl)-1H-pyrazolo[3,4-d]pyrimidin-4-ylamine,
1-(1H-pyrrolo[2,3-c]pyridin-3-yl)-1H-pyrazolo[3,4-d]pyrimidin-4-ylamine,
1-(1H-pyrrolo[3,2-c]pyridin-3-yl)-1H-pyrazolo[3,4-d]pyrimidin-4-ylamine,
1-(1H-pyrrolo[3,2-b]pyridin-3-yl)-1H-pyrazolo[3,4-d]pyrimidin-4-ylamine,
1-quinazolin-4-yl-1H-pyrazolo[3,4-d]pyrimidin-4-ylamine,
6-(4-amino-pyrazolo[3,4-d]pyrimidin-1-yl)-pyridazin-3-ol,
1-(6-amino-pyridazin-3-yl)-1H-pyrazolo[3,4-d]pyrimidin-4-ylamine,
1-(6-dimethylamino-pyridazin-3-yl)-1H-pyrazolo[3,4-d]pyrimidin-4-ylamine,
1-(6-phenylamino-pyridazin-3-yl)-1H-pyrazolo[3,4-d]pyrimidin-4-ylamine,
1-(6-phenoxy-pyridazin-3-yl)-1H-pyrazolo[3,4-d]pyrimidin-4-ylamine,

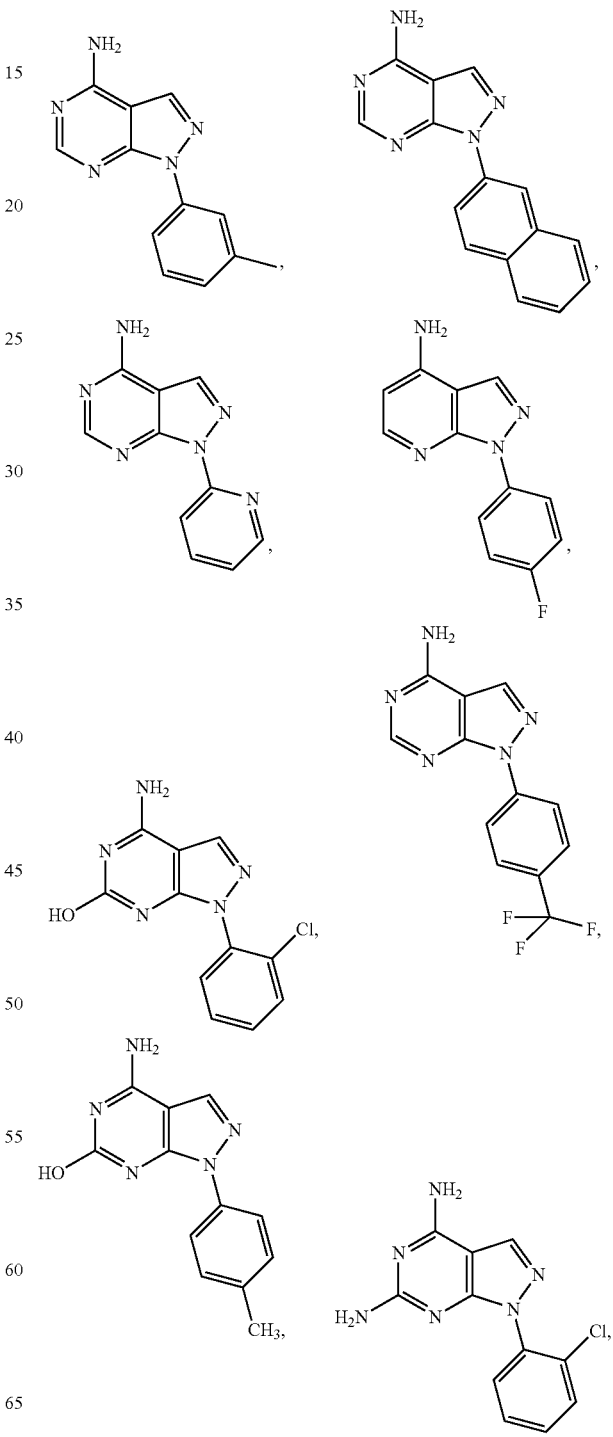

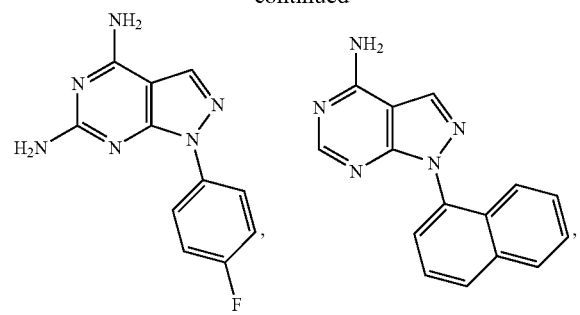
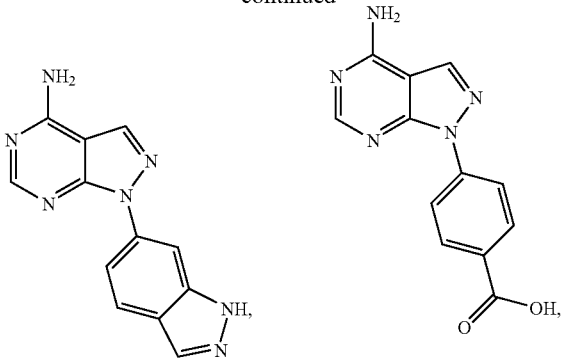
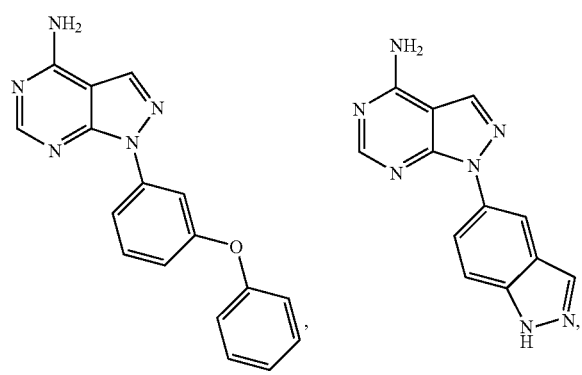
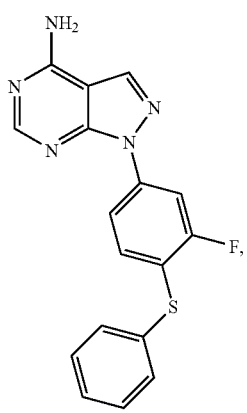
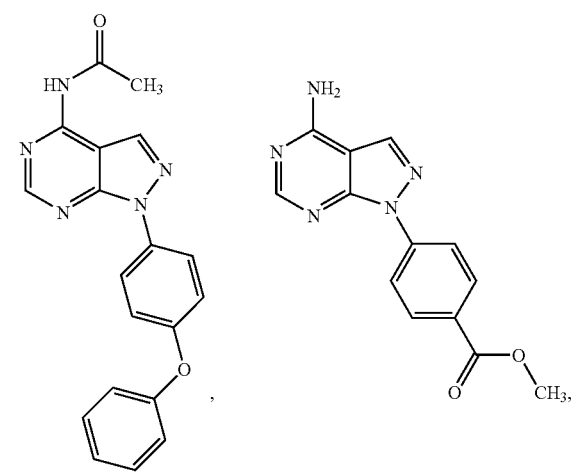
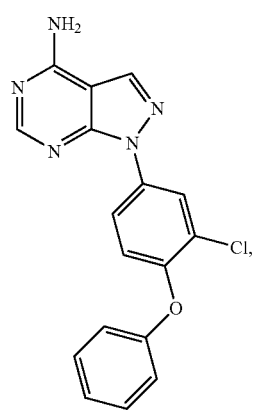
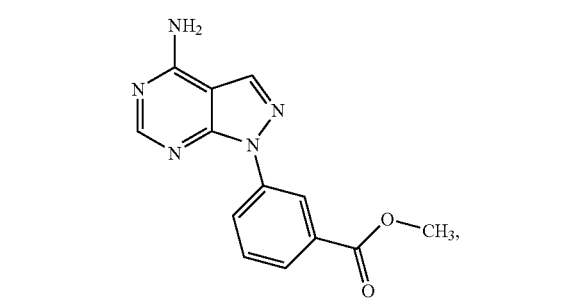
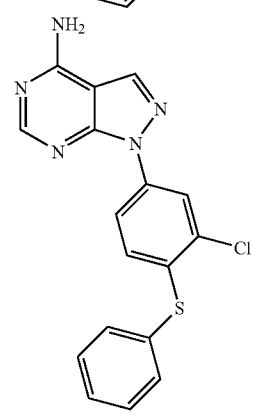

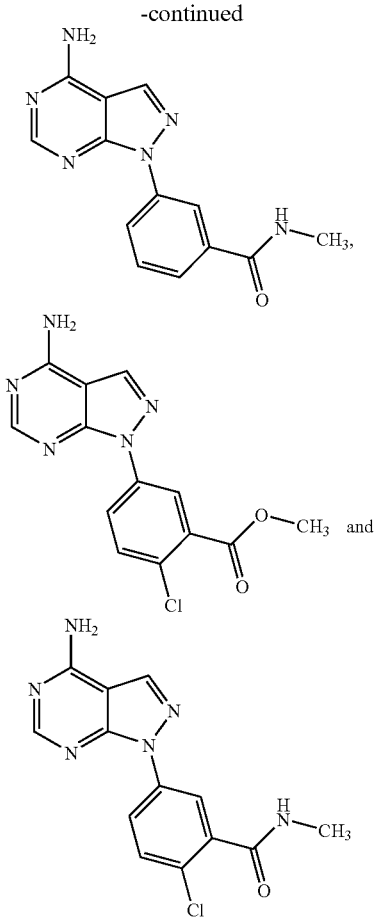

For the preparation of pharmaceutical compositions for the prophylaxis or therapy of cancer the use of the following is preferred
1-(1H-indazol-5-yl)-1H-pyrazolo[3,4-d]pyrimidin-4-ylamine,
1-(1H-indazol-6-yl)-1H-pyrazolo[3,4-d]pyrimidin-4ylamine,
1-pyrindin-2-yl-1H-pyrazolo[3,4-d]pyrimidin-4-ylamine,
1-benzooxazol-2yl-1H-pyrazolo[3,4-d]pyrimidin-4-ylamine,
1-quinoxalin-2-yl-1H-pyrazolo[3,4-d]pyrimidin-4-ylamine,
1-benzothiazol-2-yl-1H-prazolo[3,4-d]pyrimidin-4-ylamine,
1-pyridin-4-yl-1H-pyrazolo[3,4-d]pyrimidin-4-ylamine,
1-(3,5-dimethyl-1H-pyrazol-4-yl)-1H-pyrazolo[3,4-d]pyrimidin-4-ylamine,
1-(4-methyl-oxazol-2-yl)-1H-pyrazolo[3,4-d]pyrimidin-4-ylamine,
1-thiazol-2-yl-1H-pyrazolo[3,4-d]pyrimidin-4-ylamine,
1-(4-methyl-thiazol-2-yl)-1H-pyrazolo[3,4-d]pyrimidin-4-ylamine,
1-(4-tert-butyl-thiazol-2-yl)-1H-pyrazolo[3,4-d]pyrimidin-4-yl-amine,
1-(4H-[1,2,4]triazol-3-yl)-1H-pyrazolo[3,4-d]pyrimidin-4-ylamine,
1-pyridin-3-yl-1H-pyrazolo[3,4-d]pyrimidin-4-ylamine,
1-pyrimidin-5-yl-1H-pyrazolo[3,4-d]pyrimidin-4-ylamine,
1-pyrimidin-2-yl-1H-pyrazolo[3,4-d]pyrimidin-4-ylamine,
1-pyrimidin-4-yl-1H-pyrazolo[3,4-d]pyrimidin-4-ylamine,
2-(4-amino-pyrazolo[3,4-d]pyrimidin-1-yl)-thiazole-4-carboxylic acid,
2-(4-amino-pyrazolo[3,4-d]pyrimidin-1-yl)-thiazole-4-carboxylic acid methyl ester,
2-(4-amino-pyrazolo[3,4-d]pyrimidin-1-yl)-thiazole-4-carboxylic acid amide,
2-(4-amino-pyrazolo[3,4-d]pyrimidin-1-yl)-thiazole-5-carboxylic acid,
2-(4-amino-pyrazolo[3,4-d]pyrimidin-1-yl)-thiazole-5-carboylic acid methyl ester,
2-(4-amino-pyrazolo[3,4-d]pyrimidin-1-yl)-thiazole-5-carboxylic acid amide,
[2-(4-amino-pyrazolo[3,4-d]pyrimidin-1-yl)-thiazol-4-yl]-acetic acid,
[2-(4-amino-pyrazolo[3,4-d]pyrimidin-1-yl)-thiazol-4-yl]-acetic acid methyl ester,
2-[2-(4-amino-pyrazolo[3,4-d]pyrimidin-1-yl)-thiazol-4-yl]-acetamide,
[2-(4-amino-pyrazolo[3,4-d]pyrimidin-1-yl)-thiazol-5-yl]-acetic acid,
[2-(4-amino-pyrazolo[3,4-d]pyrimidin-1-yl)-thiazol-5-yl]-acetic acid methyl ester,
[2-(4-amino-pyrazolo[3,4-d]pyrimidin-1-yl)-thiazol-5-yl]-acetamide,
1-benzo[b]thiophen-3-yl-1H-pyrazolo[3,4-d]pyrimidin-4-ylamine,
1-(5-fluoro-benzo[b]thiophen-3-yl)-1H-pyrazolo[3,4-d]pyrimidin-4-ylamine,
1-(6-chloro-benzo[b]thiophen-3-yl)-1H-pyrazolo[3,4-d]pyrimidin-4-ylamine,
1-(7-chloro-benzo[b]thiophen-3-yl)-1H-pyrazolo[3,4-d]pyrimidin-4-ylamine,
1-(5-chloro-benzo[b]thiophen-3-yl)-1H-pyrazolo[3,4-d]pyrimidin-4-ylamine,
1-benzofuran-3-yl-1H-pyrazolo[3,4-d]pyrimidin-4-ylamine,
1-(5-fluoro-benzofuran-3-yl)-1H-pyrazolo[3,4-d]pyrimidin-4-ylamine,
1-(5-chloro-benzofuran-3-yl)-1H-pyrazolo[3,4-d]pyrimidin-4-ylamine,
1-(6-chloro-benzofuran-3-yl)-1H-pyrazolo[3,4-d]pyrimidin-4-ylamine,
1-(7-chloro-benzofuran-3-yl)-1H-pyrazolo[3,4-d]pyrimidin-4-ylamine,
1-(1H-indol-3-yl)-1H-pyrazolo[3,4-d]pyrimidin-4-ylamine,
1-(5-fluoro-1H-indol-3-yl)-1H-pyrazolo[3,4-d]pyrimidin-4-ylamine,
1-(5-chloro-1H-indol-3-yl)-1H-pyrazolo[3,4-d]pyrimidin-4-ylamine,
1-(6-chloro-1H-indol-3-yl)-1H-pyrazolo[3,4-d]pyramidin-4-ylamine,
1-(7-chloro-1H-indol-3-yl)-1H-pyrazolo[3,4-d]pyrimidin-4-ylamine,
1-(1H-pyrrolo[2,3-b]pyridine-3-yl)-1H-pyrazolo[3,4-d]pyrimidin-4-ylamine,
1-(1H-pyrrolo[2,3-c]pyridine-3-yl)-1H-pyrazolo[3,4-d]pyrimidin-4-ylamine,
1-(1H-pyrrolo[3,2-c]pyridine-3-yl)-1H-pyrazolo[3,4-d]pyrimidin-4-ylamine,
1-(1H-Pyrrolo[3,2-b]pyridine-3-yl)-1H-pyrazolo[3,4-d]pyrimidin-4-ylamine,
1-quinazolin-4-yl-1H-pyrazolo[3,4-d]pyrimidin-4-ylamine,
6-(4-amino-pyrazolo[3,4-d]pyrimidin-1-yl)-pyridazin-3-ol,
1-(6-amino-pyridazin-3-yl)-1H-pyrazolo[3,4-d]pyrimidin-4-ylamine,
1-(6-dimethylamino-pyridazin-3-yl)-1H-pyrazolo[3,4-d]pyrimidin-4-ylamine,
1-(6-phenylamino-pyridazin-3-yl)-1H-pyrazolo[3,4-d]pyrimidin-4-ylamine, 1-(6-phenoxy-pyridazin-3-yl)-1H-pyrazolo[3,4-d]pyrimidin-4-ylamine,

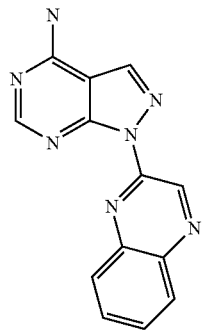
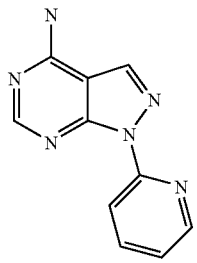
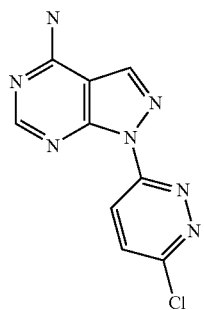
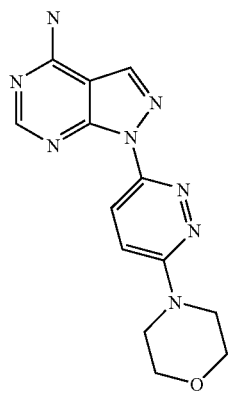
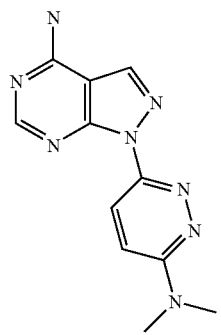
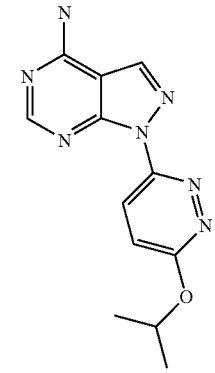
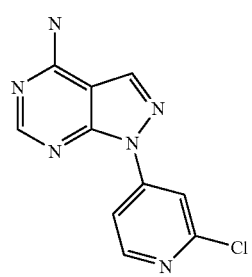
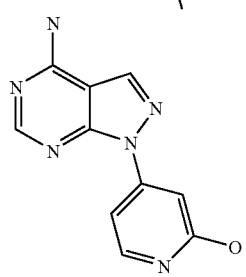
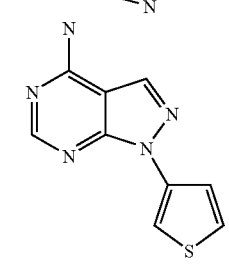
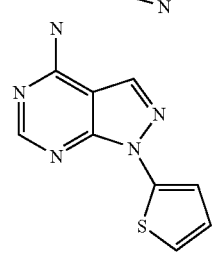

More particularly preferred for the preparation of pharmaceutical compositions for inhibiting the activity of the kinase activity of Mnk1 or Mnk2 (Mnk2a, Mnk2b) or variants thereof, in particular for the prophylaxis or therapy of metabolic diseases and hematopoietic disorders and their consecutive complications and disease are the following compounds:

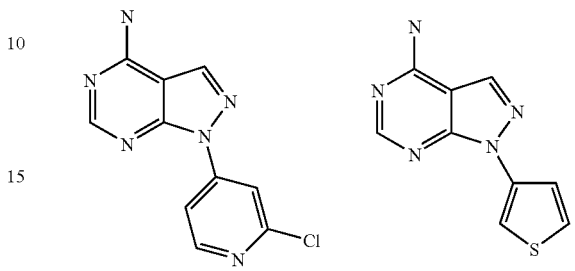
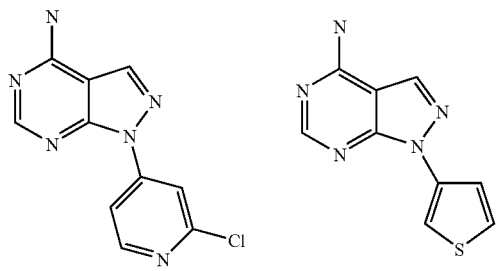
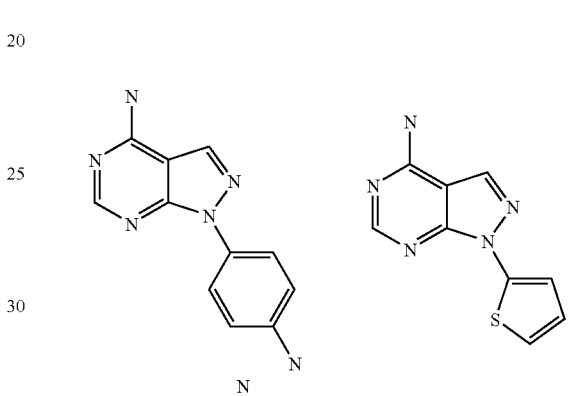
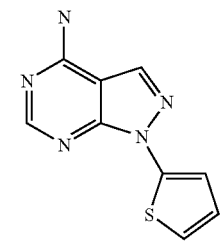
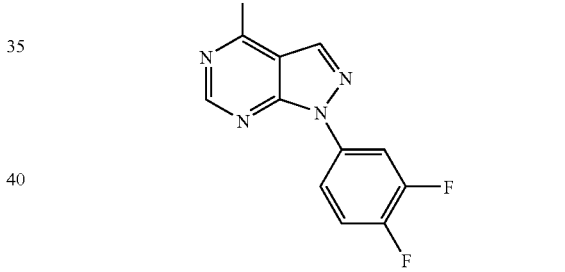
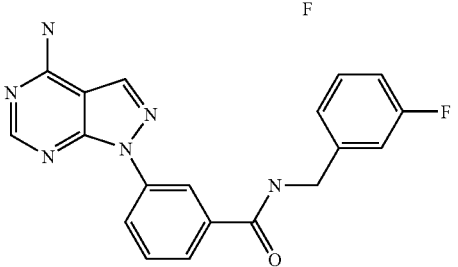
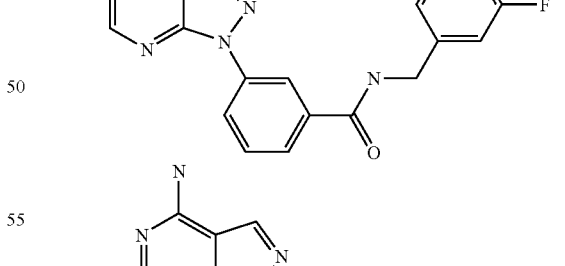
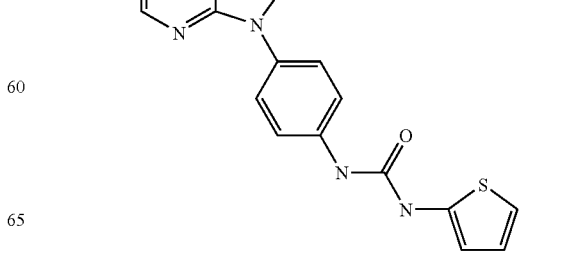
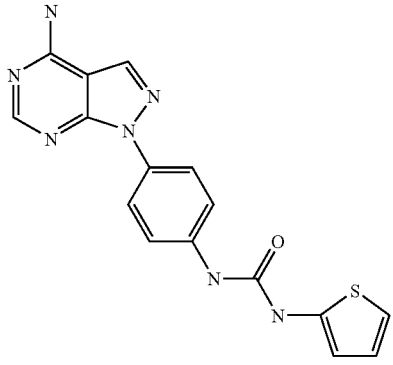

33
-continued
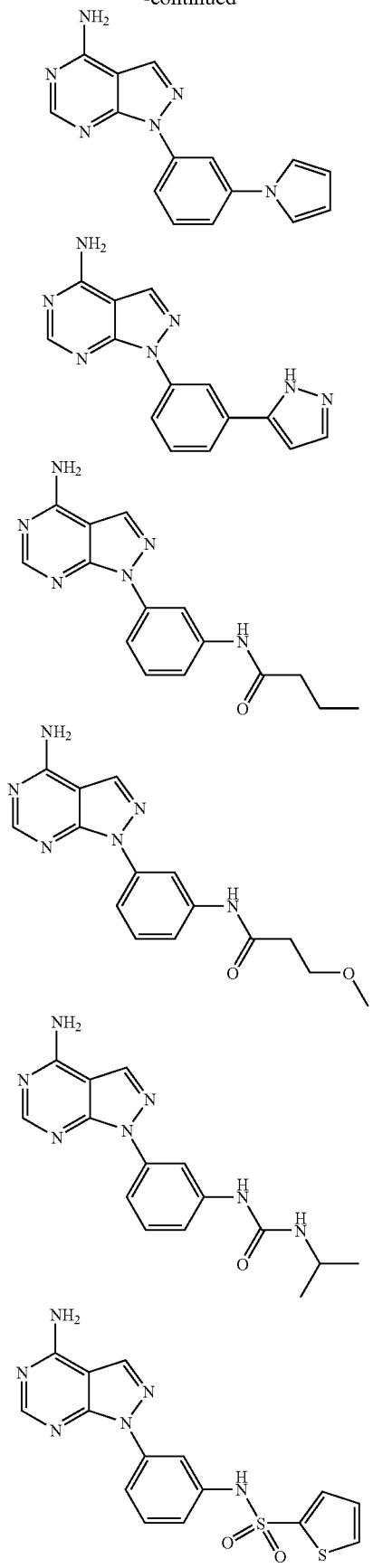
34
-continued
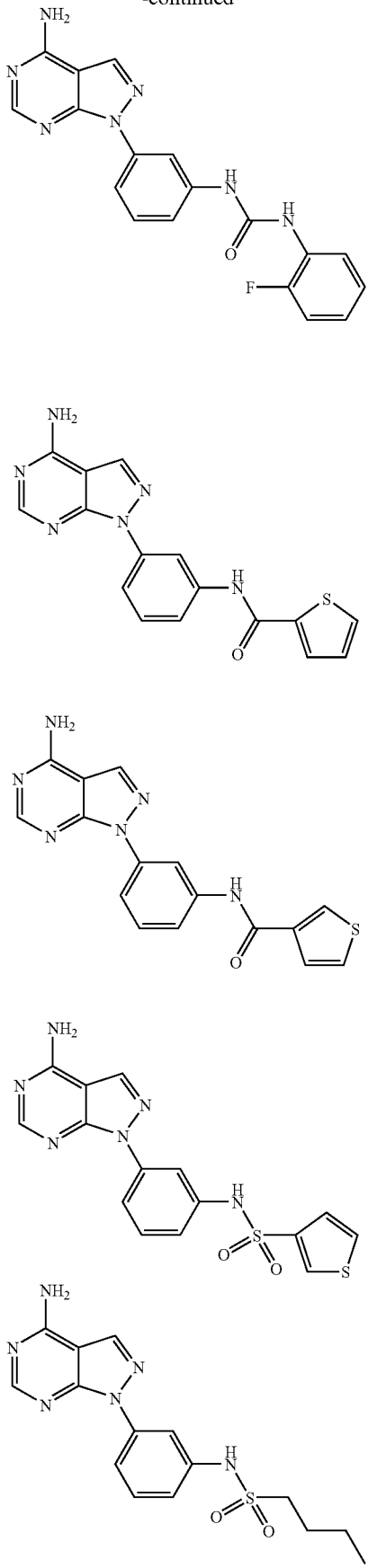

-continued
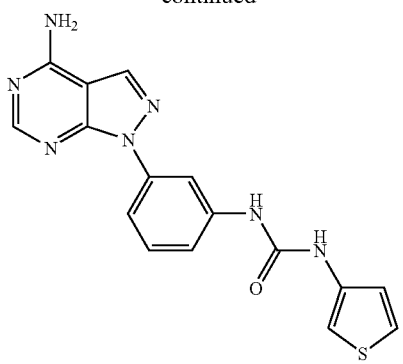
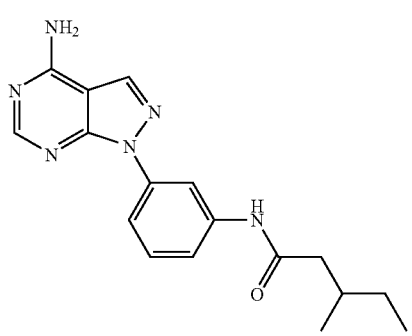
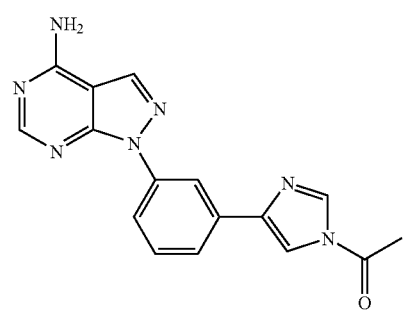
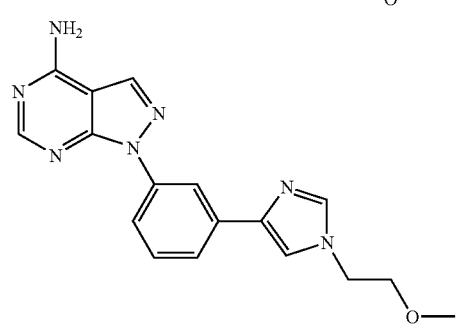
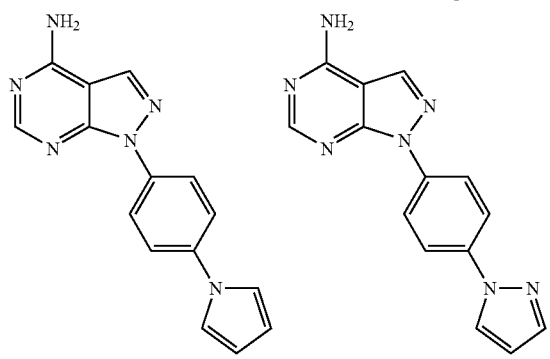
-continued
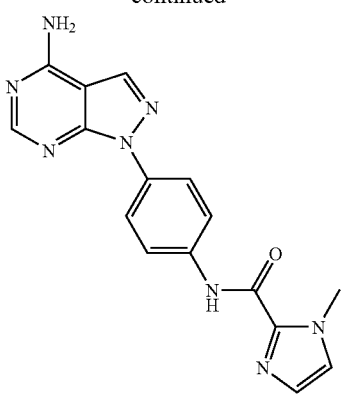
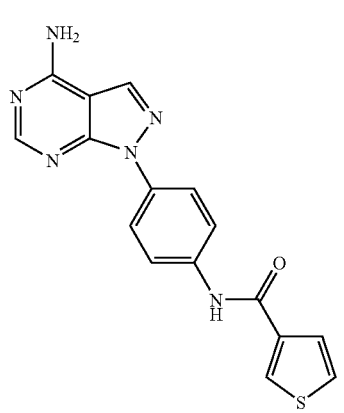
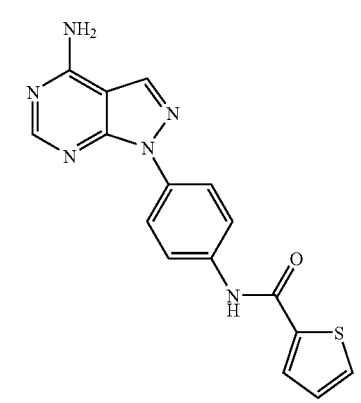
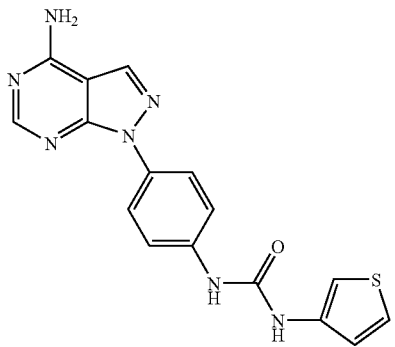

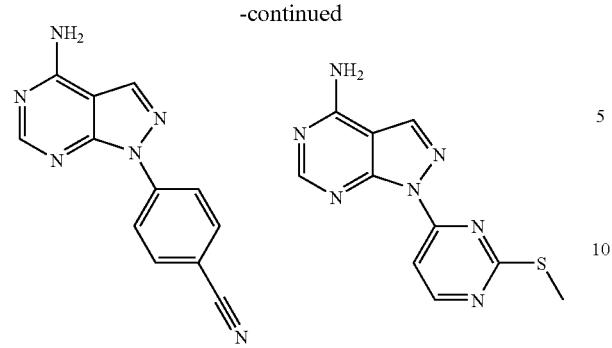
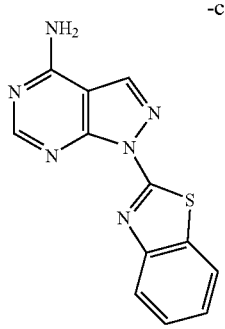
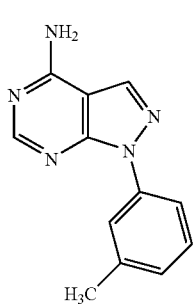
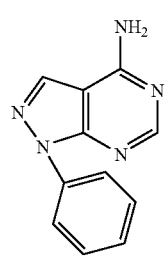
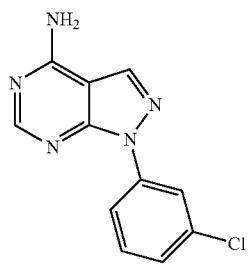
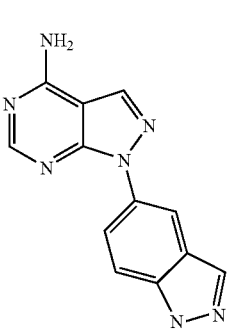
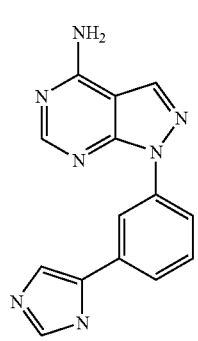
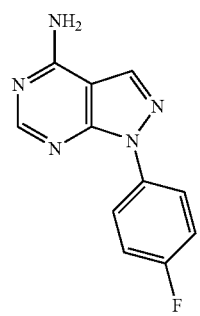
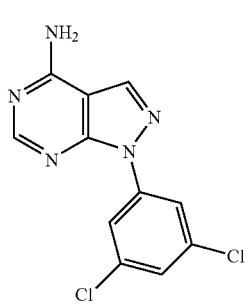
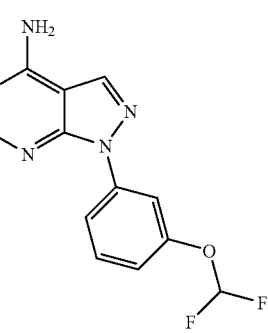
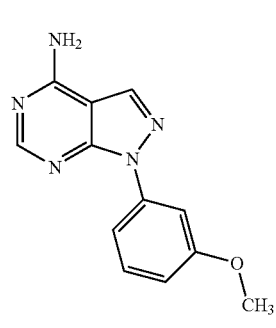
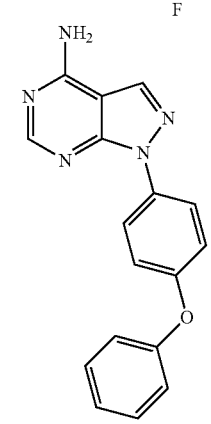
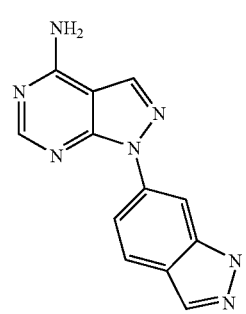
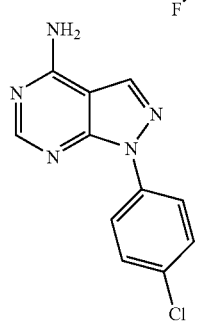
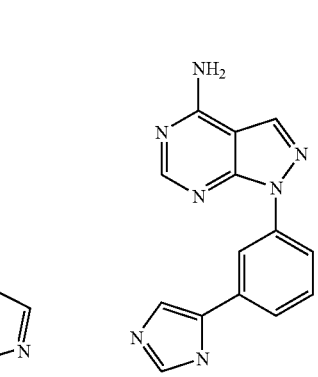
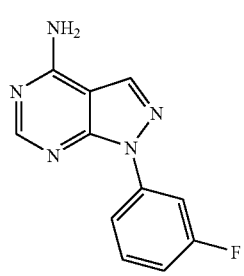
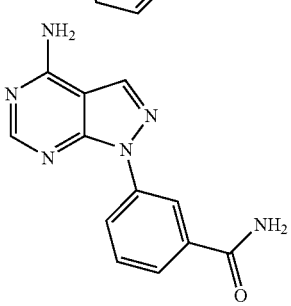
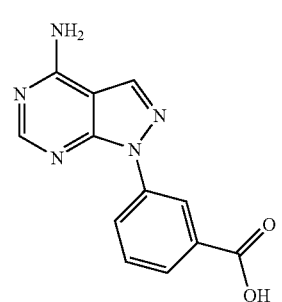
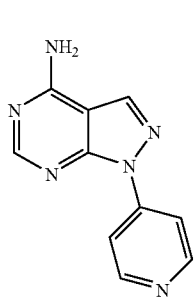
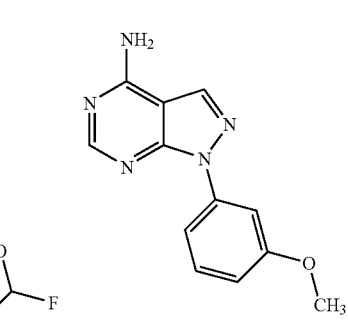
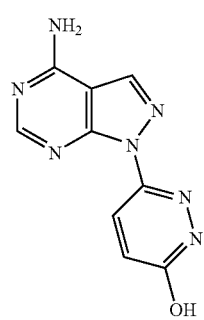
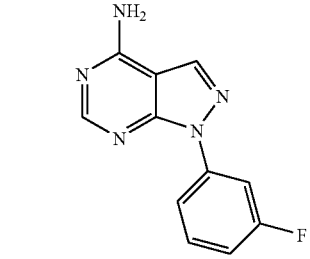

For the prophylaxis or therapy of cancer the use of the following compounds is particularly preferred:

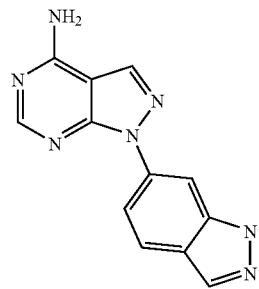
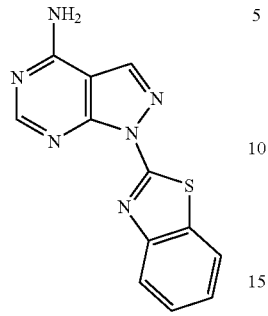
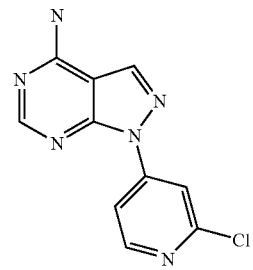
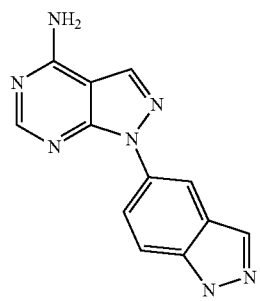
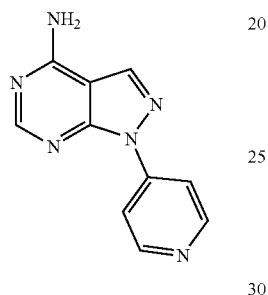
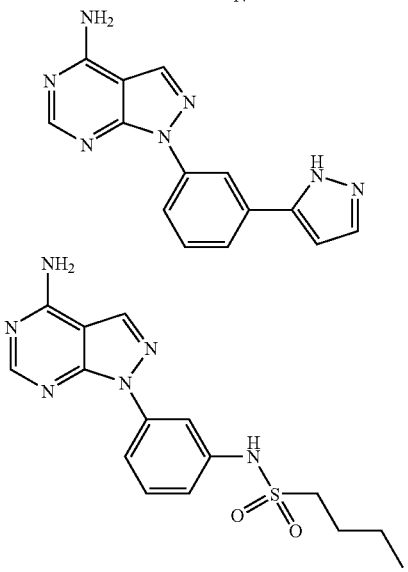
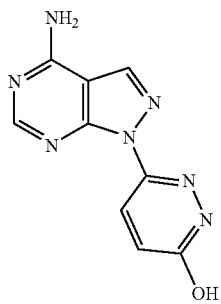
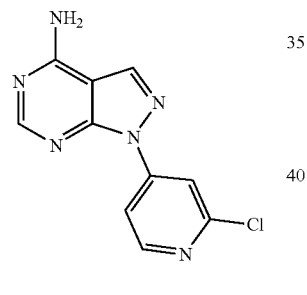
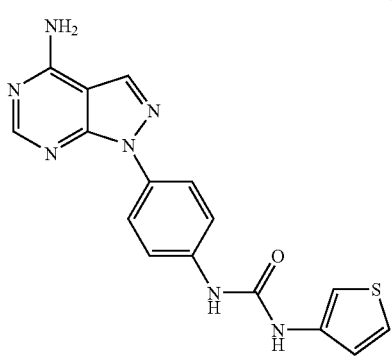
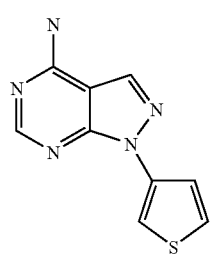
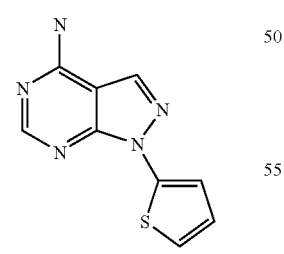
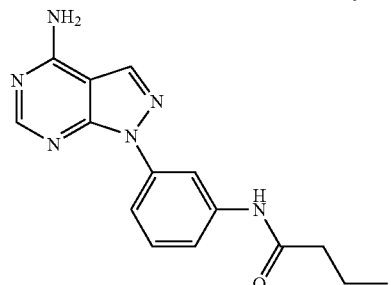
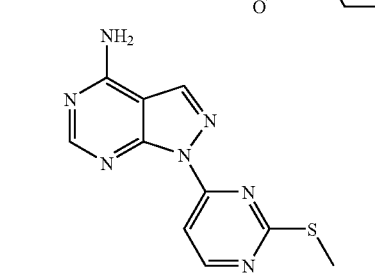

Most preferred is the use of the following pyrazolopyrimidine compounds for the preparation of a pharmaceutical composition for inhibiting the activity of the kinase activity of Mnk1 or Mnk2 (Mnk2a, Mnk2b) or variants thereof, in particular the prophylaxis or therapy of metabolic diseases and hematopoietic disorders and their consecutive complications and disease:

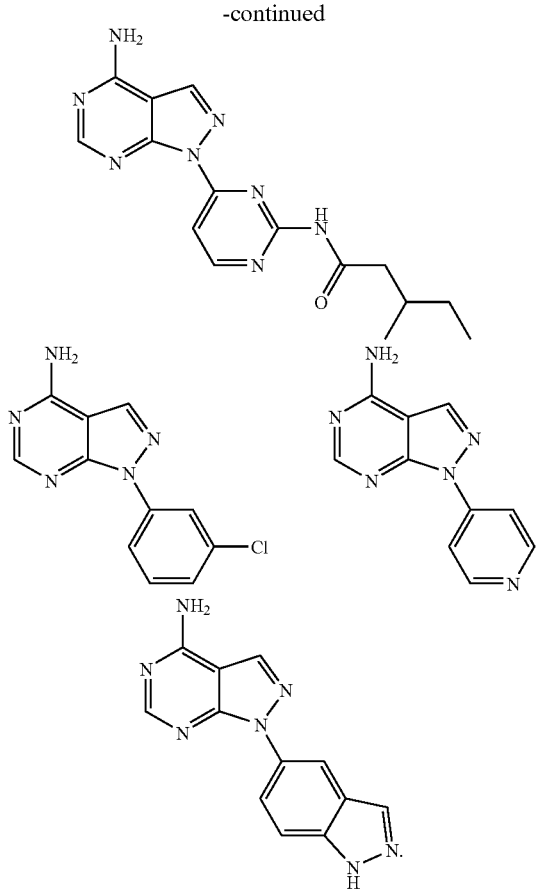

Furthermore the use of the following compounds is most preferred for the preparation of pharmaceutical compositions for the prophylaxis or therapy of cancer:

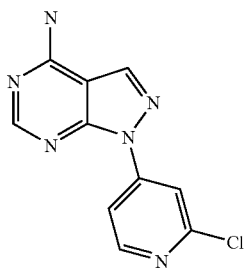

The potent inhibitory effect of the compounds of the invention may be determined by in vitro enzyme assays as described in the Examples in more detail.

Pharmaceutically acceptable salts of the compounds of the invention of formula I can be formed with numerous organic and inorganic acids and bases. Exemplary acid addition salts including acetate, adipate, alginate, ascorbate, aspartate, benzoate, benzenesulfonate, bisulphate, borate, butyrate, citrate, camphorate, camphersulfonate, cyclopentanepropionate, digluconate, dodecyl sulphate, ethane sulfonate, fumarate, glucoheptanoate, glycerophosphate, hemisulphate, heptanoate, hexanoate, hydrochloride, hydrobromide, hydroiodide, 2-hydroxyethane sulfonate, lactate, maleate, methane sulfonate, 2-naphthalene sulfonate, nicotinate, nitrate, oxalate, pamoate, pectinate, persulphate, 3-phenyl sulfonate, 3-phenylpropionate, phosphate, picrate, pivalate, propionate, salicylate, succinate, sulphate, sulfonate, tartrate, thiocyanate, toluene sulfonate such as tosylate, undecanoate, or the like.

Basic nitrogen-containing moieties can be quaternized with such agents as lower alkyl halides, such as methyl, ethyl, propyl, and butyl chloride, bromideand iodide; dialkyl sulfates like dimethyl, diethyl, dibutyl, and diamyl sulfates, long-chain alkyl halides such as decyl, lauryl, myristyl and stearyl chloride, bromide and iodide, or aralkyl halides like benzyl and phenethyl bromides, or others. Water soluble or dispersible products are thereby obtained, Pharmaceutically acceptable basic addition salts include but are not limited to cations based on the alkaline and alkaline earth metals such as sodium, lithium, potassium, calcium, magnesium, aluminium salts and the like, as well as non toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylendiamine, ethanolamine, diethanolamine, piperazine and the like and salts with amino acids such as arginie, lysine, or the like.

Compounds of the formula (I) can be present as tautomers. The present invention comprises all tautomeric forms. Furthermore, the present invention also comprises all stereoisomers of the compounds according to the invention, including its enantiomers and diastereomers. Individual stereoisomers of the compounds according to the invention can be substantially present pure of other isomers, in admixture thereof or as racemates or as selected stereoisomers.

As used herein the term "metabolite" refers to (i) a product of metabolism, including intermediate and products, (ii) any substance involved in metabolism (either as a product of metabolism or as necessary for metabolism), or (iii) any substance produced or used during metabolism. In particular it refers to the end product that remains after metabolism.

As used herein the term "prodrug" refers to (i) an inactive form of a drug that exerts its effects after metabolic processes within the body convert it to a usable or active form, or (ii) a substance that gives rise to a pharmacologically active metabolite, although not itself active (i.e. an inactive precursor).

As used herein the term "$C_3$-$C_{10}$ cycloalkyl" refers to monocyclic carbocyclic alkyl substituent or group having 3-10 ring atoms, such as cyclopropyl, cyclobutyl, cyclopentyl, cyclohexyl, cycloheptyl, cyclobutenyl, cyclopentenyl, cyclopentadienyl, cyclohexenyl, cyclohaxdienyl, cycloheptenyl, cycloheptadienyl and cycloheptatrienyl and the like;

the term "$C_4$-$C_{10}$ bicycloalkyl" refers to a bicyclic carbocyclic alkyl substituent or group having 4-10 ring atoms, such as perhydrated naphthalene or indene;

the terms "alkyl" and "alkoxy" as used herein alone or in combination with other terms refer to a $C_1$-$C_6$, preferably $C_1$-$C_4$ straight or branched alkyl/alkoxy group such as methyl, ethyl, propyl (iso-, n-), butyl (iso-, n-, tert-), pentyl, hexyl, methoxy, ethoxy, propoxy (iso-, n-), butoxy (iso-, n-, tert-), pentoxy, hexoxy;

the term "halogen" refers to a halogen atom selected from fluorine, chlorine, bromine, iodine, preferably fluorine and chlorine, more preferably fluorine;

the term "aryl" refers to monocyclic aromatic groups having 6 to 10 backbone carbon atoms, wherein optionally one of the fused cyclic structures is aromatic and the other is a carbocyclic group, such as phenyl, 1-naphthyl, 2-naphthyl, indenyl, indanyl, azulenyl, fluorenyl, 1,2,3,4-tetrahydronaphthyl;

the term "heterocyclyl" refers to monocyclic saturated or unsaturated heterocyclyl groups with 1 to 4 hetero atoms selected from N, S and O, with the remainder of the ring atoms being carbon atoms and having preferably a total number of ring atoms of 3 to 10, such as morpholino, piperazinyl, piperadinyl, pyridyl, pyrimidinyl, thiazolyl, indolyl, imidazolyl, oxadiazolyl, tetrazolyl, pyrazinyl, triazolyl, thiophenyl, furanyl;

the term "heterobicyclyl" refers to bicyclic saturated or unsaturated heterocyclyl groups with 1 to 4 hetero atoms selected from N, S and O, with the remainder of the ring atoms being carbon atoms and having preferably a total number of ring atoms of 4-10, such as indazolyl, pyrazolopyrimidyl, or quinazolyl;

the term "heteroaryl" refers to a mono- or bicyclic aromatic groups with 1 to 4 hetero atoms selected from N, S and O, with the remainder of the ring atoms being carbon atoms and having preferably a total number of ring atoms of 5 to 10. Examples without limitation of heteroaryl groups are such as benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, quinolinyl, isoquinolinyl, purinyl, carbazolyl, benzoxazolyl, benzamidazolyl, indolyl, isoindolyl, pyrazinyl, diazinyl, pyrazine, triazinyltriazine, tetrazinyl, tetrazolyl, benzothiophenyl, benzopyridyl, benzimidazolyl; and the term optionally "substituted amino" in particular refers to amino substituted with $C_1$-$C_4$ alkyl or phenyl The pharmaceutical composition according to the present invention, further may comprise an additional therapeutic agent. Particularly preferred are compositions, wherein the additional therapeutic agent is selected from antidiabetics like insulin, long and short acting insulin analogues, sulfonylureas and other antidiabetics derived from thiazolidindiones, lipid lowering agents such as statines, fibrates, ion exchange resins, nicotinic acid derivatives, or HMG-CoA reductase inhibitors, cardiovascular therapeutics such as nitrates, antihypertensive such as β-blockers, ACE inhibitors, Ca-channel blockers, angiotensin II receptor antagonists, diuretics, thrombocyte aggregation inhibitors, or antineoplastic agents such as alkaloids, alkylating agents, antibiotics, or antimetabolites.

More particularly preferred are compounds such as human NPH insulin, human lente or ultralente insulin, insulin Lispro, insulin Asptart, or insulin Glargine, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinat, acipimox, nebivolol, glycerolnitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinca alkaloids and analogues such as vinblastin, vincristin, vindesin, vinorelbin, podophyllotoxine derivatives, etoposid, teniposid, alkylating agents, nitroso ureas, N-lost analogues, cycloplonphamid, estamustin, melphalan, ifosfamid, mitoxantron, idarubicin, doxorubicin, bleomycin, mitomycin, dactinomycin, daptomycin, antimetabolites such as cytarabin, fluorouracil, fluoroarabin, gemcitabin, tioguanin, capecitabin, combinations such as adriamydin/daunorubicin, cytosine arabinosid/cytarabine, 4-HC, or other phosphamides.

It will be appreciated by the person of ordinary skill in the art that the compounds of the invention and the additional therapeutic agent may be formulated in one single dosage form, or may be present in separate dosage forms and may be either administered concomitantly (i.e. at the same time) or sequentially.

The pharmaceutical compositions of the present invention may be in any form suitable for the intended method of administration.

The compounds of the present invention may be administered orally, parenterally, such as subcutaneously, intravenously, intramuscularly, intraperitoneally, intrathecally, transdermally, transmucosally, subdurally, locally or topically via iontopheresis, sublingually, by inhalation spray, aerosol or rectally and the like in dosage unit formulations optionally comprising conventional pharmaceutically acceptable excipients.

Excipients that may be used in the formulation of the pharmaceutical compositions of the present invention comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins.

Other suitable pharmaceutically acceptable excipients are described in Remington's Pharmaceutical Sciences, $15^{th}$ Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for parentral administration include aqueous or olageous solutions or emulsions for infusion, aqueous or olageous solutions, suspensions or emulsions for injection pre-filled syringes, and/or powders for reconstitution.

Dosage forms for local/topical administration comprise insufflations, aerosols, metered aerosols, transdermal therapeutic systems, medicated patches, rectal suppositories, and/or ovula.

The amount of the compound of the present invention that may be combined with the excipients to formulate a single dosage form will vary upon the host treated and the particular mode of administration.

The pharmaceutical compositions of the invention can be produced in a manner known per se to the skilled person as described, for example, in Remington's Pharmaceutical Sciences, 15th Ed., Mack Publishing Co., New Jersey (1991).

For the purpose of the present invention, a therapeutically effective dosage will generally be from about 1 to 500 mg/day, preferably from about 10 to about 200 mg/day, and most preferably from about 10 to about 100 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgement of the ordinary clinician or physician.

EXAMPLES

Example 1

Examples of Preparation of the Compounds of the Invention

The compounds of the invention can be produced in a manner known per se as described, for example, in schemes 1 and 2 below detailing generic routes for similar analogues.

Scheme 1

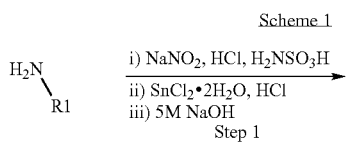

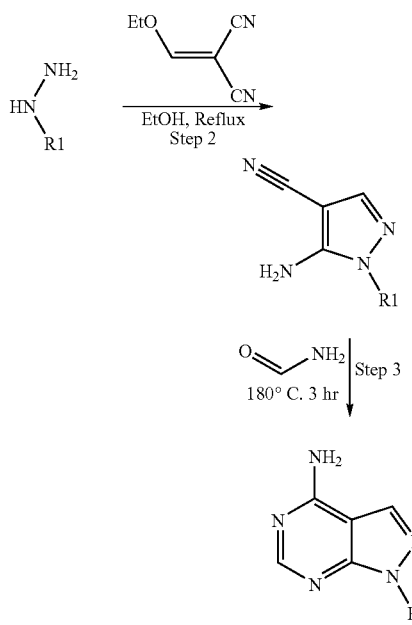

Step 1: J. Am. Chem. Soc. 1948, 70, 1381-1385; J. Med. Chem. 2003, 46, 4676-4686
Step 2: J. Med. Chem. 1997, 40, 3601
Step 3: J. Med. Chem. 1997, 40, 3601

Scheme 2

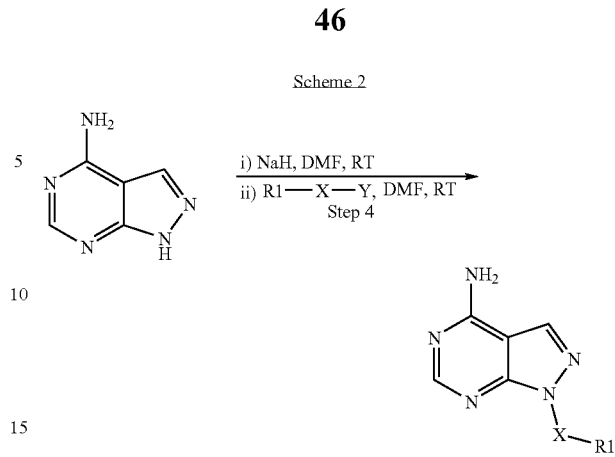

Step 4: Journal of Heterocyclic Chemistry; 1997, 34, 1, 257-262 and by the synthetic routes 1-5 exemplified below.

Example 1a

Synthesis Route 1

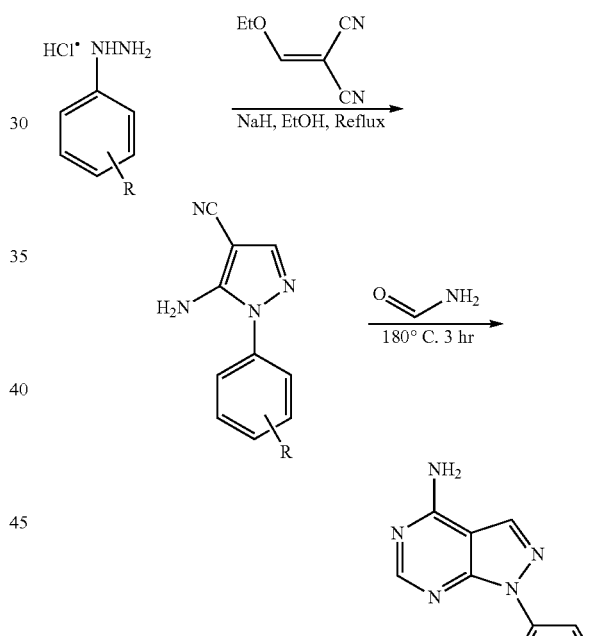

R = condensed benzo, heterocyclyl, condensed heterocyclyl, $C_1$-$C_4$ alkoxy carbonyl, carbamoyl, carboxyl, halogen selected from Cl, F, Br and I, phenyl, $C_1$-$C_4$ alkyl, alkoxy, $C_1$-$C_4$ haloalkyl, phenoxy, phenylthio, phenyl sulfonyl and $C_1$-$C_4$ alkyl carbamoyl Compound 1A. 5-Amino-1-(4-fluoro-phenyl)-1H-pyrazole-4-carbonitrile Sodium hydride as a 60% dispersion in mineral oil (5.90 g, 1.2 eq, 0.147 mol.) was added slowly to ethanol (200 ml) at room temperature. To the solution of sodium ethoxide in ethanol was added 4-fluorophenylhydrazine hydrochloride (23.96 g, 1.2 eq, 0.147 mol.), addition of ethoxymethylene malonitrile (15.00 g, 1.0 eq, 0.123 mol.) shortly followed. The reaction mixture was heated to reflux with stirring for 2 hours.

The reaction was then allowed to cool to room temperature, once at room temperature diethyl ether (50 ml) was added to the reaction mixture. The resultant precipitate was collected by filtration, washed with diethyl ether (2×100 ml) and dried in vacuo to give the title compound as a beige solid (21.5 g, 0.106 mol, 86%). LCMS: [M+H]$^+$=203, Rt=1.02 min, 100% purity.

Compound 1B. 1-(4-Fluoro-phenyl)-1H-pyrazolo[3,4-d]pyrimidin-4-ylamine

Title compound 1A, 5-amino-1-(4-fluoro-phenyl)-1H-pyrazole-4-carbonitrile (21.5 g, 0.106 mol) was suspended in formamide (200 ml). The suspension was heated to 180° C. for 3 hours and then allowed to cool to room temperature. To the reaction mixture was then added water (100 ml) and the resultant precipitate was collected by filtration, washed with water (2×100 ml), isopropyl alcohol (100 ml) and diethyl ether (100 ml), then dried on the filter to give the title compound as a beige solid (11.5 g, 55 mmol, 47%). This was then recrystalised from methanol to yield the title compound as an off-white solid (8.2 g, 35.8 mmol, 34%). LCMS: [M+H]$^+$=230, Rt=1.09 min, 100% purity.

Compound 2A. 5-Amino-1-(3-chloro-phenyl)-1H-pyrazole-4-carbonitrile

Sodium hydride as a 60% dispersion in mineral oil (0.48 g, 1.2 eq, 12 mmol) was added slowly to ethanol (20 ml) at 0° C. To the solution of sodium ethoxide in ethanol was added 3-chlorophenylhydrazine hydrochloride (1.79 g, 1.0 eq, 10 mmol), addition of ethoxymethylene malonitrile (1.22 g, 1.0 eq, 10 mmol) shortly followed. The reaction mixture was heated to reflux with stirring for 1 hour. The reaction mixture was then allowed to cool to room temperature, once at room temperature a precipitate was observed. Ethanol (20 ml) was added to the slurry and the precipitate was collected by filtration, washed with diethyl ether (2×100 ml) and dried in vacuo to give the title compound as a yellow solid (1.56 g, 7.13 mmol, 72%). LCMS: [M+H]$^+$=219, Rt=1.17 min, 100% purity.

Compound 2B. 1-(3-Chloro-phenyl)-1H-pyrazolo[3,4-d]pyrimidin-4-ylamine

Title compound 2A, 5-amino-1-(3-chloro-phenyl)-1H-pyrazole-4-carbonitrile (0.2 g, 0.91 mmol) was suspended in formamide (10 ml). The suspension was heated to 210° C. for 1 hour then allowed to cool to room temperature. To the reaction mixture was added water (10 ml), the resultant precipitate was collected by filtration, washed with water (2×10 ml) and dried on the filter. The crude solid was then purified by column chromatography with ethyl acetate/heptane (1:1) as the eluent to give the title compound as a white solid (68 mg, 0.278 mmol, 30%). LC-MS: [M+H]$^+$=246, Rt=1.06 min, 98% purity.

Compound 3A. 5-Amino-1-(3,5-dichloro-phenyl)-1H-pyrazole-4-carbonitrile

Sodium hydride as a 60% dispersion in mineral oil (0.39 g, 1.2 eq, 9.8 mmol) was added slowly to ethanol (20 ml) at 0° C. To the solution of sodium ethoxide in ethanol was added 3,5-dichlorophenylhydrazine hydrochloride (1.74 g, 1.2 eq, 9.8 mmol), addition of ethoxymethylene malonitrile (1.00 g, 1.0 eq, 8.2 mmol) shortly followed. The reaction mixture was heated to reflux with stirring for 1 hour. The reaction mixture was then allowed to cool to room temperature, once at room temperature a precipitate was observed. The precipitate was collected by filtration, washed with diethyl ether (2×20 ml) and dried in vacuo to give the title compound (0.82 g, 3.24 mmol, 40%). LCMS: [M+H]$^+$=254, Rt=0.89 min, 59% purity.

Compound 3B. 1-(3,5-Dichloro-phenyl)-1H-pyrazolo[3,4-d]pyrimidin-4-ylamine

Title compound 3A, 5-amino-1-(3,5-dichloro-phenyl)-1H-pyrazole-4-carbonitrile (0.2 g, 0.79 mmol) was suspended in formamide (5 ml). The suspension was heated to 210° C. for 2 hours then allowed to cool to room temperature. To the reaction mixture was added Water (10 ml), the resultant precipitate was collected by filtration, washed with water and dried on the filter. The crude solid was then purified by column chromatography with ethyl acetate/heptane (1:1) as the eluent to give the title compound as a white solid (3.8 mg, 0.0136 mmol, 2%). LC-MS: [M+H]$^+$=280, Rt=1.24 min, 100% purity.

Example 1b

Synthesis Route 2

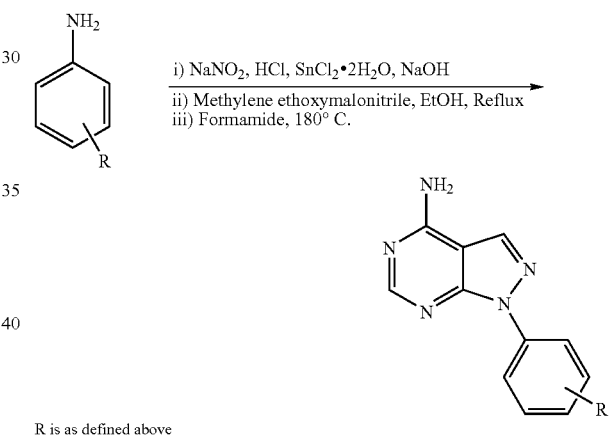

R is as defined above

Compound 4A. 1-(1H-Indazol-5-yl)-1H-pyrazolo[3,4-d]pyrimidin-4-ylamine

5-Aminoindazole (0.25 g, 1.0 eq, 1.87 mmol) was dissolved in a concentrated aqueous HCl solution (5 ml) and cooled to 0° C. To this a cooled solution of NaNO$_2$ (0.194 g, 1.5 eq, 2.82 mmol) in water (2 ml) was added over 5 minutes whilst maintaining the temperature below 10° C. The reaction was then cooled to 0° C. and stirred for a further 45 minutes. To the reaction mixture sulfamic acid (0.091 g, 0.5 eq, 0.94 mmol) was added portion wise over a 5 minute period, a solution of tin chloride dihydrate (1.26 g, 3.0 eq, 5.61 mmol) in a concentrated aqueous HCl solution (2 ml) was then added drop wise over a 10 minute period whilst maintaining the temperature below 10° C. The reaction mixture was allowed to warm to room temperature whist stirring over 2 hours. The reaction mixture was then basified to pH 14 with 5M NaOH (aq) whilst maintaining the reaction temperature below 30° C. The reaction mixture was then extracted with ethyl acetate (3×20 ml), the organics combined, washed with brine, dried over Na$_2$SO$_4$ and then solvent was removed in vacuo. The resultant orange oil was dissolved in ethanol (5 ml) and ethoxymethylene malonitrile (0.228 g, 1.0 eq, 1.87 mmol) was added. The reaction was then heated to reflux with stirring for 18 hours. The reaction was then allowed to cool to room temperature and solvent was then removed in vacuo to give an oily residue. This was then dissolved in formamide (5 ml) and heated to 180° C. for 4 hours. The reaction mixture was allowed to cool to room temperature. The resultant precipitate was collected by filtration, washed with water (2×10 ml) then dried on the filter then washed with heptane (2×10 ml) and again dried on the filter. The solid was then purified by semi-preparative HPLC to give the title compound (8.1 mg, 0.032 mmol, 2%). LC-MS: [M+H]$^+$=252, Rt=0.74 min, 100% purity.

Compound 5A. 1-(1H-Indazol-6-yl)-1H-pyrazolo[3,4-d]pyrimidin-4-ylamine

6-Aminoindazole (0.25 g, 1.0 eq, 1.87 mmol) was dissolved in a concentrated aqueous HCl solution (5 ml) and cooled to 0° C. To this a cooled solution of NaNO$_2$ (0.194 g, 1.5 eq, 2.82 mmol) in water (2 ml) was added over 5 minutes whilst maintaining the temperature below 10° C. The reaction was then cooled to 0° C. and stirred for a further 45 minutes. To the reaction mixture sulfamic acid (0.091 g, 0.5 eq, 0.94 mmol) was added portion wise over a 5 minute period, a solution of tin chloride dihydrate (1.26 g, 3.0 eq, 5.61 mmol) in a concentrated aqueous HCl solution (2 ml) was then added drop wise over a 10 minute period whilst maintaining the temperature below 15° C. The reaction mixture was allowed to warm to room temperature whist stirring over 2 hours. The reaction mixture was then basified to pH 14 with 5M NaOH (aq) whilst maintaining the reaction temperature below 30° C. The reaction mixture was then extracted with ethyl acetate (3×20 ml), the organics combined, washed with brine, dried over Na$_2$SO$_4$ and solvent removed in vacuo. The resultant orange oil was dissolved in ethanol (5 ml) and ethoxymethylene malonitrile (0.228 g, 1.0 eq, 1.87 mmol) was added. The reaction was then heated to reflux with stirring for 18 hours. The reaction was then allowed to cool to room temperature and solvent was then removed in vacuo to give an oily residue. This was then dissolved in formamide (5 ml) and heated to 180° C. for 4 hours. The reaction mixture was allowed to cool to room temperature. The resultant precipitate was collected by filtration, washed with water (2×10 ml) then dried on the filter then washed with heptane (2×10 ml) and again dried on the filter. The solid was then purified by semi-preparative HPLC to give the title compound (5.1 mg, 0.032 mmol, 1%). LC-MS: [M+H]$^+$=252, Rt=0.83 min, 100% purity.

Compound 6A. 1-[3-(3H-Imidazol-4-yl)-phenyl]-1H-pyrazolo[3,4-d]pyrimidin-4-ylamine 3-(1,3-oxazol-5-yl)aniline (0.25 g, 1.0 eq, 1.56 mmol) was dissolved in a concentrated aqueous HCl solution (5 ml) and cooled to 0° C. To this a cooled solution of NaNO$_2$ (0.161 g, 1.5 eq, 2.34 mmol) in water (2 ml) was added over 5 minutes whilst maintaining the temperature below 10° C. The reaction was then cooled to 0° C. and stirred for a further 45 minutes. To the reaction mixture sulfamic acid (0.076 g, 0.5 eq, 0.78 mmol) was added portion wise over a 5 minute period, a solution of tin chloride dihydrate (1.06 g, 3.0 eq, 4.68 mmol) in a concentrated aqueous HCl solution (2 ml) was then added drop wise over a 10 minute period whilst maintaining the temperature below 15° C. The reaction mixture was allowed to warm to room temperature over 2 hours whist stirring. The reaction mixture was then basified to pH 14 with 5M NaOH (aq) whilst maintaining the reaction temperature below 30° C. The reaction mixture was then extracted with ethyl acetate (3×20 ml), the organics combined, washed with brine, dried over Na$_2$SO$_4$ and solvent removed in vacuo. The resultant residue was dissolved in ethanol (5 ml) and ethoxymethylene malonitrile (0.19 g, 1.0 eq, 1.56 mmol) was added. The reaction was then heated to reflux with stirring for 18 hours. The reaction was then allowed to cool to room temperature and solvent was then removed in vacuo to give an oily residue. This was then dissolved in formamide (5 ml) and heated to 185° C. for 4 hours. The reaction mixture was allowed to cool to room temperature. The resultant precipitate was collected by filtration, washed with water (2×10 ml) then dried on the filter then washed with heptane (2×10 ml) and again dried on the filter. The solid was then purified by semi-preparative HPLC to give the title compound (2.0 mg, 0.0032 mmol, 0.5%). LC-MS: [M+H]$^+$=278, Rt=0.71 min, 91% purity.

Example 1c

Synthesis Route 3

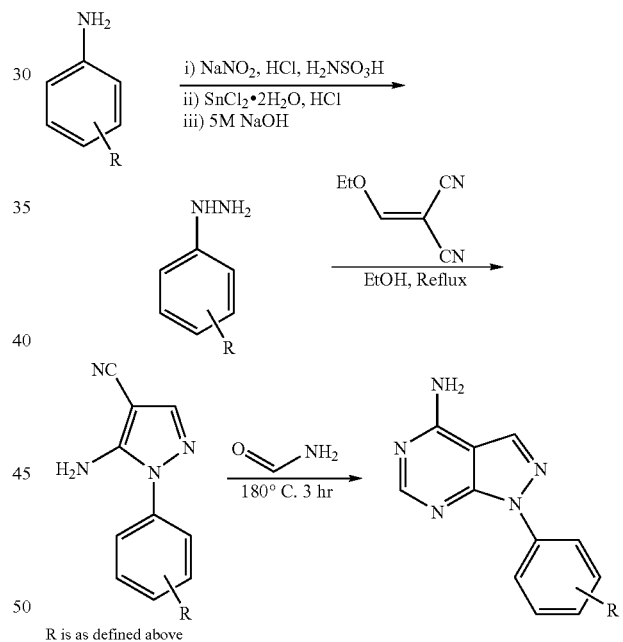

R is as defined above

Compound 7A. 4-Phenoxyhydrazine

4-Phenoxyaniline (2.0 g, 1.0 eq, 10.8 mmol) was dissolved in a concentrated aqueous HCl solution (22 ml) and cooled to 0° C. To this a cooled solution of NaNO$_2$ (1.49 g, 2.0 eq, 21.6 mmol) in water (7.6 ml) was added over 15 minutes whilst maintaining the temperature below 10° C. The reaction was then cooled to 0° C. and stirred for 1 hour. To the reaction mixture sulfamic acid (1.05 g, 1.0 eq, 10.8 mmol) was added portion wise over a 20 minute period, a solution of tin chloride dihydrate (9.78 g, 4.0 eq, 43.2 mmol) in a concentrated aqueous HCl solution (8.2 ml) was then added drop wise over a 20 minute period whilst maintaining the temperature below 15° C. The reaction mixture then stirred at 0° C. for 2 hours then basified to pH 14 with 5M NaOH (aq) whilst maintaining the reaction temperature below 30° C. The reaction mixture was then rapidly extracted with DCM (2×100 ml), the organics combined, dried over Na$_2$SO$_4$ and solvent removed in vacuo. This gave the title compound as a pale yellow solid (2.19 g, 10.9 mmol, 101%—Contains trace impurities). LC-MS: [M+H]$^+$=201, Rt=1.04 ml, 95% purity.

Compound 7B. 5-Amino-1-(4-phenoxy-phenyl)-1H-pyrazole-4-carbonitrile

4-Phenoxyhydrazine (0.171 g, 1.0 eq, 0.854 mmol) was dissolved in ethanol (4.5 ml), addition of ethoxymethylene malonitrile (0.104 g, 1.0 eq, 0.854 mmol.) shortly followed. The reaction mixture was then heated to reflux with stirring for 5 hours. The reaction mixture was then allowed to cool to room temperature and solvent was removed in vacuo. The resultant orange solid was then recrystalised from ethanol to give the title compound as a yellow solid (74 mg, 0.276 mmol, 31%). LCMS: [M+H]$^+$=277, Rt=1.35 min, 100% purity.

Compound 7C. 1-(4-phenoxy-phenyl)-1H-pyrazolo[3,4-d]pyrimidin-4-ylamine

Title compound 7B, 5-amino-1-(4-phenoxy-phenyl)-1H-pyrazole-4-carbonitrile (74 mg, 1.0 eq, 0.27 mmol) was suspended in formamide (5 ml). The suspension was heated to 210° C. for 1 hour then allowed to cool to room temperature and left to stand for 12 hours. The resultant precipitate was collected by filtration, washed with water (2×10 ml) and diethyl ether (2×5 ml) then dried in vacuo to give the title compound as a grey solid (44 mg, 0.15 mmol, 54%). LCMS: [M+H]$^+$=304, Rt=1.25 min, 100% purity.

Example 1d

Synthesis Route 4

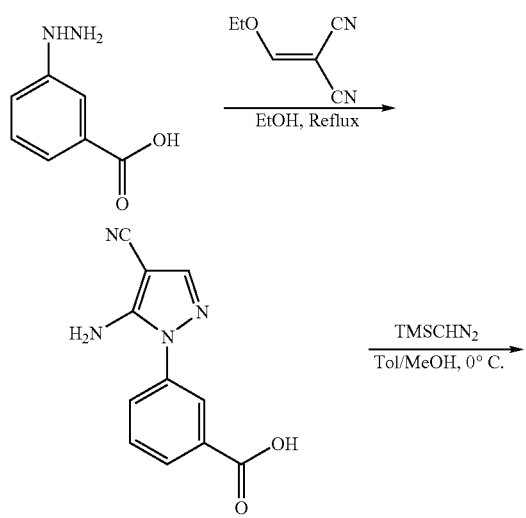

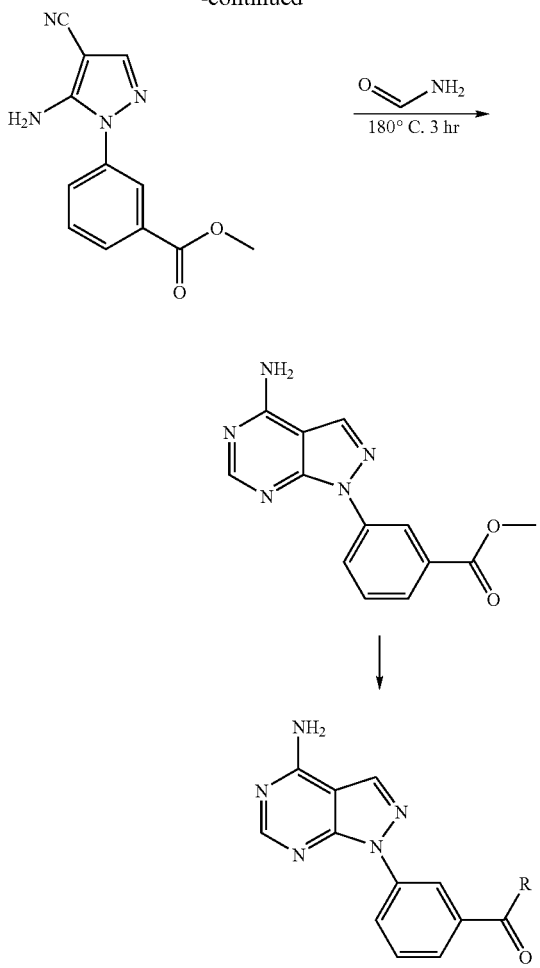

Compound 8A.
3-(5-Amino-4-cyanopyrazol-1-yl)benzoic acid

3-Hydrazinobenzoic acid (9.17 g, 1.0 eq, 60.26 mmol) was dissolved in ethanol (150 ml), addition of ethoxymethylene malonitrile (7.36 g, 1.0 eq, 60.26 mmol) shortly followed. The reaction mixture was heated to reflux with stirring for 3 hours. The reaction mixture was then allowed to cool to room temperature and the resultant precipitate was collected by filtration. The resultant orange solid was washed with ethanol (2×50 ml) and dried in vacuo to give the title compound as a yellow solid (10.4 g, 45.57 mmol, 76%). LCMS: [M+H]$^+$= 229, Rt=0.89 min, 98% purity.

Compound 8B.
3-(5-Amino-4-cyanopyrazol-1-yl)benzoic acid methyl ester

Title compound 8A, 3-(5-amino-4-cyanopyrazol-1-yl)benzoic acid (3.2 g, 1.0 eq, 14.04 mmol) was suspended in a toluene/methanol [3:1] solution (70 ml). This was then cooled to 0° C. and trimethylsilyldiazomethane was added drop wise as a 2M solution in diethyl ether (7.7 ml, 1.1 eq, 15.44 mmol).

The reaction was allowed to warm to room temperature over 2 hours. A further portion of trimethylsilyidiazomethane (1.54 ml, 0.2 eq, 2.8 mmol) was added. The reaction was stirred at room temperature for a further 45 minutes and solvent was then removed in vacuo to give the title compound as an orange solid (3.4 g, 14.04 mmol, 100%). LCMS: [M+H]$^+$=243, Rt=1.05 min, 100% purity.

Compound 8C.
3-(4-Amino-pyrazolo[3,4-d]pyrimid-1-yl)benzoic acid methyl ester

Title compound 8B, 3-(5-amino-4-cyanopyrazol-1-yl) benzoic acid (3.4 g, 1.0 eq, 14.04 mmol) was suspended in formamide (40 ml). The reaction was then heated at 170° C. with stirring for 3 hours. The reaction mixture was allowed to cool to room temperature and water (20 ml) was added to the reaction. The resultant precipitate was collected by filtration, washed with water (2×20 ml) and dried in vacuo to give the title compound as a beige solid (2.2 g, 8.12 mmol, 58%). LCMS: [M+H]$^+$=270, Rt=0.97 min, 100% purity Compound 8D.
3-(4-Amino-pyrazolo[3,4-d]pyrimid-1-yl)benzamide Title compound 8C, 3-(4-amino-pyrazolo[3,4-d]pyramid-1-yl)benzoic acid methyl ester (32 mg, 0.12 mmol) was suspended in a 28% w/w ammonium hydroxide solution (1.5 ml) and then heated to 50° C. in a sealed tube for 18 hours. The reaction mixture was then allowed to cool to room temperature and the resultant precipitate was collected by filtration, washed with water (2×5 ml) and IPA (2×5 ml) then dried in vacuo to give the title compound as a white solid (9 mg, 0.037 mmol, 31%). LCMS: [M+H]$^+$=255, Rt=0.40 min, 93% purity Compound 8E.
3-(4-Amino-pyrazolo[3,4-d]pyrimid-1-yl)benzoic acid Title compound 8C, 3-(4-amino-pyrazolo[3,4-d]pyramid-1-yl)benzoic acid methyl ester (32 mg, 0.12 mmol) was suspended in a solution of 5M NaOH (1.5 ml) and THF (1.5 ml). The reaction mixture was heated with stirring at 50° C. for 18 hours then allowed to cool. The reaction was then neutralised with 1M HCL solution and the resultant precipitate was collected by filtration. This was then washed with water (2×5 ml) and IPA (2×5 ml) before being dried in vacuo. This gave the title compound as a white solid (16 mg, 0.06 mmol, 53%). LCMS: [M+H]$^+$=256, Rt=0.60 min, 97% Purity.

Example 1e

Synthesis Route 5

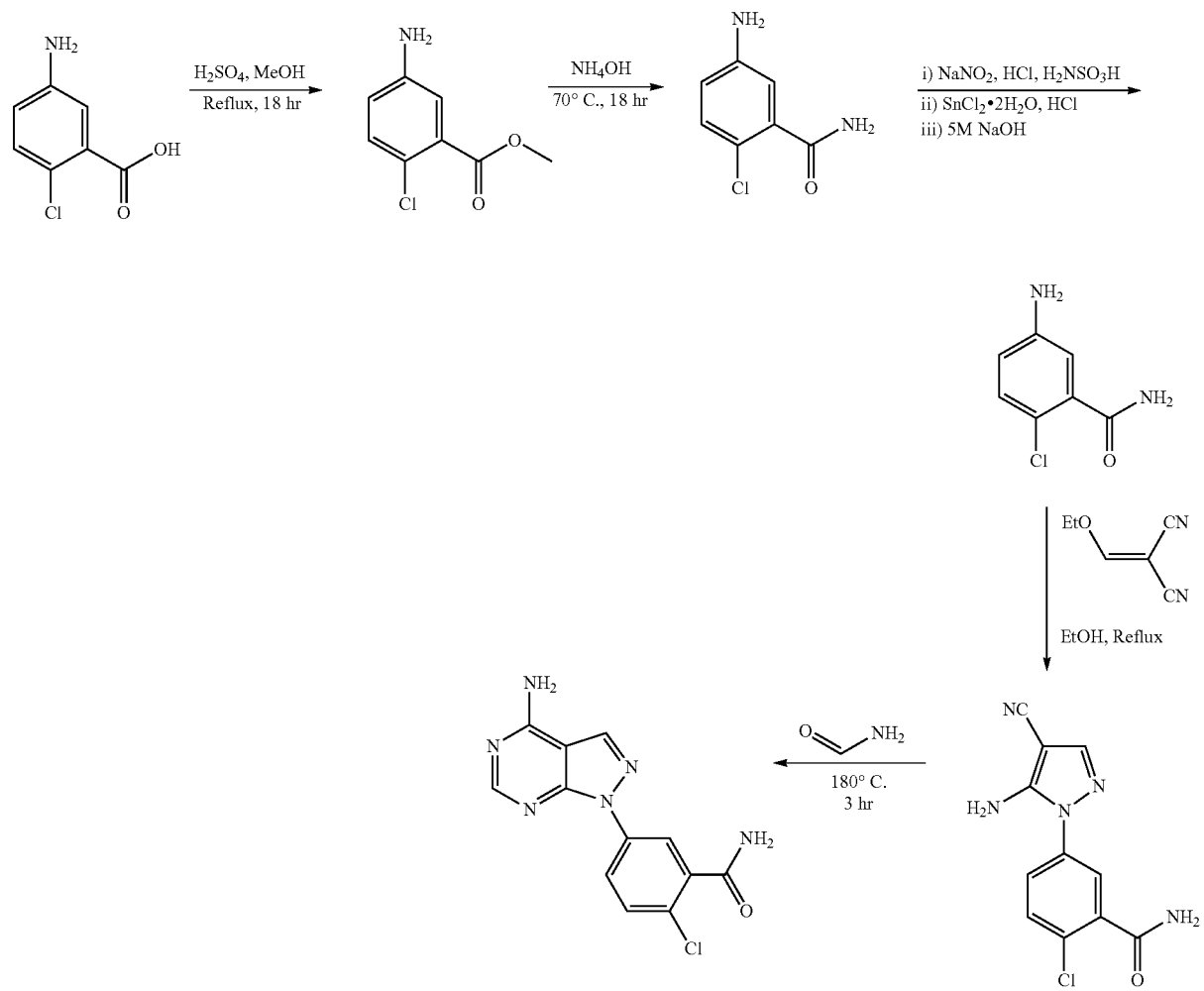

Compound 9A. 5-Amino-2-chloro-benzoic acid methyl ester

2-Chloro-5-aminobenzoic acid (1.5 g, 8.74 mmol) was dissolved in methanol (8 ml) and sulphuric acid (1 ml) was added drop wise with stirring. The reaction mixture was then heated to 86° C. for 18 hr then allowed to cool to room temperature before solvent was removed in vacuo. The resultant purple solid was then dissolved in water and 5M NaOH solution was added until pH 7 was reached. This was then washed with ethyl acetate. The organics were dried over $Na_2SO_4$ and solvent was removed in vacuo to give the title compound as a purple oil (1.51 g, 8.12 mmol, 93%): LCMS: $[M+H]^+=186$, Rt=0.88 min, 95% purity.

Compound 9B. 5-Amino-2-chloro-benzamide

Title compound 9A, 5-Amino-2-chloro-benzoic acid methyl ester (1.51 g, 8.12 mmol) was suspended in a 28% w/w $NH_4OH$ solution (5 ml) and was then stirred at 70° C. for 18 hr. The reaction mixture was concentrated to dryness under reduced pressure, and the resultant residue was purified by column chromatography using $MeOH/NH_4OH/DCM$ [10:3:87] as eluent to give the title compound (1.05 g, 6.13 mmol, 70%). LCMS: $[M+H]+=171$, Rt=0.52 min, 96% purity.

Compound 9C. 5-Hydrazino-2-chloro-benzamide

Title compound 9B, 5-amino-2-chloro-benzamide (1.05 g, 6.13 mmol) was dissolved in a concentrated aqueous solution of HCl (10 ml) and cooled to 0° C. To this a cooled solution of $NaNO_2$ (0.54 g, 1.5 eq, 9.19 mmol) in water (4 ml) was added over 15 minutes whilst maintaining the temperature below 10° C. The reaction was then cooled to 0° C. and stirred for 1 hour. To the reaction mixture sulfamic acid (0.3 g, 0.5 eq, 3.06 mmol) was added portion wise over a 20 minute period, a solution of tin chloride dihydrate (4.15 g, 3.0 eq, 18.4 mmol) in a concentrated aqueous HCl solution (4 ml) was then added drop wise over a 20 minute period whilst maintaining the temperature below 15° C. The reaction mixture then stirred at 0° C. for 2 hours then basified to pH 14 with 5M NaOH (aq) whilst maintaining the reaction temperature below 30° C. The reaction mixture was then rapidly extracted with ethyl acetate (2×50 ml), the organics combined, washed with brine, dried over $Na_2SO_4$ and solvent removed in vacuo to give the title compound (0.33 g, 1.8 mmol, 29%). LC-MS: $[M+H]^+=186$, Rt=0.53 min, 96% purity.

Compound 9D. 5-(3-Amino-4-cyano-pyrazol-1-yl)-2-chloro-benzamide

Title compound $9C_{1-5}$-hydrazino-2-chloro-benzamide (0.335 g, 1.0 eq, 1.8 mmol) was dissolved in ethanol (5 ml), addition of ethoxymethylene malonitrile (0.22 g, 1.0 eq, 1.8 mmol) shortly followed. The reaction mixture was heated to reflux with stirring for 18 hours. The reaction mixture was then allowed to cool to room temperature and solvent was removed in vacuo (0.509 g, >100%—Impurities). LCMS: $[M+H]^+=262$, Rt=0.81 min, 96% purity.

Compound 9E. 5-(4-Amino-pyrazolo[3,4-d]pyrimidin-1-yl)-2-chloro-benzamide

Title compound 9D, 5-(3-amino-4-cyano-pyrazol-1-yl)-2-chloro-benzamide (0.509 g) was dissolved in formamide (5 ml) and heated to 180° C. with stirring for 3 hours. The reaction mixture was left to cool to room temperature for 18 hours and then water (5 ml) was added. The resultant precipitate was collected by filtration, washed with water (2×20 ml) dried and then washed with heptane and dried in vacuo to give the title compound (0.34 g, 1.18 mmol, 65%). LCMS: $[M+H]^+=289$, Rt=0.95 min, 100% purity.

Example 1f

Synthesis Route 6

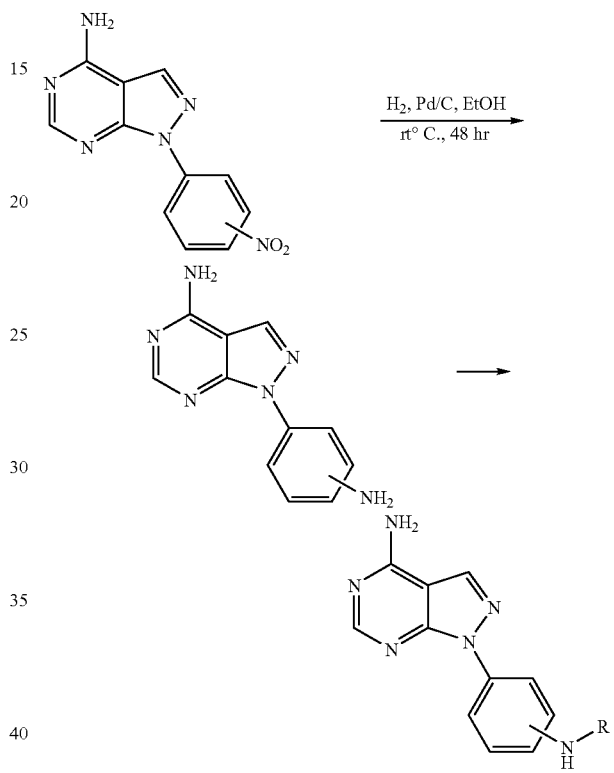

wherein R is e.g. $C(O)C_3H_7$; or as defined above

Compound 10A. 1-(4-Nitro-phenyl)-1H-pyrazolo[3,4-d]pyrimidin-4-ylamine

Title compound 10A, 1-(4-amino-phenyl)-1H-pyrazolo[3,4-d]pyrimidin-4-ylamine was prepared in a manner analogous to route 1 to yield a beige solid (1.65 g, 6.4 mmol, 74%). LCMS: $[M+H]^+=257$, Rt=1.63 min, 96% purity.

Compound 10B. 1-(3-Nitro-phenyl)-1H-pyrazolo[3,4-d]pyrimidin-4-ylamine

Title compound 10B, 1-(3-Nitro-phenyl)-1H-pyrazolo[3,4-d]pyrimidin-4-ylamine was prepared in a manner analogous to route 1 to yield a beige solid (1.4 g, 5.5 mmol, 76%). LCMS: $[M+H]^+=257$, Rt=1.61 min, 95% purity.

Compound 11A. 1-(4-Amino-phenyl)-1H-pyrazolo[3,4-d]pyrimidin-4-ylamine

Title compound 10A, 1-(4-nitro-phenyl)-1H-pyrazolo[3,4-d]pyrimidin-4-ylamine (1.0 g, 3.9 mmol) was added to 10% w/w palladium on carbon (0.1 g, 10% w/w) suspended in ethanol (300 ml). This was stirred for 42 hours at room temperature under an atmosphere of hydrogen. The reaction mixture was filtered to remove the palladium residues and the filtrate was concentrated to dryness in vacuo. The resultant residue was purified by column chromatography using DCM/MeOH (96:4) as eluent to yield the title compound as an off-white solid. (0.53 g, 2.3 mmol, 60%). LCMS: [M+H]$^+$= 227, Rt=0.64 min, 100% purity.

Compound 11B. 1-(3-Amino-phenyl)-1H-pyrazolo[3,4-d]pyrimidin-4-ylamine

Title compound 10B, 1-(3-nitro-phenyl)-1H-pyrazolo[3,4-d]pyrimidin-4-ylamine (1.0 g, 3.9 mmol) was added to 10% w/w palladium on carbon (0.1 g, 10% w/w) suspended in ethanol (300 ml). This was stirred for 42 hours at room temperature under an atmosphere of hydrogen. The reaction mixture was filtered to remove the palladium residues and the filtrate was concentrated to dryness in vacuo. The resultant residue was purified by column chromatography using DCM/MeOH (96:4) as eluent to yield the title compound as an off-white solid. (0.63 g, 2.8 mmol, 71%). LCMS: [M+H]$^+$= 227, Rt=0.71 min, 100% purity.

Compound 12A. 1N-[3-(4-Amino-pyrazolo[3,4-d]pyrimidin-1-yl)-phenyl]-butyramide

Title compound 11B, 1-(3-amino-phenyl)-1H-pyrazolo[3,4-d]pyrimidin-4-ylamine (38 mg, 1.1 eq, 0.17 mmol) was added to a solution of butyric acid (13 mg, 1.0 eq, 0.15 mmol), 1-(3-dimethylaminopropyl)-3-ethylcarbodiimide hydrochloride (26 mg, 1.1 eq, 0.17 mmol), 1-hydroxybenzotriazole (21 mg, 1.0 eq, 0.15 mmol) in DMF (1 ml) which had been stirred for 10 minutes under an inert atmosphere. The reaction was stirred at room temperature for 18 hours, after which methanol (1 ml) was added and the solvents were removed in vacuo. The resultant solid purified by semi-preparative HPLC to yield the title compound as a white solid (5.4 mg, 0.018 mmol, 12%). LCMS: [M+H]$^+$=297, Rt=1.48 min, 100% purity.

Compound 13A. N-[3-(4-Amino-pyrazolo[3,4-d]pyrimidin-1-yl)-phenyl]-3-methoxy-propionamide Title compound 11B, 1-(3-amino-phenyl)-1H-pyrazolo[3,4-d]pyrimidin-4-ylamine (37 mg, 1.1 eq, 0.16 mmol) was added to a solution of 3-methoxypropionic acid (15.5 mg, 1.0 eq, 0.15 mmol), 1-(3-dimethylaminopropyl)-3-ethylcarbodiimide hydrochloride (25 mg, 1.0 eq, 0.16 mmol), 1-hydroxybenzotriazole (20 mg, 1.0 eq, 0.15 mmol) in DMF (1 ml) which had been stirred for 10 minutes under an inert atmosphere. The reaction was stirred at room temperature for 18 hours, after which methanol (1 ml) was added, and solvent was removed in vacuo. The resultant solid was washed with water and purified by semi-preparative HPLC to yield the title compound as a white solid (5.8 mg, 0.02 mmol, 12%). LCMS: [M+H]$^+$=313, Rt=1.35 min, 100% purity.

Compound 14A. 1-[3-(4-Amino-pyrazolo[3,4-d]pyrimidin-1-yl)-phenyl]-3-isopropyl-urea Title compound 11B, 1-(3-amino-phenyl)-1H-pyrazolo[3,4-d]pyrimidin-4-ylamine (40 mg, 1.0 eq, 0.18 mmol) was dissolved in DMF (1 ml), and isopropyl isocyanate (17 µl, 1.0 eq, 0.18 mmol) was added. The reaction was then stirred at room temperature for 18 hours and methanol was added (1 ml) and the solvents were removed in vacuo. The resultant solid was washed with cold methanol and the resultant precipitate was isolated by filtration and then purified by semi-preparative HPLC to yield the title compound as a white solid (15 mg, 0.05 mmol, 27%). LCMS: [M+H]$^+$=312, Rt=1.44 min, 100% purity.

Compound 15A. N-[3-(4-Amino-pyrazolo[3,4-d]pyrimidin-1-yl)-phenyl]-4-chloro-benzenesulfonamide Title compound 11B, 1-(3-amino-phenyl)-1H-pyrazolo[3,4-d]pyrimidin-4-ylamine (40 mg, 1.1 eq, 0.18 mmol), 4-chlorobenzenesulphonylchloride (34 mg, 1.0 eq, 0.16 mmol) and diisopropylethylamine (28 µl, 1.0 eq, 0.16 mmol) were added to DMF (1 ml) and the mixture was stirred for 18 hours at room temperature under an inert atmosphere. Methanol was then added (1 ml) and the solvents were removed in vacuo. The resultant oil was purified by semi-preparative HPLC to yield the title compound as a white solid (45 mg, 0.11 mmol, 70%). LCMS: [M+H]$^+$=401, Rt=1.80 min, 100% purity.

Compound 16A. 1-Methyl-1H-imidazole-2-carboxylicacid[3-(4-amino-pyrazolo[3,4-d]pyrimidin-1-yl)-phenyl]-amide Title compound 11B, 1-(3-amino-phenyl)-1H-pyrazolo[3,4-d]pyrimidin-4-ylamine (30 mg, 1.1 eq, 0.13 mmol) was added to a solution 1-methyl-1H-imidazole-2-carboxylic acid (15 mg, 1.0 eq, 0.12 mmol), 1-(3-dimethylaminopropyl)-3-ethylcarbodiimide hydrochloride (20 mg, 1.1 eq, 0.13 mmol), 1-hydroxybenzotriazole (16 mg, 1.0 eq, 0.12 mmol) in DMF (1 ml) which had been stirred for 10 minutes under an inert atmosphere. The reaction was stirred at room temperature for 18 hours, after which methanol (1 ml) was added, and the solvents were removed in vacuo. The residue was then triturated with methanol and the resultant solid was isolated by filtration to yield the title compound as a yellow solid (3 mg, 0.01 mmol, 8%). LCMS: [M+H]$^+$=335, Rt=1.48 min, 94% purity.

Compound 17A. N N-[3-(4-Amino-pyrazolo[3,4-d]pyrimidin-1-yl)-phenyl]-4-methoxy-benzenesulfonamide Title compound 11B, 1-(3-amino-phenyl)-1H-pyrazolo[3,4-d]pyrimidin-4-ylamine (36 mg, 1.1 eq, 0.16 mmol), 4-methoxybenzenesulphonylchloride (30 mg, 1.0 eq, 0.15 mmol) and diisopropylethylamine (25 µl, 1.0 eq, 0.15 mmol) were added to DMF (1 ml) and the mixture was stirred for 15 hours at room temperature under an inert atmosphere. Methanol was then added (1 ml) and the solvents were removed in vacuo. The resultant solid was purified by semi-preparative HPLC to yield the title compound as a white solid (30 mg, 0.08 mmol, 52%). LCMS: [M+H]$^+$=397, Rt=1.68 min, 100% purity.

Compound 18A. Thiophene-2-sulfonic Acid [3-(4-amino-pyrazolo[3,4-d]pyrimidin-1-yl)-phenyl]-amide Title compound 11B, 1-(3-amino-phenyl)-1H-pyrazolo[3,4-d]pyrimidin-4-ylamine (36 mg, 1.1 eq, 0.16 mmol), 2-thiophenesulphonylchloride (29 mg, 1.0 eq, 0.16 mmol) and diisopropylethylamine (28 µl, 1.0 eq, 0.16 mmol) were added to DMF (1 ml) and the mixture was stirred for 15 hours at room temperature under an inert atmosphere. Methanol was then added (1 ml) and the solvents were removed in vacuo. The resultant residue was purified by semi-preparative HPLC to yield the title compound as a white solid (10 mg, 0.03 mmol, 16%). LCMS: [M+H]$^+$=373, Rt=1.63 min, 100% purity.

Compound 19A. 6-Phenoxy-pyridine-3-sulfonicacid [3-(4-amino-pyrazolo[3,4-d]pyrimidin-1-yl)-phenyl]-amide Title compound 11B, 1-(3-amino-phenyl)-1H-pyrazolo[3,4-d]pyrimidin-4-ylamine (36 mg, 1.1 eq, 0.16 mmol), 2-thiophenesulphonylchloride (29 mg, 1.0 eq, 0.16 mmol) and diisopropylethylamine (28 µl, 1.0 eq, 0.16 mmol) were added to DMF (1 ml) and the mixture was stirred for 15 hours at room temperature under an inert atmosphere. Methanol was then added (1 ml) and the solvents were removed in vacuo. The resultant residue was absorbed onto silica and purified by column chromatography using DCM/MeOH (96:4) as eluent to yield the title compound as a white solid (49 mg, 0.11 mmol, 80%). LCMS: [M+H]$^+$=460, Rt=1.89 min, 100% purity.

Compound 20A. 1-[3-(4-Amino-pyrazolo[3,4-d]pyrimidin-1-yl)-phenyl]-3-(2,6-dichloro-pyridin-4-yl)-urea Title compound 11B, 1-(3-amino-phenyl)-1H-pyrazolo[3,4-d]pyrimidin-4-ylamine (33 mg, 1.0 eq, 0.15 mmol) was dissolved in DMF (1 ml), and 2,6-dichloro-4-pyridyl isocyanate (28 mg, 1.0 eq, 0.15 mmol) was added. The reaction was then stirred at room temperature for 16 hours, the reaction was incomplete so a further an additional portion of 2,6-dichloro-4-pyridyl isocyanate (28 mg, 1.0 eq, 0.15 mmol) was added. The reaction was then stirred at room temperature for an additional 2.5 hours and methanol was added (1 ml) and the solvents were removed in vacuo. The resultant solid was washed with cold methanol and the resultant precipitate was isolated by filtration and washed with methanol to yield the title compound as a white solid (9.6 mg, 0.02 mmol, 16%). LCMS: [M+H]$^+$=415, Rt=1.81 min, 100% purity.

Compound 21A. 1-[3-(4-Amino-pyrazolo[3,4-d]pyrimidin-1-yl)-phenyl]-3-(2-fluoro-phenyl)-urea Title compound 11B, 1-(3-amino-phenyl)-1H-pyrazolo[3,4-d]pyrimidin-4-ylamine (40 mg, 1.0 eq, 0.18 mmol) was dissolved in DMF (1 ml), and 2-fluorophenyl isocyanate (20 µl 1.0 eq, 0.18 mmol) was added. The reaction was then stirred at room temperature for 16 hours, and methanol was added (1 ml) and the resultant precipitate was isolated by filtration and washed with methanol to yield the title compound as an off-white solid (39 mg, 0.11 mmol, 61%). LCMS: [M+H]$^+$=364, Rt=1.70 min, 100% purity.

Compound 22A. Thiophene-2-carboxylic Acid [3-(4-amino-pyrazolo[3,4-d]pyrimidin-1-yl)-phenyl]-amide Title compound 11B, 1-(3-amino-phenyl)-1H-pyrazolo[3,4-d]pyrimidin-4-ylamine (39 mg, 1.1 eq, 0.17 mmol) was added to a solution 2-thiophenecarboxylic acid (20 mg, 1.0 eq, 0.16 mmol), 1-(3-dimethylaminopropyl)-3-ethylcarbodiimide hydrochloride (27 mg, 1.1 eq, 0.17 mmol), 1-hydroxybenzotriazole (21 mg, 1.0 eq, 0.16 mmol) in DMF (1 ml) which had been stirred for 10 minutes under an inert atmosphere. The reaction was stirred at room temperature for 17 hours, after which methanol (1 ml) was added, and the solvents were removed in vacuo. The residue was then triturated with methanol and the resultant solid was isolated by filtration to yield the title compound as a pale yellow solid (6 mg, 0.02 mmol, 11%). LCMS: [M+H]$^+$=337, Rt=1.60 min, 100% purity.

Compound 23A. Thiophene-3-carboxylic acid [3-(4-amino-pyrazolo[3,4-d]pyrimidin-1-yl)-phenyl]-amide Title compound 11B, 1-(3-amino-phenyl)-1H-pyrazolo[3,4-d]pyrimidin-4-ylamine (39 mg, 1.1 eq, 0.17 mmol) was added to a solution 3-thiophenecarboxylic acid (20 mg, 1.0 eq, 0.16 mmol), 1-(3-dimethylaminopropyl)-3-ethylcarbodiimide hydrochloride (27 mg, 1.1 eq, 0.17 mmol), 1-hydroxybenzotriazole (21 mg, 1.0 eq, 0.16 mmol) in DMF (1 ml) which had been stirred for 10 minutes under an inert atmosphere. The reaction was stirred at room temperature for 17 hours, after which methanol (1 ml) was added, and the solvents were removed in vacuo. The resultant residue was absorbed onto silica and purified by column chromatography using DCM/MeOH (96:4) as eluent to yield the title compound as a white solid (10 mg, 0.03 mmol, 17%). LCMS: [M+H]$^+$=337, Rt=1.58 min, 100% purity.

Compound 24A. Thiophene-3-sulfonic acid [3-(4-amino-pyrazolo[3,4-d]pyrimidin-1-yl)-phenyl]-amide Title compound 11B, 1-(3-amino-phenyl)-1H-pyrazolo[3,4-d]pyrimidin-4-ylamine (39 mg, 1.0 eq, 0.17 mmol), 3-thiophenesulphonylchloride (31 mg, 1.0 eq, 0.17 mmol) and diisopropylethylamine (30 µl, 1.0 eq, 0.17 mmol) were added to DMF (1 ml) and the mixture was stirred for 18 hours at room temperature under an inert atmosphere. Methanol was then added (1 ml) and the solvents were removed in vacuo. The resultant residue was absorbed onto silica and purified by column chromatography using DCM/MeOH (96:4) as eluent to yield the title compound as a white solid (13 mg, 0.03 mmol, 20%). LCMS: [M+H]$^+$=373, Rt=1.60 min, 100% purity.

Compound 25A. Butane-1-sulfonic acid [3-(4-amino-pyrazolo[3,4-d]pyrimidin-1-yl)-phenyl]-amide Title compound 11B, 1-(3-amino-phenyl)-1H-pyrazolo[3,4-d]pyrimidin-4-ylamine (40 mg, 1.0 eq, 0.18 mmol), 1-butanesulphonylchloride (23 µl, 1.0 eq, 0.18 mmol) and pyridine (14 µl, 1.0 eq, 0.18 mmol) were added to DMF (1 ml) and the mixture was stirred for 42 hours at room temperature under an inert atmosphere. Methanol was then added (1 ml) and the solvents were removed in vacuo. The resultant residue was absorbed onto silica and purified by column chromatography using DCM/MeOH (96:4) as eluent to yield the title compound as a white solid (35 mg, 0.10 mmol, 57%). LCMS: [M+H]$^+$=347, Rt=1.62 min, 100% purity.

Compound 26A. 1-[3-(4-Amino-pyrazolo[3,4-d]pyrimidin-1-yl)-phenyl]-3-thiophen-3-yl-urea Title compound 11B, 1-(3-amino-phenyl)-1H-pyrazolo[3,4-d]pyrimidin-4-ylamine (30 mg, 1.0 eq, 0.13 mmol) was dissolved in DMF (1 ml), and 3-thienenyl isocyanate (16 mg, 1.0 eq, 0.13 mmol) was added. The reaction was then stirred at room temperature for 19 hours, and methanol was added (1 ml) and the solvents were removed in vacuo. The resultant residue was then triturated with MeOH, the precipitate isolated by filtration to give the title compound as an off-white solid (22 mg, 0.06 mmol, 47%). LCMS: [M+H]⁺=352, Rt=1.59 min, 97% purity.

Compound 27A. 3-Methyl-pentanoic acid [3-(4-amino-pyrazolo[3,4-d]pyrimidin-1-yl)-phenyl]-amide Title compound 11B, 1-(3-amino-phenyl)-1H-pyrazolo[3,4-d]pyrimidin-4-ylamine (40 mg, 1.1 eq, 0.18 mmol) was added to a solution 3-methylpentanoic acid (20 μl, 1.0 eq, 0.16 mmol), 1-(3-dimethylaminopropyl)-3-ethylcarbodiimide hydrochloride (27 mg, 1.1 eq, 0.18 mmol), 1-hydroxybenzotriazole (22 mg, 1.0 eq, 0.17 mmol) in DMF (1 ml) which had been stirred for 10 minutes under an inert atmosphere. The reaction was stirred at room temperature for 48 hours, after which methanol (1 ml) was added, and the solvents were removed in vacuo. The residue was purified by mass direct preparative HPLC to yield the title compound as a white solid (28 mg, 0.09 mmol, 54%). LCMS: [M+H]⁺=325, Rt=1.67 min, 100% purity.

Compound 28A. 1N-[4-(4-Amino-pyrazolo[3,4-d]pyrimidin-1-yl)-phenyl]-butyramide Title compound 11A, 1-(4-amino-phenyl)-1H-pyrazolo[3,4-d]pyrimidin-4-ylamine (38 mg, 1.1 eq, 0.17 mmol) was added to a solution of butyric acid (13 mg, 1.0 eq, 0.15 mmol), 1-(3-dimethylaminopropyl)-3-ethylcarbodiimide hydrochloride (26 mg, 1.1 eq, 0.17 mmol), 1-hydroxybenzotriazole (21 mg, 1.0 eq, 0.15 mmol) in DMF (1 ml) which had been stirred for 10 minutes under an inert atmosphere. The reaction was stirred at room temperature for 18 hours, after which methanol (1 ml) was added and the solvents were removed in vacuo. The resultant solid purified by semi-preparative HPLC to yield the title compound as a white solid (8.5 mg, 0.029 mmol, 19%). LCMS: [M+H]⁺=297, Rt=1.45 min, 100% purity.

Compound 29A. N-[4-(4-Amino-pyrazolo[3,4-d]pyrimidin-1-yl)-phenyl]-3-methoxy-propionamide Title compound 11A, 1-(4-amino-phenyl)-1H-pyrazolo[3,4-d]pyrimidin-4-ylamine (37 mg, 1.1 eq, 0.16 mmol) was added to a solution of 3-methoxypropionic acid (15.5 mg, 1.0 eq, 0.15 mmol), 1-(3-dimethylaminopropyl)-3-ethylcarbodiimide hydrochloride (25 mg, 1.0 eq, 0.16 mmol), 1-hydroxybenzotriazole (20 mg, 1.0 eq, 0.15 mmol) in DMF (1 ml) which had been stirred for 10 minutes under an inert atmosphere. The reaction was stirred at room temperature for 18 hours, after which methanol (1 ml) was added, and solvent was removed in vacuo. The resultant solid was washed with water and purified by semi-preparative HPLC to yield the title compound as a white solid (9.3 mg, 0.03 mmol, 20%). LCMS: [M+H]⁺=313, Rt=1.31 min, 100% purity.

Compound 30A. 1-[4-(4-Amino-pyrazolo[3,4-d]pyrimidin-1-yl)-phenyl]-3-isopropyl-urea Title compound 11A, 1-(4-amino-phenyl)-1H-pyrazolo[3,4-d]pyrimidin-4-ylamine (40 mg, 1.0 eq, 0.18 mmol) was dissolved in DMF (1 ml), and isopropyl isocyanate (17 μl, 1.0 eq, 0.18 mmol) was added. The reaction was then stirred at room temperature for 18 hours and methanol was added (1 ml) and the solvents were removed in vacuo. The resultant solid was washed with cold methanol and the resultant precipitate was isolated by filtration and then purified by semi-preparative HPLC to yield the title compound as a white solid (20 mg, 0.06 mmol, 36%). LCMS: [M+H]⁺=312, Rt=1.41 min, 100% purity.

Compound 31A. N-[4-(4-Amino-pyrazolo[3,4-d]pyrimidin-1-yl)-phenyl]-4-chloro-benzenesulfonamide Title compound 11A, 1-(4-amino-phenyl)-1H-pyrazolo[3,4-d]pyrimidin-4-ylamine (40 mg, 1.1 eq, 0.18 mmol), 4-chlorobenzenesulphonylchloride (34 mg, 1.0 eq, 0.16 mmol) and diisopropylethylamine (28 μl, 1.0 eq, 0.16 mmol) were added to DMF (1 ml) and the mixture was stirred for 18 hours at room temperature under an inert atmosphere. Methanol was then added (1 ml) and the solvents were removed in vacuo. The resultant oil was triturated with methanol and the resultant precipitate was isolated by filtration to yield the title compound as a white solid (21 mg, 0.05 mmol, 33%). LCMS: [M+H]⁺=401, Rt=1.76 min, 100% purity.

Compound 32A. Pyridine-2-carboxylic acid [4-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (40 mg, 1.1 eq, 0.18 mmol) was added to a solution of 2-picolinic acid (20 mg, 1.0 eq, 0.16 mmol), 1-(3-dimethylaminopropyl)-3-ethylcarbodiimide hydrochloride (28 mg, 1.0 eq, 0.18 mmol), 1-hydroxybenzotriazole (22 mg, 1.0 eq, 0.16 mmol) in DMF (1 ml) which had been stirred for 20 minutes under an inert atmosphere. The reaction was stirred at room temperature for 20 hours, after which methanol (1 ml) was added, and solvent was removed in vacuo. The resultant solid was triturated with methanol and the resultant precipitate was isolated by filtration to yield the title compound as a white solid (3.7 mg, 0.005 mmol, 7%). LCMS: [M+H]⁺=332, Rt=1.58 min, 100% purity.

Compound 33A. N-[4-(4-Amino-pyrazolo[3,4-d]pyrimidin-1-yl)-phenyl]-4-methoxy-benzenesulfonamide Title compound 11A, 1-(4-amino-phenyl)-1H-pyrazolo[3,4-d]pyrimidin-4-ylamine (36 mg, 1.1 eq, 0.16 mmol), 4-methoxybenzenesulphonylchloride (30 mg, 1.0 eq, 0.15 mmol) and diisopropylethylamine (25 μl, 1.0 eq, 0.15 mmol) were added to DMF (1 ml) and the mixture was stirred for 15 hours at room temperature under an inert atmosphere. Methanol was then added (1 ml) and the solvents were removed in vacuo. The resultant solid was purified by semi-preparative HPLC to yield the title compound as a white solid (40 mg, 0.10 mmol, 70%). LCMS: [M+H]⁺=397, Rt=1.66 min, 100% purity.

Compound 34A. Thiophene-2-sulfonic acid [4-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (36 mg, 1.1 eq, 0.16 mmol), 2-thiophenesulphonylchloride (29 mg, 1.0 eq, 0.16 mmol) and diisopropylethylamine (28 μl, 1.0 eq, 0.16 mmol) were added to DMF (1 ml) and the mixture was stirred for 15 hours at room temperature under an inert atmosphere. Methanol was then added (1 ml) and the solvents were removed in vacuo. The resultant residue was purified by semi-preparative HPLC to yield the title compound as a white solid (35 mg, 0.09 mmol, 75%). LCMS: [M+H]$^+$=373, Rt=1.60 min, 100% purity.

Compound 35A. 6-Phenoxy-pyridine-3-sulfonicacid [4-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (36 mg, 1.1 eq, 0.16 mmol), 2-thiophenesulphonylchloride (29 mg, 1.0 eq, 0.16 mmol) and diisopropylethylamine (28 µl, 1.0 eq, 0.16 mmol) were added to DMF (1 ml) and the mixture was stirred for 15 hours at room temperature under an inert atmosphere. Methanol was then added (1 ml) and the solvents were removed in vacuo. The resultant residue was absorbed onto silica and purified by column chromatography using DCM/MeOH (96:4) as eluent, followed by an additional purification by semi-preparative HPLC to yield the title compound as a white solid (17 mg, 0.11 mmol, 28%). LCMS: [M+H]$^+$=460, Rt=1.85 min, 100% purity.

Compound 36A. 1-Methyl-1H-imidazole-2-carboxylicacid[4-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (30 mg, 1.1 eq, 0.13 mmol) was added to a solution 1-methyl-1H-imidazole-2-carboxylic acid (15 mg, 1.0 eq, 0.12 mmol), 1-(3-dimethylaminopropyl)-3-ethylcarbodiimide hydrochloride (20 mg, 1.1 eq, 0.13 mmol), 1-hydroxybenzotriazole (16 mg, 1.0 eq, 0.12 mmol) in DMF (1 ml) which had been stirred for 10 minutes under an inert atmosphere. The reaction was stirred at room temperature for 18 hours, after which methanol (1 ml) was added, and the solvents were removed in vacuo. The residue was then triturated with methanol and the resultant solid was isolated by filtration to yield the title compound as a yellow solid (14 mg, 0.04 mmol, 35%). LCMS: [M+H]$^+$=335, Rt=1.44 min, 100% purity.

Compound 37A. 1-Methyl-1H-imidazole-4-sulfonic acid [4-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (33 mg, 1.0 eq, 0.15 mmol), 1-methylimidazole sulphonylchloride (22 mg, 1.0 eq, 0.15 mmol) and diisopropylethylamine (23 µl, 0.9 eq, 0.13 mmol) were added to DMF (1 ml) and the mixture was stirred for 48 hours at room temperature under an inert atmosphere. Methanol was then added (1 ml) and the solvents were removed in vacuo. The resultant residue was purified column chromatography using DCM/MeOH (96:4) as eluen followed by trituration in methanol to yield the title compound as a white solid (6 mg, 0.03 mmol, 11%). LCMS: [M+H]$^+$=371, Rt=1.33 min, 100% purity.

Compound 38A. Thiophene-3-carboxylic acid [4-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (39 mg, 1.1 eq, 0.17 mmol) was added to a solution 3-thiophenecarboxylic acid (20 mg, 1.0 eq, 0.16 mmol), 1-(3-dimethylaminopropyl)-3-ethylcarbodiimide hydrochloride (27 mg, 1.1 eq, 0.17 mmol), 1-hydroxybenzotriazole (21 mg, 1.0 eq, 0.16 mmol) in DMF (1 ml) which had been stirred for 10 minutes under an inert atmosphere. The reaction was stirred at room temperature for 17 hours, after which methanol (1 ml) was added, and the solvents were removed in vacuo. The resultant residue was triturated from methanol and the resultant precipitate was isolated by filtration to yield the title compound as a white solid (17 mg, 0.05 mmol, 29%). LCMS: [M+H]$^+$=337, Rt=1.58 min, 100% purity.

Compound 39A. 1-[4-(4-Amino-pyrazolo[3,4-d]pyrimidin-1-yl)-phenyl]-3-(2,6-dichloro-pyridin-4-yl)-urea Title compound 11A, 1-(4-amino-phenyl)-1H-pyrazolo[3,4-d]pyrimidin-4-ylamine (33 mg, 1.0 eq, 0.15 mmol) was dissolved in DMF (1 ml), and 2,6-dichloro-4-pyridyl isocyanate (28 mg, 1.0 eq, 0.15 mmol) was added. The reaction was then stirred at room temperature for 16 hours, the reaction was incomplete so a further an additional portion of 2,6-dichloro-4-pyridyl isocyanate (28 mg, 1.0 eq, 0.15 mmol) was added. The reaction was then stirred at room temperature for an additional 2.5 hours and methanol was added (1 ml) and the solvents were removed in vacuo. The resultant solid was washed with cold methanol and the resultant precipitate was isolated by filtration and washed with methanol to yield the title compound as a white solid (47 mg, 0.11 mmol, 78%). LCMS: [M+H]$^+$=415, Rt=1.77 min, 96% purity.

Compound 40A. 1-[4-(4-Amino-pyrazolo[3,4-d]pyrimidin-1-yl)-phenyl]-3-(2-fluoro-phenyl)-urea Title compound 11A, 1-(4-amino-phenyl)-1H-pyrazolo[3,4-d]pyrimidin-4-ylamine (40 mg, 1.0 eq, 0.18 mmol) was dissolved in DMF (1 ml), and 2-fluorophenyl isocyanate (20 µl, 1.0 eq, 0.18 mmol) was added. The reaction was then stirred at room temperature for 16 hours, and methanol was added (1 ml) and the resultant precipitate was isolated by filtration and washed with methanol to yield the title compound as an off-white solid (48 mg, 0.13 mmol, 75%). LCMS: [M+H]$^+$=364, Rt=1.66 min, 100% purity.

Compound 41A. Thiophene-3-sulfonic acid [4-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (39 mg, 1.0 eq, 0.17 mmol), 3-thiophenesulphonylchloride (31 mg, 1.0 eq, 0.17 mmol) and diisopropylethylamine (30 µl, 1.0 eq, 0.17 mmol) were added to DMF (1 ml) and the mixture was stirred for 18 hours at room temperature under an inert atmosphere. Methanol was then added (1 ml) and the solvents were removed in vacuo. The resultant residue was absorbed onto silica and purified by column chromatography using DCM/MeOH (96:4) as eluent to yield the title compound as a white solid (13 mg, 0.03 mmol, 20%). LCMS: [M+H]$^+$=373, Rt=1.60 min, 100% purity.

Compound 42A. Butane-1-sulfonic acid [3-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (40 mg, 1.0 eq, 0.18 mmol), 1-butanesulphonylchloride (23 µl, 1.0 eq, 0.18 mmol) and pyridine (14 µl, 1.0 eq, 0.18 mmol) were added to DMF (1 ml) and the mixture was stirred for 42 hours at room temperature under an inert atmosphere. Methanol was then added (1 ml) and the solvents were removed in vacuo. The resultant residue was absorbed onto silica and purified by column chromatography using DCM/MeOH (96:4) as eluent to yield the title compound as a white solid (27 mg, 0.08 mmol, 44%). LCMS: [M+H]$^+$=347, Rt=1.58 min, 100% purity.

Compound 43A. Thiophene-2-carboxylic acid [3-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (39 mg, 1.1 eq, 0.17 mmol) was added to a solution 2-thiophenecarboxylic acid (20 mg, 1.0 eq, 0.16 mmol), 1-(3-dimethylaminopropyl)-3-ethylcarbodiimide hydrochloride (27 mg, 1.1 eq, 0.17 mmol), 1-hydroxybenzotriazole (21 mg, 1.0 eq, 0.16 mmol) in DMF (1 ml) which had been stirred for 10 minutes under an inert atmosphere. The reaction was stirred at room temperature for 17 hours, after which methanol (1 ml) was added, and the solvents were removed in vacuo. The residue was then triturated with methanol and the resultant solid was isolated by filtration to yield the title compound as a pale yellow solid (7.3 mg, 0.02 mmol, 13%). LCMS: [M+H]$^+$=337, Rt=1.58 min, 100% purity.

Compound 44A. 1-[4-(4-Amino-pyrazolo[3,4-d]pyrimidin-1-yl)-phenyl]-3-thiophen-3-yl-urea Title compound 11A, 1-(4-amino-phenyl)-1H-pyrazolo[3,4-d]pyrimidin-4-ylamine (30 mg, 1.0 eq, 0.13 mmol) was dissolved in DMF (1 ml), and 3-thienenyl isocyanate (16 mg, 1.0 eq, 0.13 mmol) was added. The reaction was then stirred at room temperature for 19 hours, and methanol was added (1 ml) and the solvents were removed in vacuo. The resultant residue was then triturated with MeOH, the precipitate isolated by filtration to give the title compound as an off-white solid (31 mg, 0.09 mmol, 66%). LCMS: [M+H]$^+$=352, Rt=1.55 min, 100% purity.

Compound 45A. 3-Methyl-pentanoic acid [4-(4-amino-pyrazolo[3,4-d]pyrimidin-1-yl)-phenyl]-amide Title compound 11A, 1-(4-amino-phenyl)-1H-pyrazolo[3,4-d]pyrimidin-4-ylamine (40 mg, 1.1 eq, 0.18 mmol) was added to a solution 3-methylpentanoic acid (20 µl, 1.0 eq, 0.16 mmol), 1-(3-dimethylaminopropyl)-3-ethylcarbodiimide hydrochloride (27 mg, 1.1 eq, 0.18 mmol), 1-hydroxybenzotriazole (22 mg, 1.0 eq, 0.17 mmol) in DMF (1 ml) which had been stirred for 10 minutes under an inert atmosphere. The reaction was stirred at room temperature for 48 hours, after which methanol (1 ml) was added, and the solvents were removed in vacuo. The residue was purified by mass directed preparative HPLC to yield the title compound as a white solid (31 mg, 0.10 mmol, 61%). LCMS: [M+H]$^+$=325, Rt=1.64 min, 100% purity.

Example 1g

Synthesis Route 7

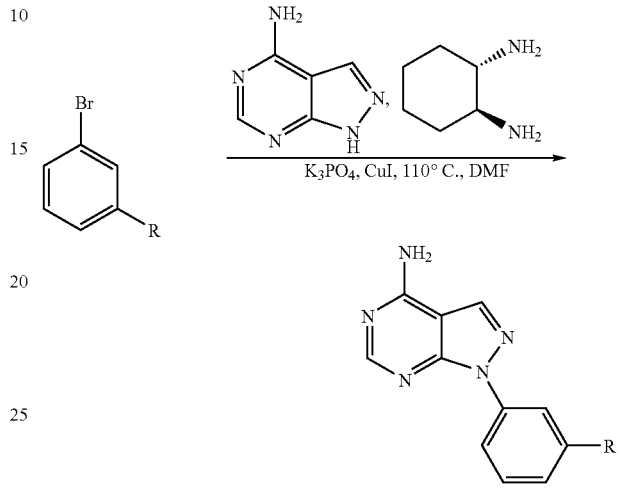

wherein R = pyrrolyl or as defined above

Compound 46A. 1-(3-Pyrrol-1-yl-phenyl)-1H-pyrazolo[3,4-d]pyrimidin-4-ylamine 1-(3-Bromo-phenyl)-1H-pyrrole (0.3 g, 1.0 eq, 1.35 mmol) and cyclohexane-1,2-diamine (0.03 g, 0.2 eq, 0.27 mmol) were added to a pre-stirred mixture of 1H-Pyrazolo[3,4-d]pyrimidine-4-ylamine (0.22 g, 1.2 eq, 1.62 mmol), copper iodide (0.013 g, 0.5 eq, 0.68 mmol) and potassium phosphate (0.6 g, 2.1 eq, 2.84 mmol) in DMF (8 ml) under an inert atmosphere. The reaction mixture was then stirred at 110° C. for 24 hours, and allowed to cool to room temperature. Ethyl acetate (8 ml) was then added to the reaction mixture which was then filtered through a plug of silica, which was then washed with a further portion of ethylacetate (20 ml). The filtrate was concentrated to dryness in vacuo and the resultant residue was purified by column chromatography using DCM/MeOH (95:5) as eluent to yield the title compound as an off-white solid (18 mg, 0.07 mmol, 5%). LCMS: [M+H]$^+$=277, Rt=1.80 min, 97% purity.

Compound 47A. 1-[3-(2H-Pyrazol-3-yl)-phenyl]-1H-pyrazolo[3,4-d]pyrimidin-4-ylamine 5-(3-bromo-phenyl)-1H-pyrazole (0.3 g, 1.0 eq, 1.34 mmol) and cyclohexane-1,2-diamine (0.03 g, 0.2 eq, 0.27 mmol) were added to a pre-stirred mixture of 1H-Pyrazolo[3,4-d]pyrimidine-4-ylamine (0.22 g, 1.2 eq, 1.62 mmol), copper iodide (0.013 g, 0.5 eq, 0.68 mmol) and potassium phosphate (0.6 g, 2.1 eq, 2.84 mmol) in DMF (8 ml) under an inert atmosphere. The reaction mixture was then stirred at 110° C. for 24 hours, and allowed to cool to room temperature. Ethyl acetate (8 ml) was then added to the reaction mixture which was then filtered through a plug of silica, which was then washed with a further portion of ethylacetate (20 ml). The filtrate was concentrated to dryness in vacuo and the resultant residue was purified by column chromatography using DCM/

MeOH (95:5) as eluent to yield the title compound as an off-white solid (0.9 mg, 0.0003 mmol, 0.2%). LCMS: [M+H]⁺=277, Rt=1.80 min, 93% purity.

Example 1h

Synthesis Route 8

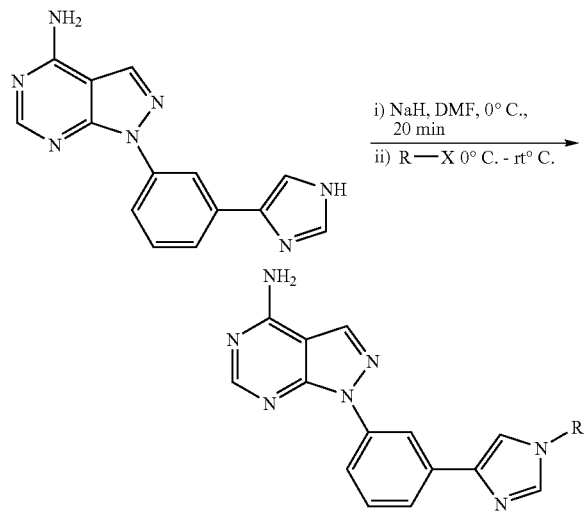

wherein R = as defined above

Compound 48A. 1-{4-[3-(4-Amino-pyrazolo[3,4-d]pyrimidin-1-yl)-phenyl]-imidazol-1-yl}-ethanone Title compound 6A, 1-[3-(3H-Imidazol-4-yl)-phenyl]-1H-pyrazolo[3,4-d]pyrimidin-4-ylamine (30 mg, 1.0 eq, 0.11 mmol) was dissolved in DMF (2 ml) and to this was added sodium hydride as a 60% dispersion in oil (5 mg, 1.1 eq, 0.12 mmol), the mixture was then stirred under an inert atmosphere for 20 minutes. To this was added acetyl chloride (7.7 μl, 1.1 eq, 0.12 mmol) the reaction was the stirred for 18 hours and allowed to warm to room temperature. Solvent was then remove in vacuo. The resultant residue was purified using mass-directed preparative HPLC to yield the compound as an off white solid (2.1 mg, 0.0007 mmol, 6%). LCMS: [M+H]⁺= 320, Rt=1.32 min, 87% purity.

Compound 48A. 1-{3-[1-(2-Methoxy-ethyl)-1H-imidazol-4-yl]-phenyl}-1H-pyrazolo[3,4-d]pyrimidin-4-ylamine Title compound 6A, 1-[3-(3H-Imidazol-4-yl)-phenyl]-1H-pyrazolo[3,4-d]pyrimidin-4-ylamine (30 mg, 1.0 eq, 0.11 mmol) was dissolved in DMF (2 ml) and to this was added sodium hydride as a 60% dispersion in oil (5 mg, 1.1 eq, 0.12 mmol), the mixture was then stirred under an inert atmosphere for 20 minutes. To this was added 1-nromo-2-methoxy-ethane (7.7 μl, 1.1 eq, 0.12 mmol) the reaction was the stirred for 18 hours and allowed to warm to room temperature. Solvent was then remove in vacuo. The resultant residue was purified using mass-directed preparative HPLC to yield the compound as an off white solid (9.9 mg, 0.003 mmol, 27%). LCMS: [M+H]⁺=336, Rt=1.22 min, 94% purity.

Example 1i

Synthesis Route 9

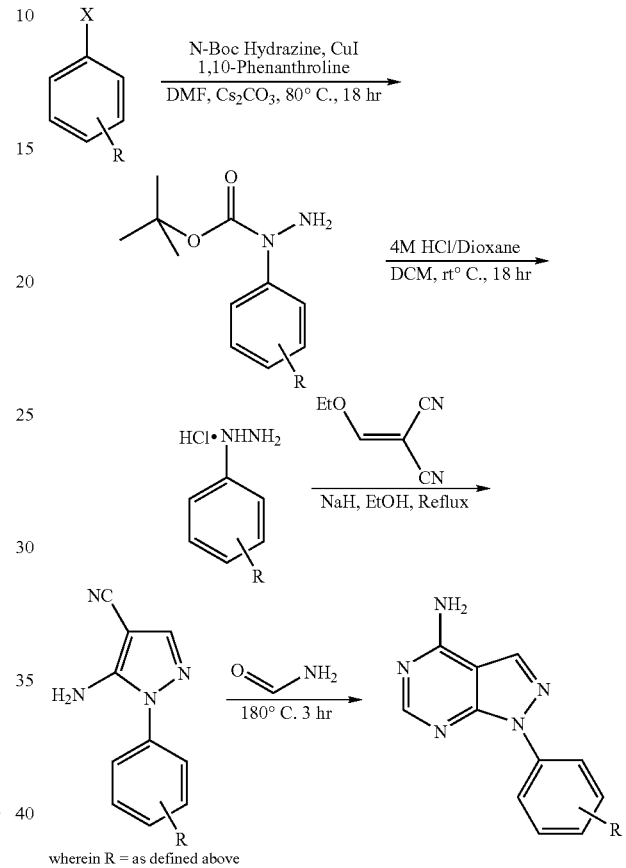

wherein R = as defined above

Compound 50A. N-(4-Pyrrol-1-yl-phenyl)-hydrazinecarboxylic acid tert-butyl ester Copper iodide (18 mg, 0.05 eq, 0.09 mmol), 1,10-phenanthroline (67 mg, 0.2 eq, 0.37 mmol) and caesium carbonate (0.85 g, 1.4 eq, 2.6 mmol) were mixed in a RB flask, placed under vacuum and purged with N₂ (g). 1-(4-iodo-phenyl)-1H-pyrrole (0.5 g, 1.0 eq, 1.86 mmol), hydrazine carboxylic acid tert-butyl ester (0.3 g, 1.2 eq, 2.23 mmol) and DMF (25 ml) were added to the mixture which was then heated to 80° C. with stirring under an inert atmosphere for 21 hours. The reaction mixture was allowed to cool and was then filtered through a silica pad, which was then washed with ethyl acetate. The filtrate was then concentrated to dryness in vacuo. The resultant residue was purified by column chromatography using heptane/ethyl acetate (3:1) as eluent to yield the title compound as an off white-solid (0.32 g, 1.16 mmol, 62%). LCMS: [M+H]⁺=274, 94% purity Compound 50B. (4-Pyrrol-1-yl-phenyl)-hydrazine hydrochloride Title compound 50A, N-(4-Pyrrol-1-yl-phenyl)-hydrazinecarboxylic acid tert-butyl ester (0.32 g, 1.0 eq, 1.2 mmol)

was suspended in a mixture of 4M HCl in Dioxane (4.9 ml, 17.0 eq, 19.7 mmol) and DCM (5 ml). The mixture was then stirred at room temperature for 24 hr solvent was then removed in vacuo to yield the title compound as an off-white solid (0.25 g, 1.12 mmol, 95%). LCMS: [M+H]$^+$=157/174, rt=0.98 min, 98% purity.

Compound 50C. 5-Amino-1-(4-pyrrol-1-yl-phenyl)-1H-pyrazole-4-carbonitrile

Sodium hydride as a 60% dispersion in mineral oil (23 mg, 1.2 eq, 0.58 mmol) was added slowly to ethanol (8 ml) at room temperature. To the solution of sodium ethoxide in ethanol was added title compound 50B, (4-Pyrrol-1-yl-phenyl)-hydrazine hydrochloride (0.1 g, 1.2 eq, 0.58 mmol), addition of ethoxymethylene malonitrile (60 mg, 1.0 eq, 0.48 mmol) shortly followed. The reaction mixture was heated to reflux with stirring for 2 hours. The reaction was then allowed to cool to room temperature, once at room temperature diethyl ether (4 ml) was added to the reaction mixture. The resultant precipitate was collected by filtration to yield the title compound as a beige solid (0.1 g, 0.4 mmol, 88%). LCMS: [M+H]$^+$=250, Rt=1.29 min, 70% purity.

Compound 50D 1-(4-Pyrrol-1-yl-phenyl)-1H-pyrazolo[3,4-d]pyrimidin-4-ylamine

Title compound 50C, 5-Amino-1-(4-pyrrol-1-yl-phenyl)-1H-pyrazole-4-carbonitrile 0.1 g, 0.4 mmol) was suspended in formamide (2 ml). The suspension was heated to 180° C. for 3 hours and then allowed to cool to room temperature. To the reaction mixture was then added water (2 ml) and the resultant precipitate was collected by filtration, and purified by column chromatography using DCM/MeOH (95:5) as eluent to yield the title compound as an off-white solid (12.6 mg, 0.05 mmol, 11%). LCMS: [M+H]$^+$=277, Rt=1.77 min, 100% purity.

Compound 51A.
N-(4-Pyrazol-1-yl-phenyl)-hydrazinecarboxylic acid tert-butyl ester Copper iodide (18 mg, 0.05 eq, 0.09 mmol), 1,10-phenanthroline (67 mg, 0.2 eq, 0.37 mmol) and caesium carbonate (0.84 g, 1.4 eq, 2.6 mmol) were mixed in a RB flask, placed under vacuum and purged with N$_2$ (g). 1-(4-Iodo-phenyl)-1H-pyrazole (0.5 g, 1.0 eq, 1.85 mmol), hydrazine carboxylic acid tert-butyl ester (0.3 g, 1.2 eq, 2.22 mmol) and DMF (25 ml) were added to the mixture which was then heated to 80° C. with stirring under an inert atmosphere for 21 hours. The reaction mixture was allowed to cool and was then filtered through a silica pad, which was then washed with ethyl acetate. The filtrate was then concentrated to dryness in vacuo. The resultant residue was purified by column chromatography using heptane/ethyl acetate (3:1) as eluent to yield impure title compound (0.42 g). LCMS: [M+H]$^+$=275, rt=1.25 min, 48% purity.

Compound 51B. (4-Pyrazol-1-yl-phenyl)-hydrazine hydrochloride

Title compound 51A, N-(4-Pyrazol-1-yl-phenyl)-hydrazinecarboxylic acid tert-butyl ester (0.42 g, 1.0 eq, 1.53 mmol) was suspended in a mixture of 4M HCl in Dioxane (6.5 ml, 17.0 eq, 26 mmol) and DCM (5 ml). The mixture was then stirred at room temperature for 24 hours solvent was then removed in vacuo to yield impure title compound. (0.31 g). LCMS: [M+H]$^+$=158/175, 65% purity.

Compound 51C. 5-Amino-1-(4-pyrazol-1-yl-phenyl)-1H-pyrazole-4-carbonitrile

Sodium hydride as a 60% dispersion in mineral oil (23 mg, 1.2 eq, 0.57 mmol) was added slowly to ethanol (8 ml) at room temperature. To the solution of sodium ethoxide in ethanol was added title compound 51B, 4-Pyrazol-1-yl-phenyl)-hydrazine hydrochloride (0.1 g, 1.2 eq, 0.57 mmol), addition of ethoxymethylene malonitrile (58 mg, 1.0 eq, 0.48 mmol) shortly followed. The reaction mixture was heated to reflux with stirring for 2 hours. The reaction was then allowed to cool to room temperature and solvent was removed in vacuo. The resultant solid was triturated with diethyl ether and the results solid was removed by filtration. The filtrate was concentrated to dryness in vacuo to yield impure title compound (0.051 g). LCMS: [M+H]$^+$=251, 61% purity.

Compound 51D 1-(4-Pyrazol-1-yl-phenyl)-1H-pyrazolo[3,4-d]pyrimidin-4-ylamine

Title compound 51C, 5-Amino-1-(4-pyrazol-1-yl-phenyl)-1H-pyrazole-4-carbonitrile (0.051 g, 0.2 mmol) was suspended in formamide (2 ml). The suspension was heated to 180° C. for 3 hours and then allowed to cool to room temperature. To the reaction mixture was then added water (2 ml) and the resultant precipitate was collected by filtration, and purified by column chromatography using DCM/MeOH (95:5) as eluent to yield the title compound as an off-white solid (3.2 mg, 0.001 mmol, 6%). LCMS: [M+H]$^+$=278, Rt=1.54 min, 100% purity.

52A. N-(4-Cyano-phenyl)-hydrazinecarboxylic acid tert-butyl ester

Copper iodide (18 mg, 0.05 eq, 0.09 mmol), 1,10-phenanthroline (67 mg, 0.2 eq, 0.37 mmol) and caesium carbonate (0.84 g, 1.4 eq, 2.6 mmol) were mixed in a RB flask, placed under vacuum and purged with N$_2$ (g). 4-iodo-benzonitrile (0.5 g, 1.0 eq, 1.85 mmol), hydrazine carboxylic acid tert-butyl ester (0.3 g, 1.2 eq, 2.22 mmol) and DMF (25 ml) were added to the mixture which was then heated to 80° C. with stirring under an inert atmosphere for 16 hours. The reaction mixture was allowed to cool and the solvent was removed in vacuo. The resultant residue was absorbed onto silica and purified by column chromatography using heptane/ethyl acetate (7:3) as eluent to yield the title compound as a pale orange solid (0.23 g, 1.0 mmol, 45%). LCMS: [M+H]$^+$=234, rt=1.94 min, 97% purity.

Compound 52B. 4-Hydrazino-benzonitrile hydrochloride

Title compound 52A, N-(4-cyano-phenyl)-hydrazinecarboxylic acid tert-butyl ester (0.23 g, 1.0 eq, 0.99 mmol) was suspended in a mixture of 4M HCl in Dioxane (4.2 ml, 17.0 eq, 16.8 mmol) and DCM (5 ml). The mixture was then stirred at room temperature for 18 hours The resultant precipitate was isolated by filtration and washed with DCM to yield the title compound as a cream solid. (0.14 g, 0.8 mmol, 85%). $^1$H NMR (DMSO) 400 MHz: Indicates product in >95% purity Compound 52C. 5-Amino-1-(4-cyano-phenyl)-1H-pyrazole-4-carbonitrile The title compound 52B, 4-hydrazino-benzonitrile hydrochloride (0.134 g, 1.0 eq, 0.8 mmol) was dissolved in ethanol (2 ml) and to this was added 21% w/w sodium ethoxide in ethanol (0.3 ml, 1.0 eq, 0.8 mmol). Ethoxymethylene malonitrile (98 mg, 1.0 eq, 0.48 mmol) was then added and the reaction mixture was heated to reflux with stirring for 2 hours. The reaction was then allowed to cool to room temperature and the resultant solid was isolated by filtration and washed with ethanol to yield the title compound as a cream solid (0.11 g, 5.3 mmol, 67%). LCMS: [M+H]$^+$=210, Rt=1.52 min, 100% purity.

Compound 52D 14-(4-Amino-pyrazolo[3,4-d]pyrimidin-1-yl)-benzonitrile

Title compound 52C, 5-Amino-1-(4-pyrazol-1-yl-phenyl)-1H-pyrazole-4-carbonitrile (0.05 g, 0.24 mmol) was suspended in formamide (1 ml). The suspension was heated to 180° C. for 3.5 hours and then allowed to cool to room temperature. To the reaction mixture was then added water (2 ml) and the resultant precipitate was collected by filtration and washed with water to yield the title compound as an off-white solid (22 mg, 0.09 mmol, 37%). LCMS: [M+H]$^+$=237, Rt=1.44 min, 95% purity.

Example 2

Kinase Fluorescence Polarization Assays

Assay principle: Inhibitory potency of compounds against Mnk1, Mnk2a and other kinases was assessed with assays based on a format known to those skilled in the art as the indirect (competitive) fluorescence polarization. The assay detection system comprises a small fluorophore-labeled phospho-peptide (termed ligand) bound to a phospho-specific antibody. The product generated by the kinase reaction competes with the ligand for antibody binding. Based on the larger molecular volume of the bound ligand, which results in a lower rotation rate in solution, its emitted light has a higher degree of polarization than the one from the free ligand. Description of the Specific Homogenous Kinase Assay Example 2a Mnk1 and Mnk2a in vitro Kinase Assay As a source of enzyme, human Mnk1 and human Mnk2a were expressed as GST fusion proteins in E. coli, purified to >80% homogeneity by glutathione affinity chromatography and activated in vitro with pre-activated ERK2. In brief, the open reading frames of human Mnk1 and Mnk2a were amplified from cDNA using the forward/reverse primer pairs

```
5'TTTAGGATCCGTATCTTCTCAAAAGTTGG /    SEQ ID NO: 1

5' CTGGGTCGACTCAGAGTGCTGTGGGCGG      SEQ ID NO: 2
and

5'ACAGGGATCCGTGCAGAAGAAACCAGCC /    SEQ ID NO: 3

5'GATGGTCGACTCAGGCGTGGTCTCCCACC     SEQ ID NO: 4
```

(utilized restriction sites underlined), respectively, and cloned into the BamHI and SalI sites of the vector pGEX-4T1 (Amersham, Sweden, cat. no. 274580-01). These constructs allow prokaryotic expression of Mnk1 or Mnk2a as fusion protein with a N-terminal glutathione S-transferase (GST) tag, referred to as GST-Mnk1 or GST-Mnk2a. The following expression and purification procedure was identical for GST-Mnk1 and GST-Mnk2a, referring in general to GST-Mnk, when not distinguishing between the two isoforms. Expression of GST-Mnk was in E. coli BL21 (Merck Biosciences, Germany, cat. no. 69449). Cells were grown in LB-Bouillon (Merck, Germany, cat. no. 1.10285) supplemented with 100 μg/ml ampicillin (Sigma, Germany, cat. no. A9518) at 37° C. When the culture had reached a density corresponding to an $A_{600}$ of 0.8, an equal volume of ice cold LB/ampicillin was added, the culture transferred to 25° C. and induced for 4 h with 1 mM isopropyl thiogalactoside (IPTG, Roth, Germany, cat. no. 2316.4). Cells harvested by centrifugation were resuspended in 10 ml lysis buffer (50 mM tris(hydroxymethyl)aminomethane hydrochloride (Tris/HCl, Sigma, Germany, cat. no. T5941) pH 7.5, 300 mM sodium chloride (NaCl, Sigma, Germany, cat. no. S7653), 5% (w/v) glycerol (Sigma, Germany, cat. no. G5516), 3 mM DTT dithiotreitol (DTT, Sigma, Germany, cat. no. D9779)) per gram wet weight cell pellet. Lysates were prepared by disruption of cells with a sonifier and subsequent clearing by centrifugation at 38000 g for 45 min at 4° C.

The lysate was applied to a GSTPrep FF 16/10 column (Amersham, Sweden, cat. no. 17-5234-01) equilibrated with lysis buffer. Removal of unbound material was with 3 column volumes (CV) lysis buffer. Elution was with 2 CV of elution buffer (50 mM Tris/HCl pH 7.5, 300 mM NaCl, 5% (w/v) glycerol, 20 mM glutathione (Sigma, Germany, cat. no. G4251)). Peak fractions were pooled and the protein transferred into storage buffer (50 mM Tris/HCl pH 7.5, 200 mM NaCl, 0.1 mM ethylene glycol-bis(2-aminoethylether)-N,N,N',N'-tetraacetic acid (EGTA, Aldrich, Germany, cat. no. 23, 453-2), 1 mM DTT, 10% (w/v) glycerol, 0.5 M sucrose (Sigma, Germany, cat. no. S0389) by gel filtration on a PD10 desalting column (Amersham, Sweden, cat. no. 17-0851-01). Aliquots were shock frozen in liquid nitrogen and stored at −80° C.

Activation of Mnk1 and Mnk2a was at a concentration of 2.5 μM of either purified GST-Mnk1 or GST-Mnk2a by incubation with 150 μM pre-activated NHis-ERK2 (see ERK2 assay for preparation) and 50 μM adenosine triphosphate (ATP, Sigma, cat. no. A2699) in a buffer comprising 20 mM N-(2-hydroxyethyl)piperazine-N'-(2-ethanesulfonic acid) (HEPES, Fluka, Germany, cat. no 54459)/potassium hydroxide (KOH, Roth, Germany, cat. no 6751.1) pH 7.4, 10 mM magnesium chloride ($MgCl_2$, Sigma, Germany, cat. no. M2670), 0.25 mM DTT, 0.05% (w/v) polyoxyethylene 20 stearylether (Brij 78, Sigma, Germany, cat. no. P4019) (HMDB buffer) for 45 min at 30° C. After the incubation, the preparation was aliquoted into single-use samples, shock frozen in liquid nitrogen, stored at −80° C. and utilized for Mnk1 or Mnk2a kinase assays as detailed below. The presence of activating kinase has been tested to not interfere with the Mnk activity assay.

SUBSTRATE: A carboxy-terminal amidated 12mer peptide with the sequence SEQ ID NO: 5 TATKSGSTTKNR, derived from the amino acid sequence around serine 209 of the eukaryotic translation initiation factor 4E (eIF4E) has been synthesized and purified by high performance liquid chromatography (HPLC) to >95% (Thermo, Germany). The serine residue phosphorylated by Mnk kinases is underlined.

LIGAND: The peptide TATKSG-pS-TTKNR, containing an amidated carboxy-terminus and conjugated at the amino-terminus with the oxazine derived fluorophore depicted below was synthesized and used as ligand.

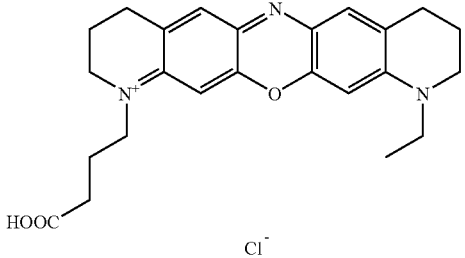

ANTIBODY: SPF New Zealand White Rabbits have been immunized according to standard protocols with the peptide NH2-CTATKSG-pS-TTKNR-CONH2, coupled to keyhole limpet hemocyanin (KLH). The immune globulin G (IgG) fraction was purified from serum of boosted animals by techniques known in the art. In brief, serum was subjected to protein A affinity chromatography. Eluted material was precipitated at 50% cold saturated ammonium sulfate, pellets dissolved and desalted. The resulting material was appropriate for use in below described assay without further antigen-specific purification.

ASSAY SETUP: Inhibition of kinase activity of Mnk1 and Mnk2a was assessed with the same assay system, using pre-activated GST-Mnk1 or GST-Mnk2a, respectively. The kinase reaction contains 30 µM substrate peptide, 20 µM ATP, 60 nM ligand and one of either 25 nM pre-activated Mnk1 or 2.5 nM pre-activated Mnk2a. The reaction buffer conditions are 16 mM HEPES/KOH pH 7.4, 8 mM MgCl$_2$, 0.4 mM DTT, 0.08% (w/v) bovine serum albumin (BSA, Sigma, Germany, cat. no. A3059), 0.008% (w/v) Pluronic F127 (Sigma, Germany, cat. no. P2443), 3% (v/v) DMSO (Applichem, Germany, cat. no. A3006). The kinase reaction is at 30° C. for 40 min. The kinase reaction is terminated by addition of 0.67 reaction volumes of 1 µM antibody in 20 mM HEPES/KOH pH 7.4, 50 mM ethylenediaminetetraacetic acid, disodium salt (EDTA, Sigma, Germany, cat. no. E5134), 0.5 mM DTT, 0.05% (w/v) polyoxyethylene-sorbitan monolaureate (Tween 20, Sigma, Germany, cat. no. P7949). After 1 h equilibration time at room temperature, samples are subjected to fluorescence polarization measurement. The fluorescence polarization readout was generated on an Analyst AD multimode reader (Molecular Devices, Sunnyvale, Calif., USA) equipped with a DLRP650 dichroic mirror (Omega Opticals, Brattleboro, Vt., USA, cat. no. XF2035), a 630AF50 band pass filter (Omega Opticals, Brattleboro, Vt., USA, cat. no. XF1069) on the excitation and a 695AF55 band pass filter on the emission side (Omega Opticals, Brattleboro, Vt., USA, cat. no. XF3076).

Example 2b

ERK2 in vitro Kinase Assay

KINASE: As a source of enzyme, human ERK2 was expressed as N-terminal hexa-histidin fusion protein in *E. coli*, purified to >80% homogeneity by immobilized metal ion affinity chromatography (IMAC) and activated in vitro with a constitutively active mutant of MEK1.

In brief, the open reading frame of human ERK2 was amplified from cDNA using the forward/reverse primer pair 5' AGCC<u>GTCGAC</u>GCGGCGGCGGCGGCGGCGGGC / SEQ ID NO: 6

5' TGAC<u>AAGCTT</u>AAGATCTGTATCCTGGCTGG SEQ ID NO: 7

(utilized restriction sites underlined) and cloned into the SalI and HindIII sites of the vector pQE81L (Qiagen, Germany, cat. no. 32923). This construct allows prokaryotic expression of ERK2 as fusion protein with a N-terminal hexa-histidin tag, referred to as NHis-ERK2.

Expression of NHis-ERK2 was in *E. coli* BL21. Cells were grown in LB-Bouillon supplemented with 100 µg/ml ampicillin at 37° C. When the culture had reached a density corresponding to an A$_{600}$ of 0.8, an equal volume of ice cold LB/ampicillin was added, the culture transferred to 25° C. and induced for 4 h with 1 mM IPTG. Cells harvested by centrifugation were resuspended in 10 ml lysis buffer (50 mM Tris/HCl pH 7.5, 300 mM NaCl, 5% (w/v) glycerol, 10 mM β-mercapto ethanol (Sigma, Germany, cat. no. M3148) per gram wet weight cell pellet. Lysates were prepared by disruption of cells with a sonifier and subsequent clearing by centrifugation at 38000 g for 45 min at 4° C.

The lysate was applied to a column containing 25 ml Ni-NTA Superflow matrix (Qiagen, Germany, cat. no. 1018611) equilibrated with lysis buffer. Removal of unbound material was with 3 column volumes (CV) wash buffer (50 mM Tris/HCl pH 7.5, 300 mM NaCl, 5% (w/v) glycerol, 10 mM β-mercapto ethanol, 20 mM imidazol (Sigma, Germany, cat. no. 12399)/HCl pH 7.5). Elution was with 2 CV of elution buffer (50 mM Tris/HCl pH 7.5, 300 mM NaCl, 5% (w/v) glycerol, 300 mM imidazol). Peak fractions were pooled and the protein transferred into storage buffer (50 mM Tris/HCl pH 7.5, 200 mM NaCl, 0.1 mM EGTA, 1 mM DTT, 10% (w/v) glycerol, 0.5 M sucrose) by gel filtration on a PD10 desalting column. Aliquots were shock frozen in liquid nitrogen and stored at −80° C.

The open reading frame of human MEK1 was amplified from cDNA using the forward/reverse primer pair 5' GTCC<u>GGATCC</u>CCCAAGAAGAAGCCGACGCCC SEQ ID NO: 8

5' TCCC<u>GTCGAC</u>TTAGACGCCAGCAGCATGGG SEQ ID NO: 9

(utilized restriction sites underlined) and cloned into the BamHI and SalI sites of the vector pQE80L (Qiagen, Germany, cat. no. 32923). By techniques known in the art, the serine codons 212 and 214 were mutagenized to encode aspartate and glutamate. The resulting expression construct is referred to as NHis-MEK1 SSDE. This construct allows prokaryotic expression of MEK1 as a constitutively active mutant. NHis-MEK1 SSDE was expressed and purified under the conditions described for NHis-ERK2.

Activation of NHis-ERK2 was at a concentration of 11.3 µM of purified enzyme by incubation with 1 µM NHis-MEK1 SSDE and 100 µM ATP in a buffer comprising 20 mM HEPES/KOH pH 7.4, 10 mM MgCl$_2$, 0.25 mM DTT, 0.05% (w/v) Brij 78 (HMDB buffer) for 20 min at 30° C. After the incubation, the preparation was aliquoted into single-use samples, shock frozen in liquid nitrogen, stored at −80° C. and utilized for ERK2 kinase assay as detailed below and for activation of Mnk1 and Mnk2a as described above. The presence of MEK1 SSDE has been tested to not interfere with the ERK2 activity assay.

SUBSTRATE: A carboxy-terminal amidated 17mer peptide with the sequence SEQ ID NO:10 FFKNIV TPRTPPPSQGK (synthesis by Thermo, Germany), derived from the amino acid sequence around threonine 98 of the myelin basic protein (MBP) has been synthesized and purified by HPLC to >95%. The relevant residue phosphorylated by ERK2 is underlined.

LIGAND: The peptide KNIVTPR-pT-PPPS, containing an amidated carboxy-terminus and conjugated at the amino-terminus with the fluorophore 5-carboxytetramethyl-rhodamine (5-TAMRA) was purchased from Thermo (Germany) and used as ligand.

ANTIBODY: Anti-phospho-MBP antibody (clone P12) was purchased from Upstate, Waltham, Mass., USA (cat. no. 05-429).

ASSAY SETUP: The kinase reaction contains 60 μM substrate peptide, 10 μM ATP and 30 nM pre-activated NHis-ERK2. The reaction buffer conditions are 16 mM HEPES/KOH pH 7.4, 8 mM $MgCl_2$, 0.4 mM DTT, 0.08% (w/v) BSA, 0.008% (w/v) Pluronic F127, 3% (v/v) DMSO.

The kinase reaction is at 30° C. for 40 min. The kinase reaction is terminated by addition of 0.67 reaction volumes of 5 nM ligand and 50 nM antibody in 20 mM HEPES/KOH pH 7.4, 50 mM EDTA, 0.5 mM DTT, 0.05% (w/v) Tween 20. After 30 min equilibration time at room temperature, samples are subjected to fluorescence polarization measurement. The fluorescence polarization readout was generated on an Analyst AD multimode reader (Molecular Devices, Sunnyvale, Calif., USA) equipped with a 561 nm dichroic mirror (Molecular Devices, Sunnyvale, Calif., USA, cat. no. 42-000-0048), a 550/10 nm band pass filter (Molecular Devices, Sunnyvale, Calif., USA, cat. no. 42-000-0130) on the excitation and a 580/10 nm band pass filter (Molecular Devices, Sunnyvale, Calif., USA, cat. no. 42-000-0034) on the emission side.

Example 2c

MAPKAP-K2 in vitro Kinase Assay

KINASE: Human, pre-activated MAPKAP-K2 has been purchased from Upstate, Waltham, Mass., USA (cat. no. 14-337)

SUBSTRATE: A carboxy-terminal amidated 17mer peptide with the sequence SEQ ID NO:11 APAYSRAL SRQLSSGVS, derived from the amino acid sequence around serine 78 of the heat-shock protein 27 (HSP27) has been synthesized and purified by HPLC to >95% (Thermo, Germany). The residue phosphorylated by MAPKAP-K2 is underlined.

LIGAND: The peptide YSRAL-pS-RQLSS, containing an amidated carboxy-terminus and conjugated at the amino-terminus with the fluorophore 5-carboxytetramethyl-rhodamine (5-TAMRA) was purchased from Thermo (Germany) and used as ligand.

ANTIBODY: Anti-phospho-HSP27 antibody (clone JBW502) was purchased from Upstate, Waltham, Mass., USA (cat. no. 05-645).

ASSAY SETUP: The kinase reaction contains 3 μM substrate peptide, 10 μM ATP and 0.5 nM MAPKAP-K2. The reaction buffer conditions are 16 mM HEPES/KOH pH 7.4, 8 mM $MgCl_2$, 0.4 mM DTT, 0.08% (w/v) BSA, 0.008% (w/v) Pluronic F127, 3% (v/v) DMSO.

The kinase reaction is at 30° C. for 30 min. The kinase reaction is terminated by addition of 0.67 reaction volumes of 12.5 nM ligand and 25 nM antibody in 20 mM HEPES/KOH pH 7.4, 50 mM EDTA, 0.5 mM DTT, 0.05% (w/v) Tween 20. After 30 min equilibration time at room temperature, samples are subjected to fluorescence polarization measurement. The fluorescence polarization readout was generated on an Analyst AD multimode reader (Molecular Devices) with a filter setup as described for the ERK2 assay.

Example 2d

EGFR in vitro Kinase Assay

KINASE: Human EGFR has been purchased from Sigma, Germany (cat. no. E3614).

SUBSTRATE: Poly(Glu, Tyr) purchased from Sigma, Germany (cat. no. P0275) has been employed as kinase substrate.

LIGAND: Ligand was from the Tyrosine Kinase Assay Kit, Green (Invitrogen, Germany, cat. no. P2837), supplied as 10 fold concentrate.

ANTIBODY: Phospho-tyrosine specific antibody was from the Tyrosine Kinase Assay Kit, Green (Invitrogen, Germany, cat. no. P2837), supplied as 10 fold concentrate.

ASSAY SETUP: The kinase reaction contains 3 μg/ml poly(Glu, Tyr), 3 μM ATP and 10 nM EGFR. The reaction buffer conditions are 20 mM HEPES/KOH pH 7.4, 5 mM $MgCl_2$, 2 mM manganese chloride ($MnCl_2$, Roth, Germany, cat. no. T881.1), 0.25 mM DTT, 0.03% Tween 20, 50 μM sodium orthovanadate ($Na_3VO_4$, Sigma, Germany, cat. no. S6508), 3% (v/v) DMSO.

The kinase reaction is at 22° C. for 30 min. The kinase reaction is terminated by addition of 0.67 reaction volumes of 2.5 fold concentrated ligand and 2.5 fold concentrated antibody in 25 mM HEPES/KOH pH 7.4, 100 mM EDTA, 0.3 mM DTT, 0.05% (w/v) Tween 20. After 30 min equilibration time at room temperature, samples are subjected to fluorescence polarization measurement. The fluorescence polarization readout was generated on an Analyst AD multimode reader (Molecular Devices, Sunnyvale, Calif., USA) equipped with a 505 nm dichroic mirror (Molecular Devices, Sunnyvale, Calif., USA, cat. no. 42-000-0033), a 485/20 nm band pass filter (Molecular Devices, Sunnyvale, Calif., USA, cat. no. 42-000-0031) on the excitation and a 530/10 nm band pass filter (Molecular Devices, Sunnyvale, Calif., USA, cat. no. 42-000-0140) on the emission side.

Example 2e

CDK2 in vitro Kinase Assay

KINASE: Active human CDK2/cyclinE has been purchased from Upstate, Waltham, Mass., USA (cat. no. 14-475)

SUBSTRATE: $RB^{ING}$ peptide purchased from Invitrogen, Germany (cat. no. P2939) has been employed as kinase substrate.

LIGAND: Ligand was from the CDK $RB^{ING}$ Kinase Assay Kit (Invitrogen, Germany, cat. no. P2929), supplied as 10 fold concentrate.

ANTIBODY: Phospho-specific antibody was from the CDK $RB^{ING}$ Kinase Assay Kit (Invitrogen, Germany, cat. no. P2929), supplied as 4 fold concentrate.

ASSAY SETUP: The kinase reaction contains 2 μM $RB^{ING}$ peptide, 1.66 fold concentrated tracer, 20 μM ATP and 0.36 μg/ml CDK2. The reaction buffer conditions are 16 mM HEPES/KOH pH 7.4, 8 mM $MgCl_2$, 0.4 mM DTT, 0.08% (w/v) BSA, 0.008% (w/v) Pluronic F127, 3% (v/v) DMSO.

The kinase reaction is at 30° C. for 40 min. The kinase reaction is terminated by addition of 0.67 reaction volumes of 2.5 fold conc. antibody in 20 mM HEPES/KOH pH 7.4, 50 mM EDTA, 0.5 mM DTT, 0.05% (w/v) Tween 20. After 30 min equilibration time at room temperature, samples are subjected to fluorescence polarization measurement. The fluorescence polarization readout was generated on an Analyst AD multimode reader (Molecular Devices) with a filter setup as described for the EGFR assay.

It has been shown that the compounds of the invention exhibit $IC_{50}$ values below 10 micromolar in in vitro biological screening assays for inhibition of Mnk 1 and/or Mnk 2 kinase activity.

Furthermore, it has been shown that after oral application to mice or rats, compounds of the invention are readily detectable in the plasma of these animals.

Furthermore, it has been shown that oral application of compounds of the invention to mice leads to hypophosphorylation of the Mnk-specific substrate eIF4E in liver.

Furthermore, it has been shown that oral application of compounds of the invention to mouse models of type 2 diabetes mellitus and adipositas, results in reduced plasma lipids, improved glucose tolerance as assessed by an oral glucose tolerance test, improved insulin sensitivity as assessed by an intraperitoneal insulin tolerance test and reduced weight gain.

The invention claimed is:

1. A method of treating a subject for diabetes mellitus type II or obesity, comprising:
    administering to the subject a therapeutically effective amount of a pharmaceutical composition prepared from a compound of the general formula (I)

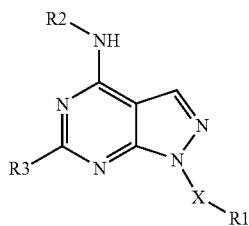

wherein $R^1$ is substituted aryl having 6 to 10 carbon atoms or optionally substituted heteroaryl having 5 to 10 ring atoms, wherein the substituents are one or more of $R^4$, wherein $R^4$ is independently halogen; CN; $COOR^5$; $OR^5$; $C(O)N(R^5R^{5a})$; $S(O)_2N(R^5R^{5a})$; $S(O)N(R^5R^{5a})$; $S(O)_2R^5$; $N(R^5)S(O)_2N(R^{5a}R^{5b})$; $SR^5$; $N(R^5R^{5a})$; $OC(O)R^5$; $N(R^5)C(O)R^{5a}$; $N(R^5)S(O)_2R^{5a}$; $N(R^5)S(O)R^{5a}$; $N(R^5)C(O)N(R^{5a}R^{5b})$; $N(R^5)C(O)OR^{5a}$; $OC(O)N(R^5R^{5a})$; oxo (=O), where the ring is at least partially saturated; $C(O)R^5$; $T^1$; or $C_{1-6}$ alkyl, wherein $C_{1-6}$ alkyl is optionally substituted with one or more $R^6$;

$R^5$, $R^{5a}$ and $R^{5b}$ are independently selected from the group consisting of H; $T^1$; and $C_{1-6}$ alkyl, wherein $C_{1-6}$ alkyl is optionally substituted with one or more $R^7$;

$R^6$, $R^7$ are independently selected from the group consisting of halogen; CN; $COOR^8$; $OR^8$; $C(O)R^8$; $C(O)N(R^8R^{8a})$; $S(O)_2N(R^8R^{8a})$; $S(O)N(R^8R^{8a})$; $S(O)_2R^8$; $N(R^8)S(O)_2N(R^{8a}R^{8b})$; $SR^8$; $N(R^8R^{8a})$; $OC(O)R^8$; $N(R^8)C(O)R^{8a}$; $N(R^8)S(O)_2R^{8a}$; $N(R^8)S(O)R^{8a}$; $N(R^8)C(O)N(R^{8a}R^{8b})$; $N(R^8)C(O)OR^{8a}$; $OC(O)N(R^8R^{8a})$; and $T^1$;

$R^8$, $R^{8a}$, $R^{8b}$ are independently selected from the group consisting of H; $C_{1-6}$ alkyl; and $T^1$;

wherein $T^1$ is $C_{3-10}$ cycloalkyl; $C_{4-10}$ bicycloalkyl; $C_{4-10}$ hetercyclyl; $C_{4-10}$ heterobicyclyl; aryl having 6 to 10 carbon C atoms; heteroaryl having 5 to 10 ring atoms, wherein $T^1$ is optionally substituted with one or more $R^9$, wherein $R^9$ is independently halogen; CN; $COOR^{10}$; $OR^{10}$; $C(O)N(R^{10}R^{10a})$; $S(O)_2N(R^{10}R^{10a})$; $S(O)N(R^{10}R^{10a})$; $S(O)_2R^{10}$; $N(R^{10})S(O)_2N(R^{10a}R^{10b})$; $SR^{10}$; $N(R^{10}R^{10a})$; $OC(O)R^{10}$; $N(R^{10})C(O)R^{10a}$; $N(R^{10})S(O)_2 R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$; oxo (=O), where the ring is at least partially saturated; $C(O)R^{10}$; $C_{1-6}$ alkyl; phenyl; $C_{3-7}$ cycloalkyl; or heterocyclyl, wherein $C_{1-6}$ alkyl; phenyl; $C_{3-7}$ cycloalkyl; and heterocyclyl are optionally substituted with one or more halogen, which are the same or different;

$R^{10}$, $R^{10a}$ and $R^{10b}$ are independently selected from the group consisting of H, $C_{1-6}$ alkyl, phenyl, $C_{3-7}$ cycloalkyl, heteroaryl and heterocyclyl, wherein $C_{1-6}$ alkyl, phenyl, $C_{3-7}$ cycloalkyl and heterocyclyl are optionally substituted with one or more halogen, which are the same or different;

$R^2$ is hydrogen, $C_{1-4}$ alkyl, an acetyl group or a urea;

$R^3$ is hydrogen, a hydroxyl, $C_{1-4}$ alkyl; or amino group; and

X is a bond;

or a pharmaceutically acceptable salt thereof, and optionally a pharmaceutically acceptable carrier.

2. The method of claim 1, wherein $R^2$ is hydrogen.

3. The method of claim 1, wherein the halogen substituents are selected from fluorine and chlorine.

4. The method of claim 1, wherein $R^1$ is a phenyl group substituted with imidazolyl, a phenyl group substituted with condensed pyrazolo, a phenyl group substituted with trifluoromethyl, a phenylthio, or furanyl group.

5. The method of claim 1, wherein $R^1$ is a substituted phenyl group, wherein the substituents are selected from halogen, carbamoyl, substituted carbamoyl, carboxyl, heterocyclyl, or benzofused heterocyclyl.

6. The method of claim 1, wherein $R^1$ is a 5-13 membered mono- or bicyclic optionally substituted aromatic heterocycle with 1-4 heteroatoms selected from N, S and O, wherein the substituents are selected from halogen, optionally substituted amino, carboxy, carbamoyl, $C_1$-$C_4$ alkoxycarbonyl, carboxymethyl, carbamoylmethyl, $C_1$-$C_4$ alkoxycarbonylmethyl, hydroxyl, phenoxy, or $C_1$-$C_4$ alkyl.

7. The method of claim 1, wherein the compound is selected from:

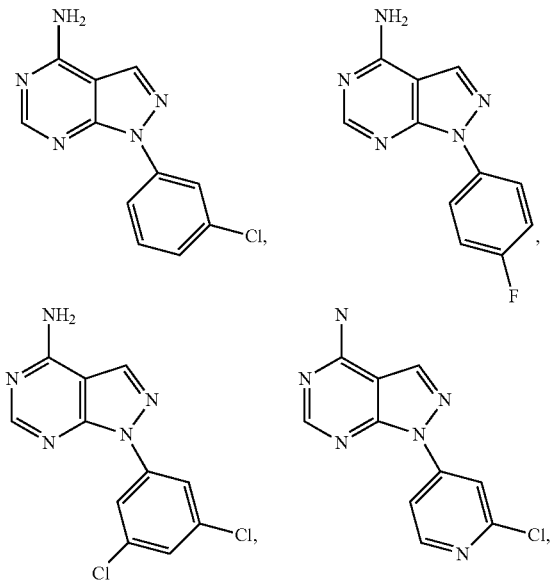

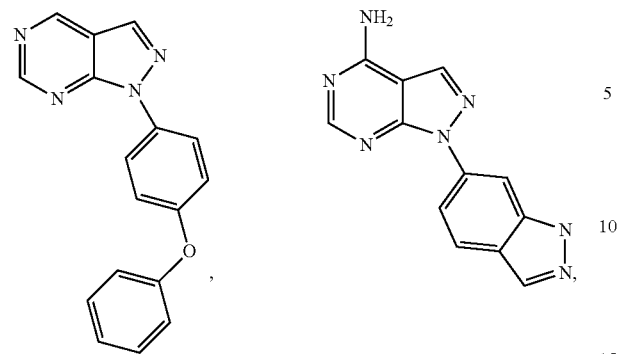
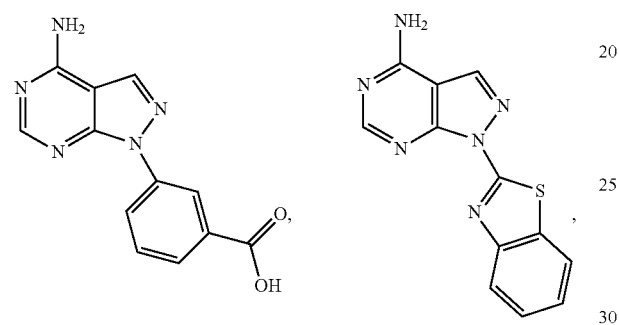
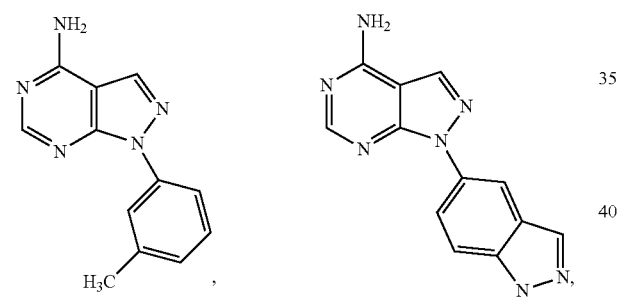
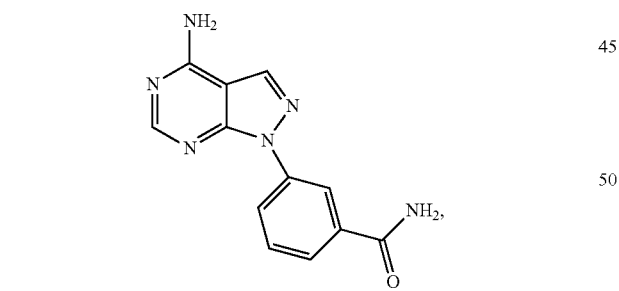
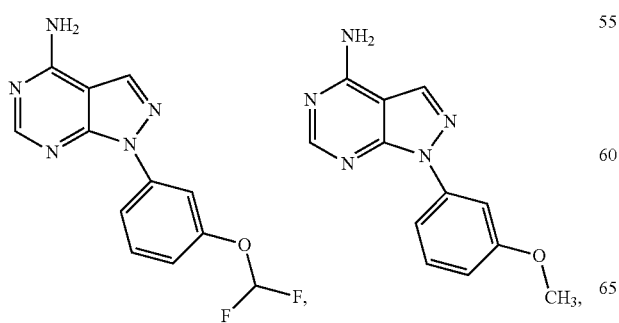
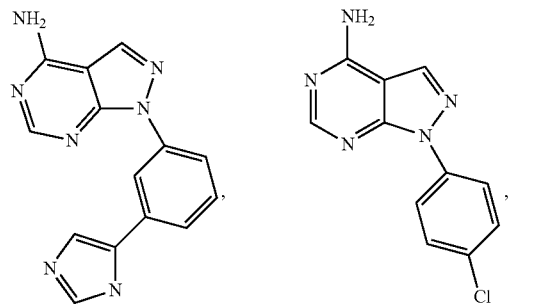
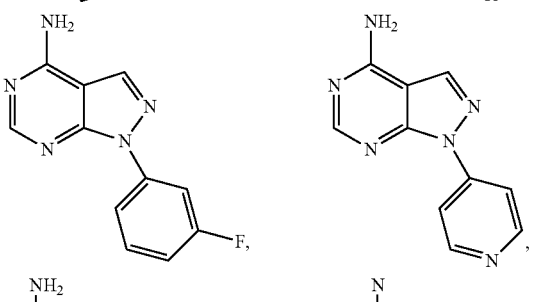
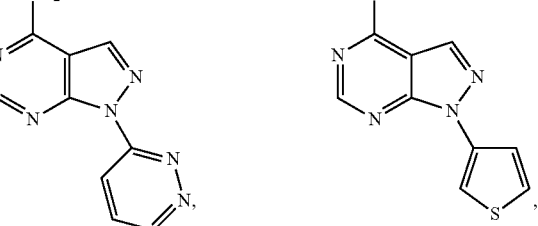
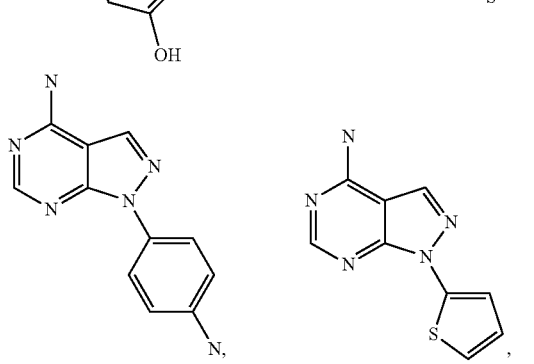
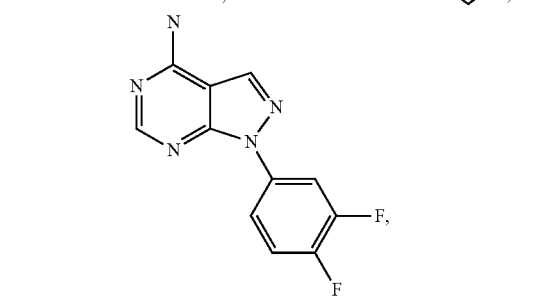
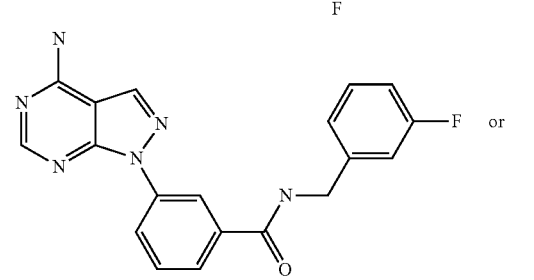

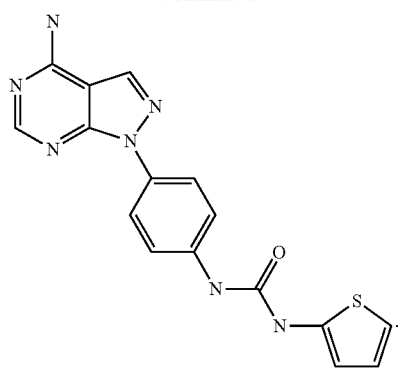
8. The method of claim 1, wherein the compound is selected from:
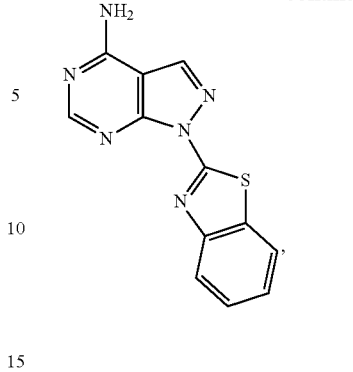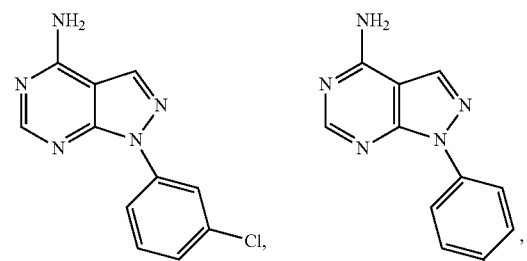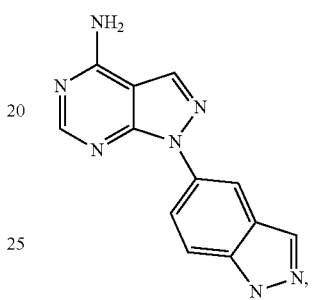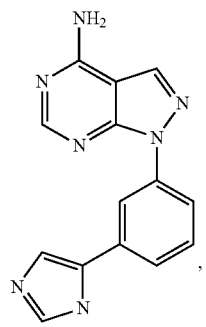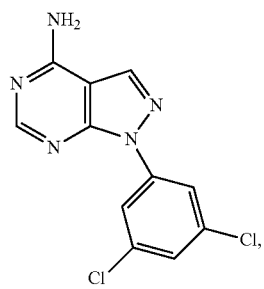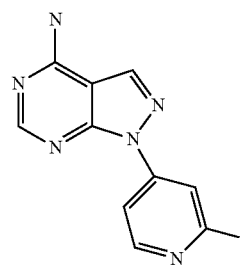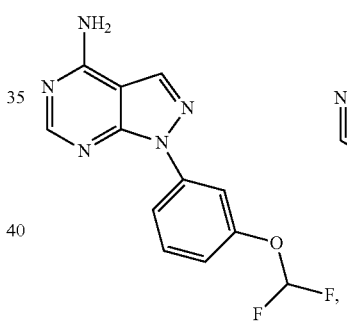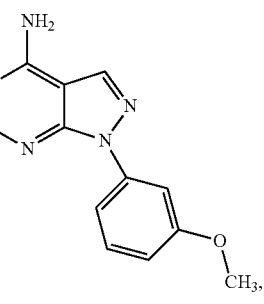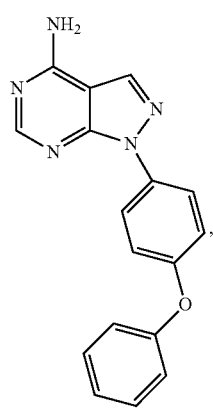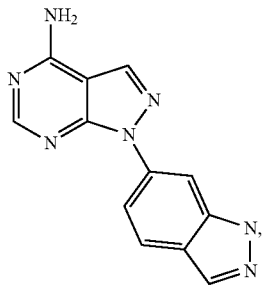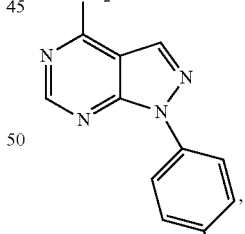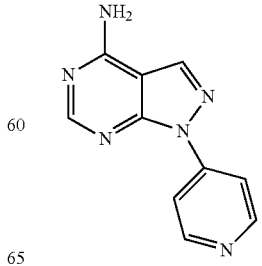or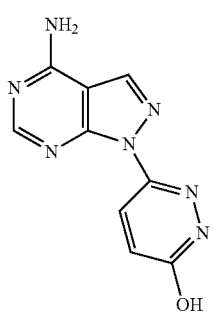

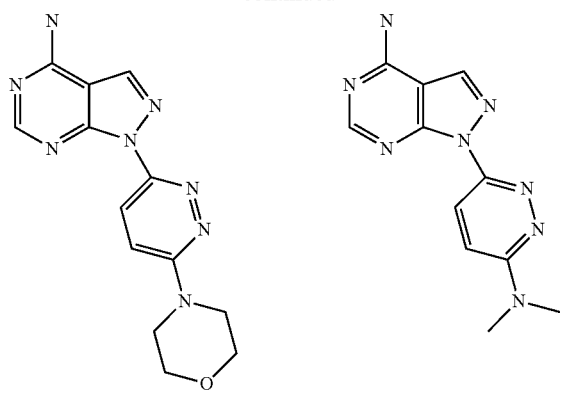
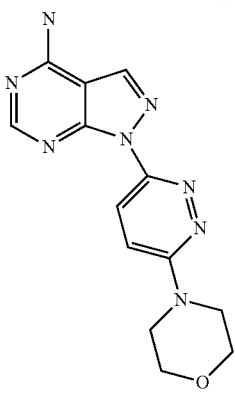
9. The method of claim 1, wherein the compound is selected from
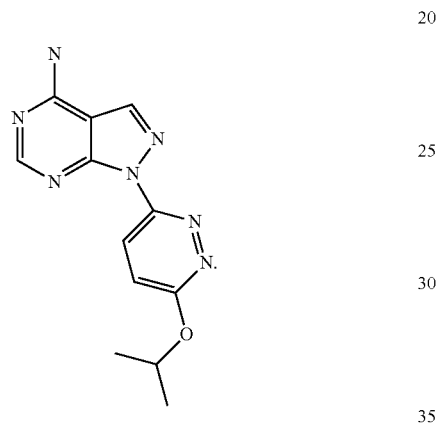
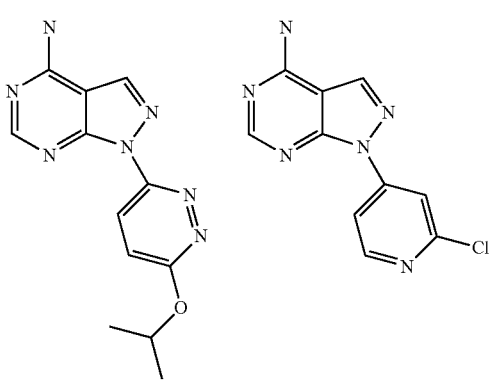
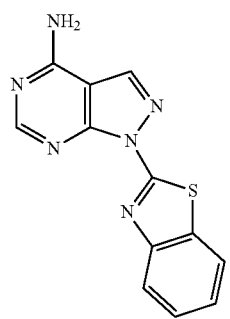
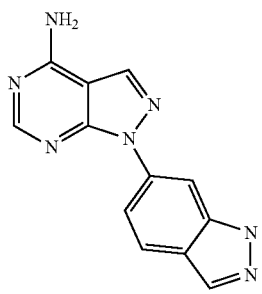
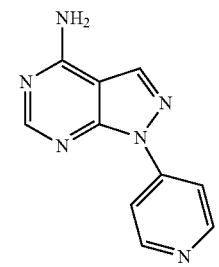
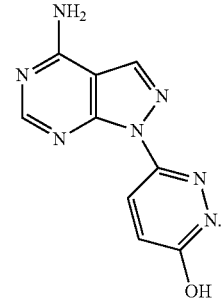
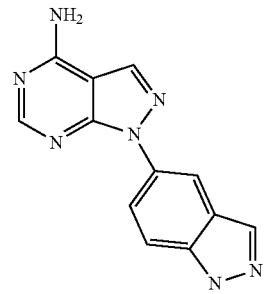
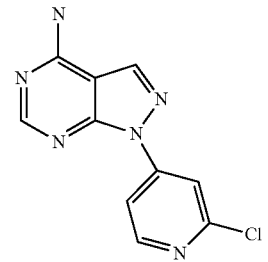
10. The method of claim 1, wherein the group —X—R¹ is selected from: 3-chlorophenyl, 4-pyridyl, 5-indazolyl, 4-phenoxyphenyl, 3-carboxamidophenyl, (3-(3H-imidazol-4-yl)phenyl, 3-hydroxypyridaz-6-yl, 4-fluorophenyl, 6-indazolyl, 3-fluorophenyl, 4-chlorophenyl, 3-methoxyphenyl, 3-difluoromethoxyphenyl, 3,5-dichlorophenyl, or 3-carboxyphenyl.

11. The method of claim 1, wherein the compound is selected from:
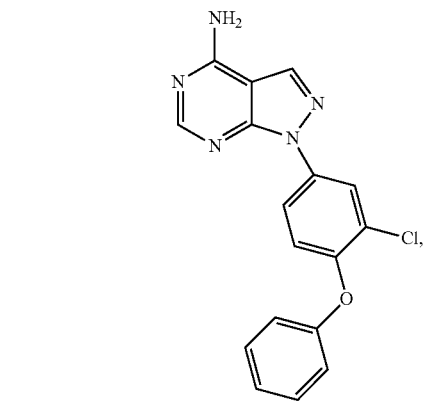
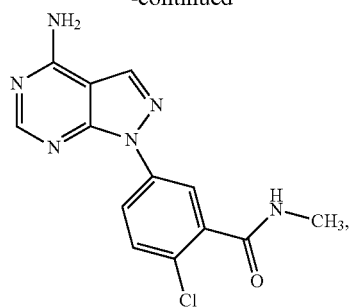
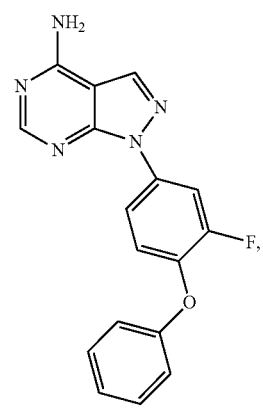
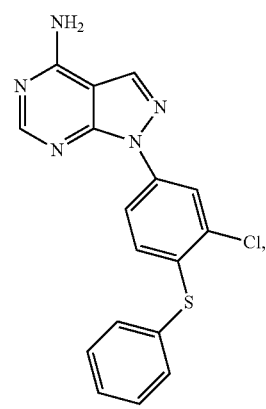
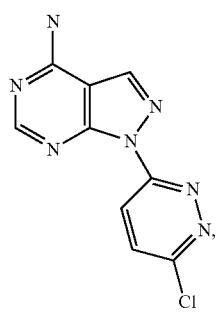
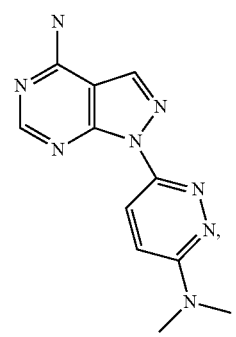
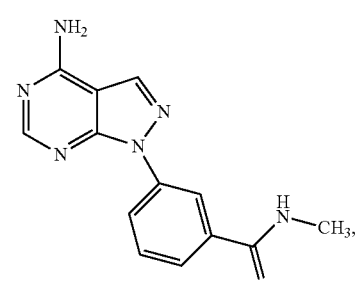
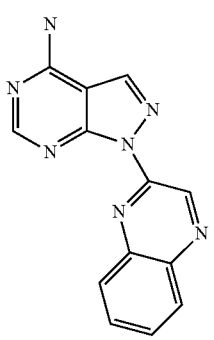
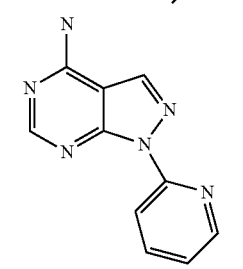
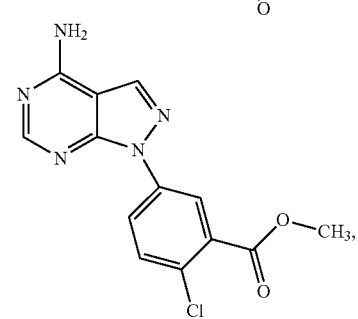
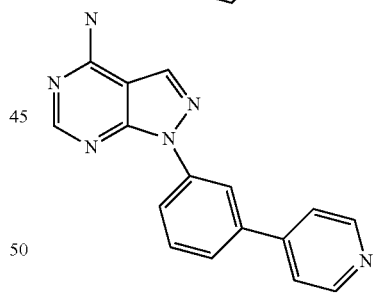
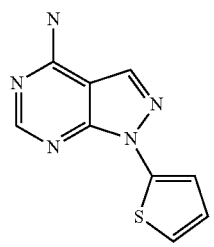
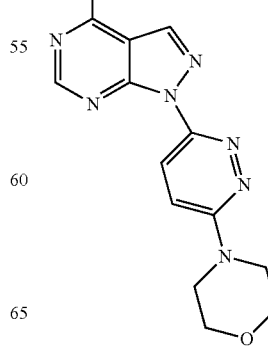
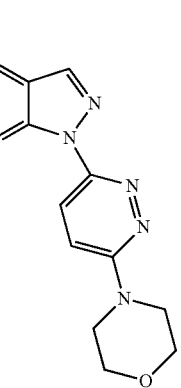
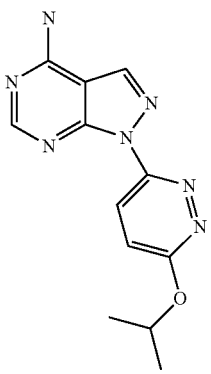

87
-continued
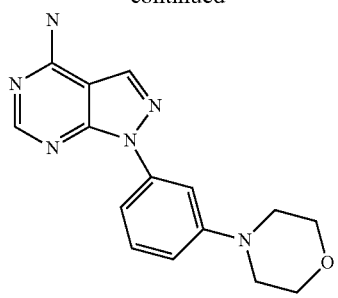
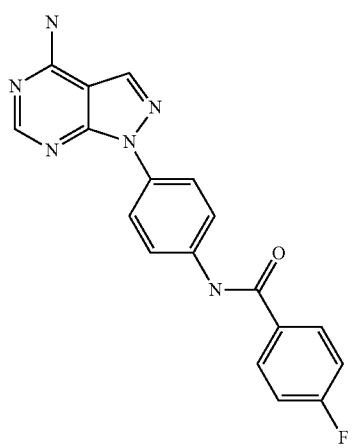
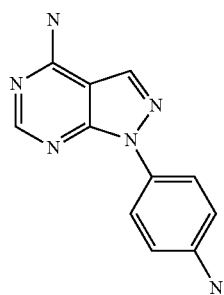
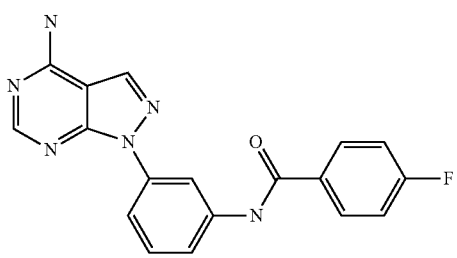
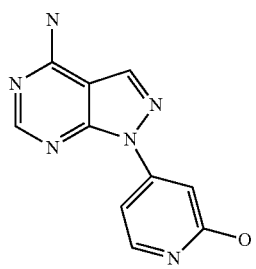
88
-continued
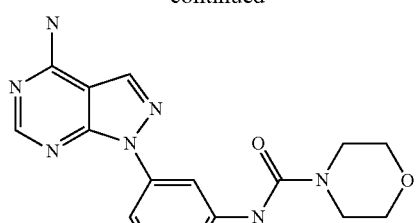
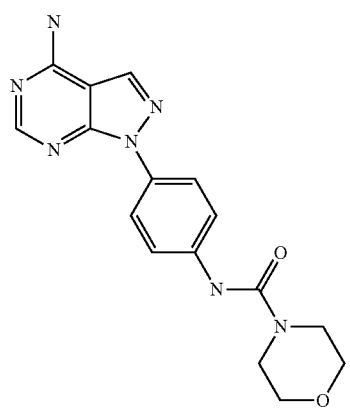
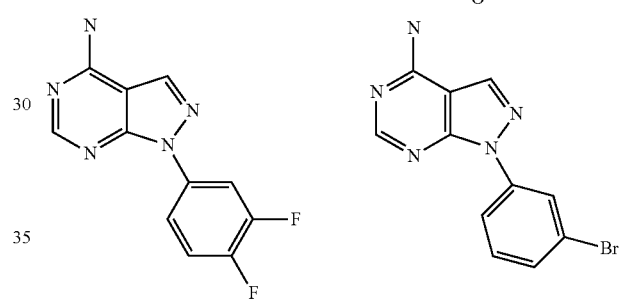
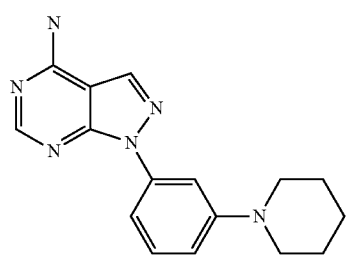
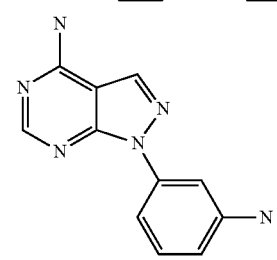
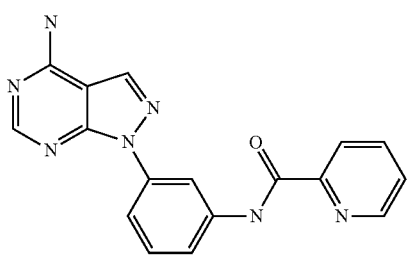

89
-continued
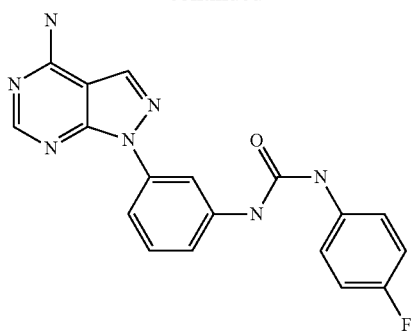
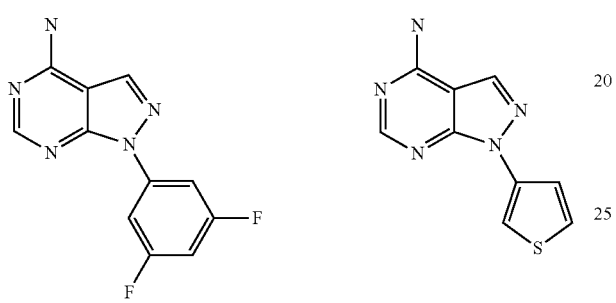
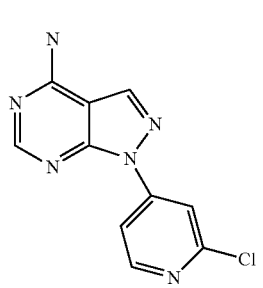
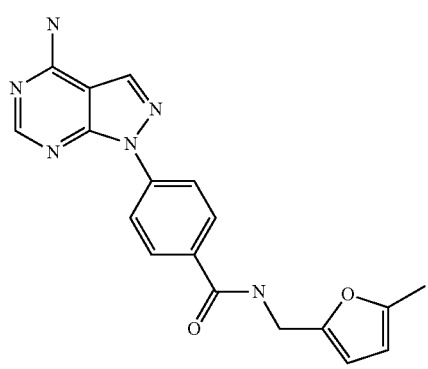
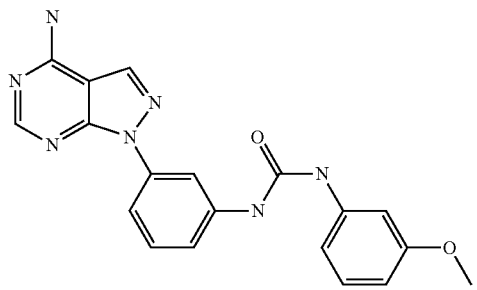
90
-continued
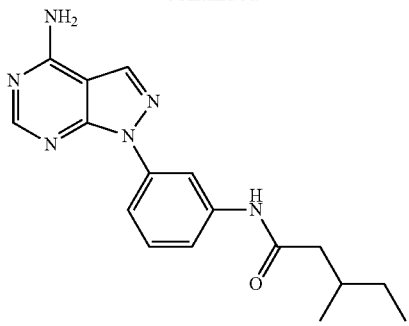
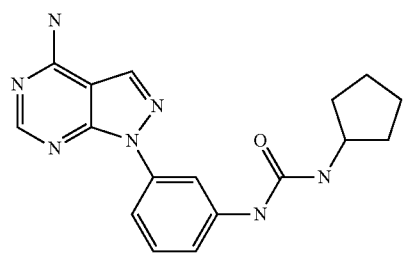
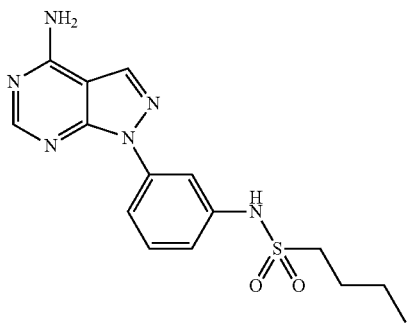
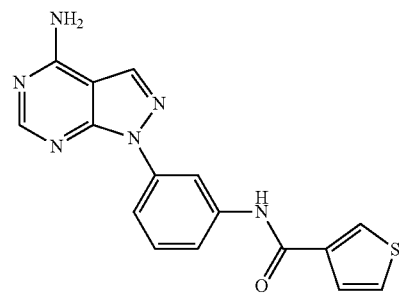
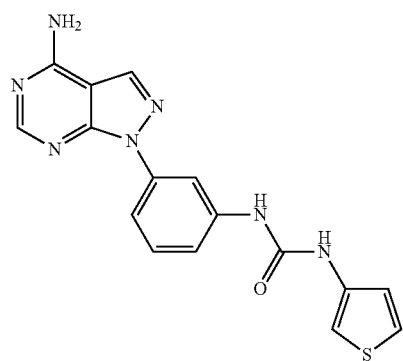

91
-continued
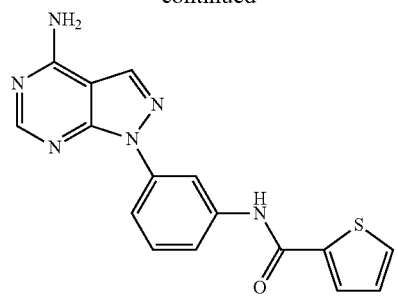
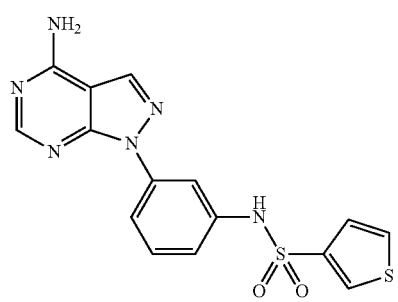
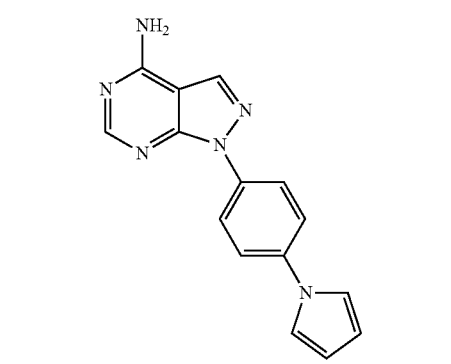
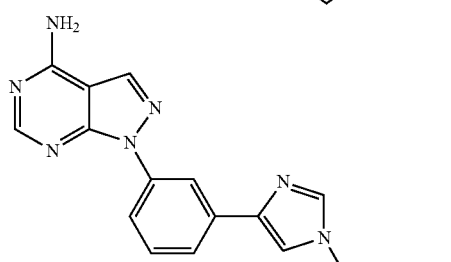
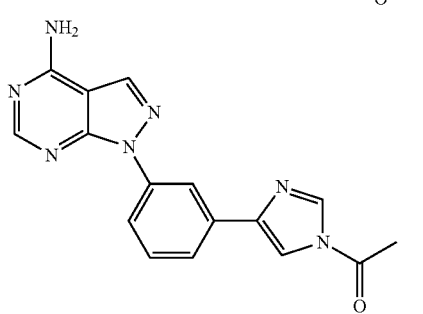
92
-continued
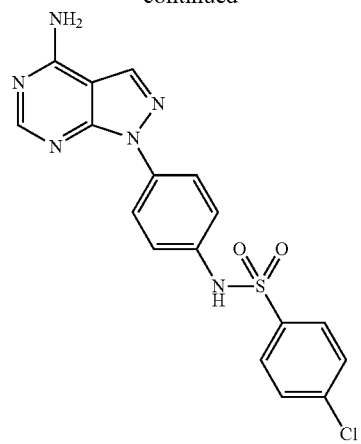
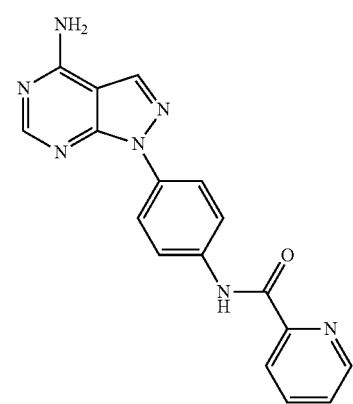
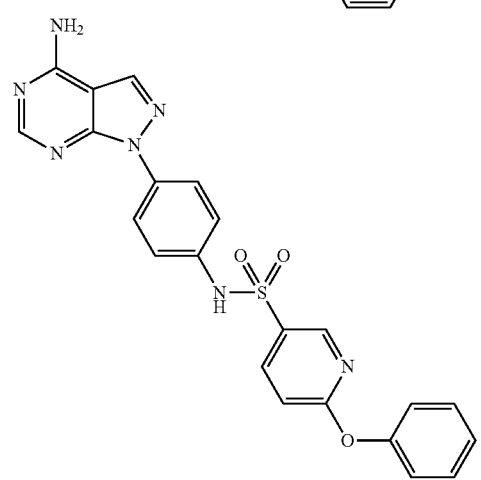
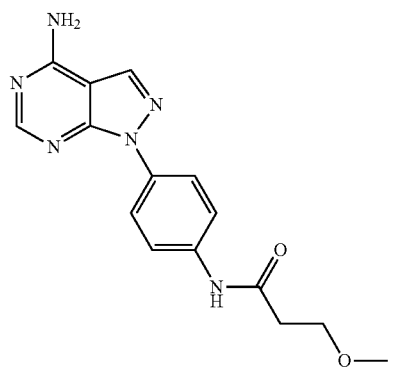

-continued
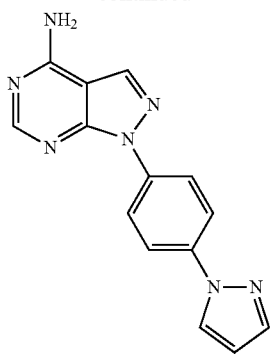
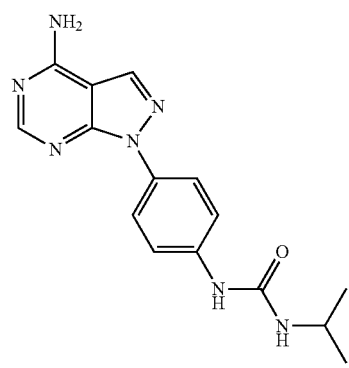
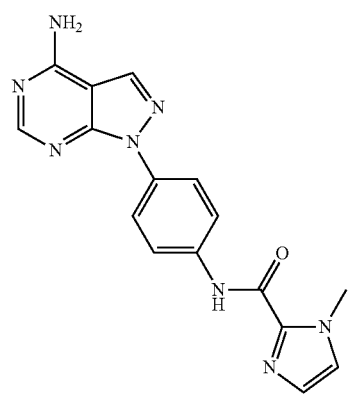
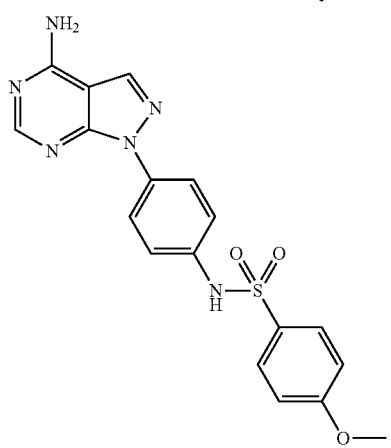
-continued
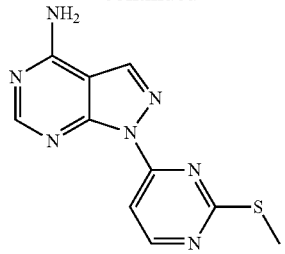
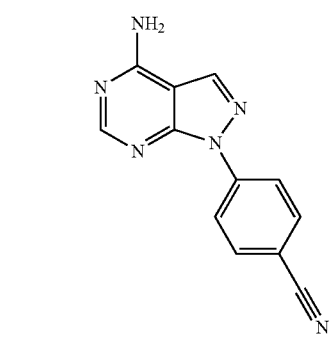
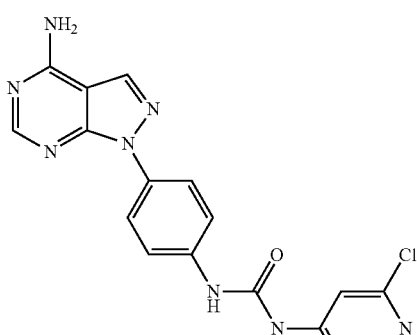
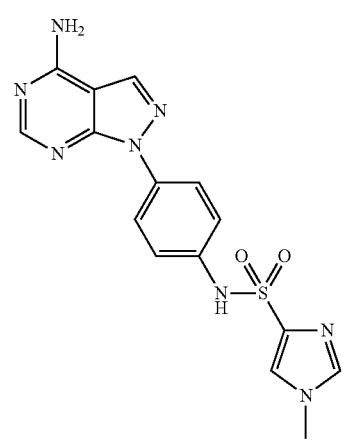

95
-continued
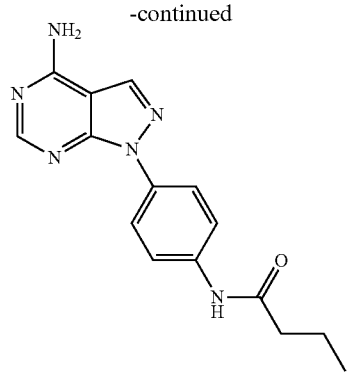
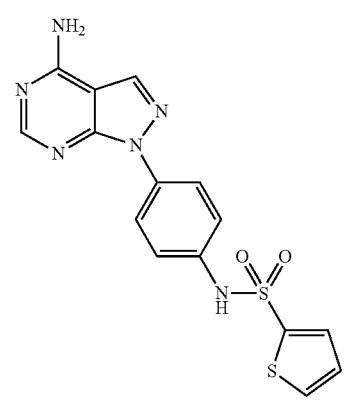
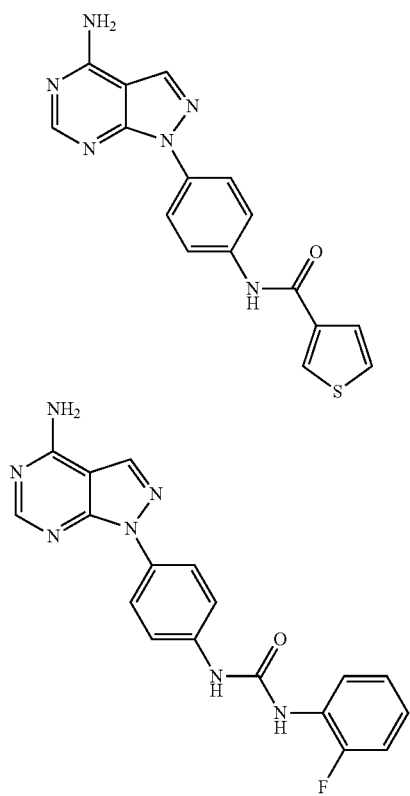
96
-continued
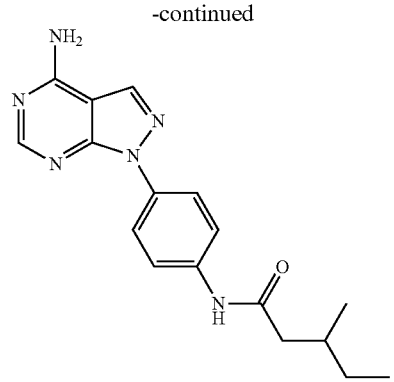
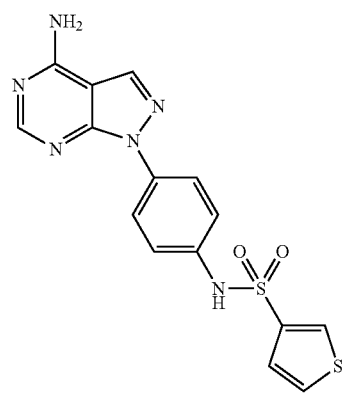
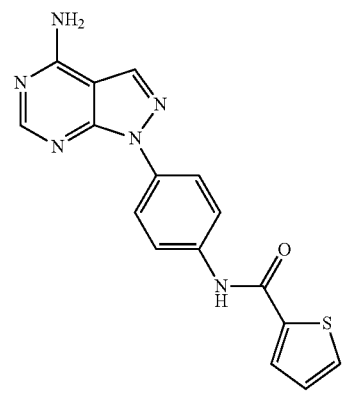
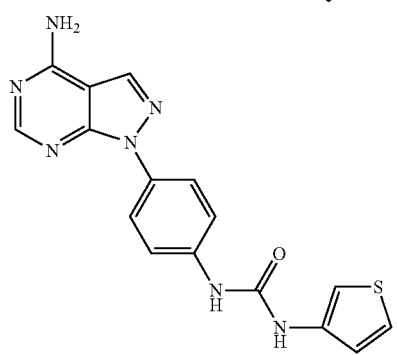

97
-continued
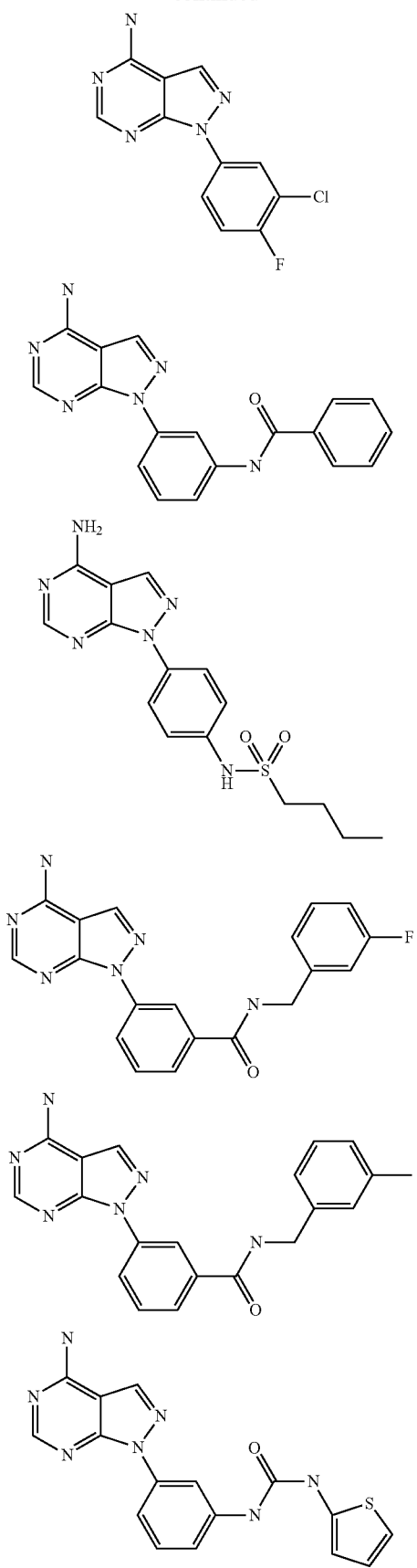
98
-continued
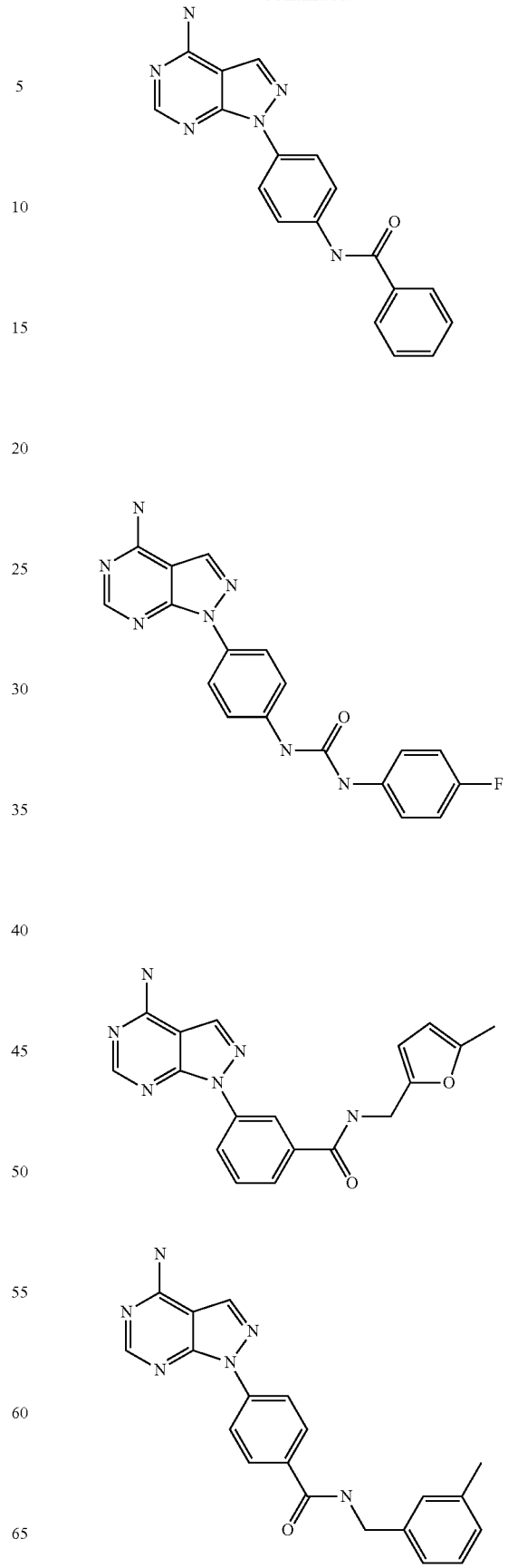

99
-continued
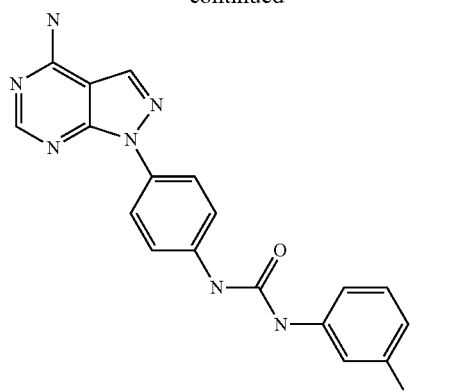
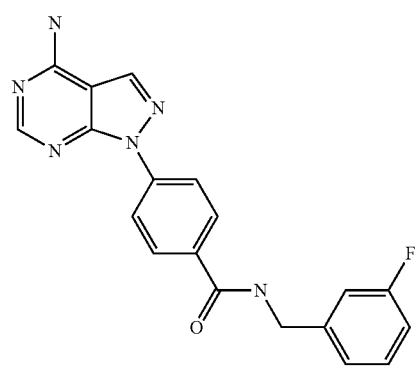
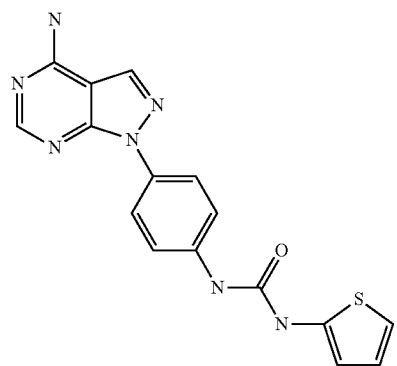
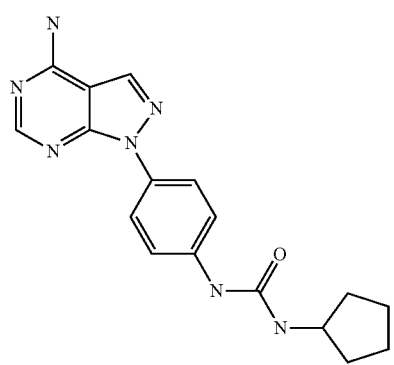
100
-continued
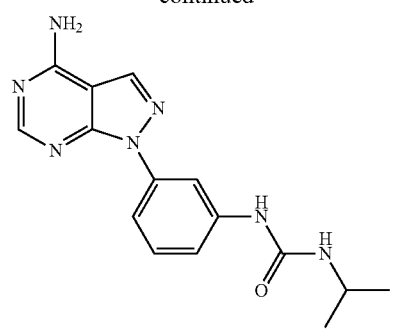
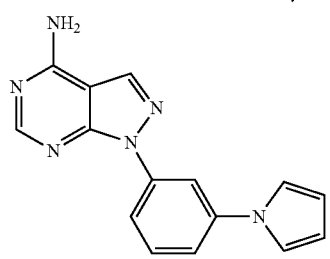
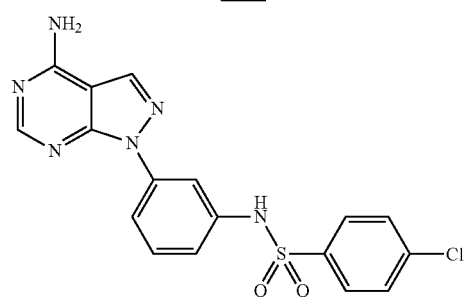
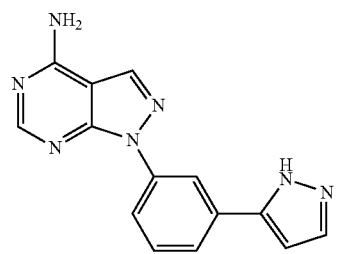
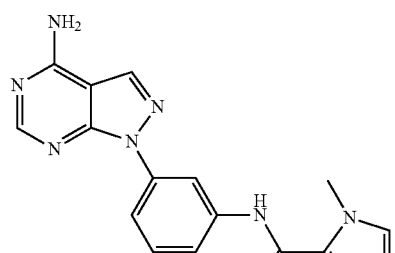
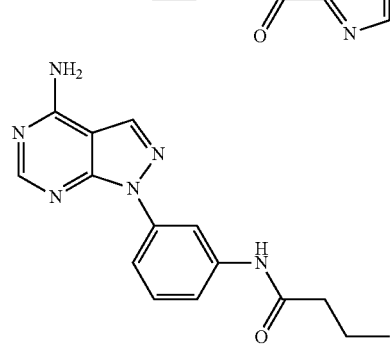

-continued

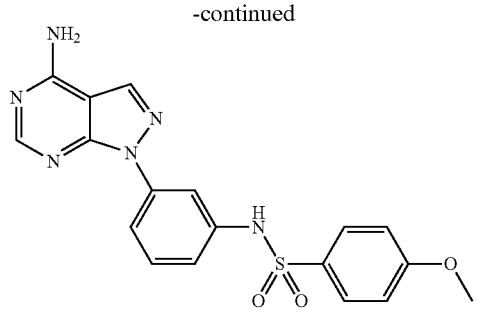

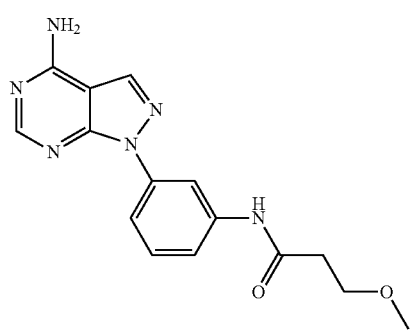

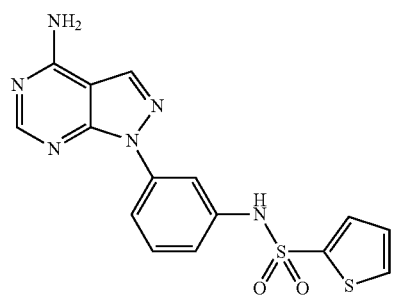

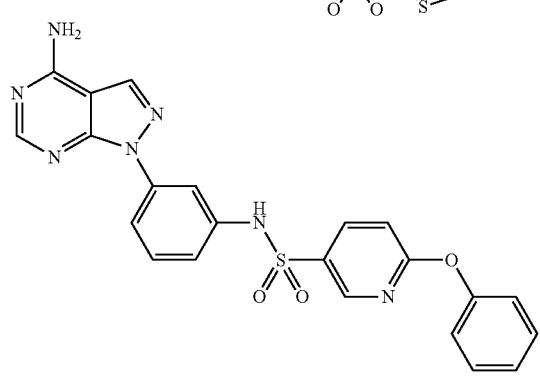

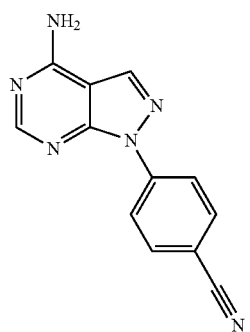

-continued

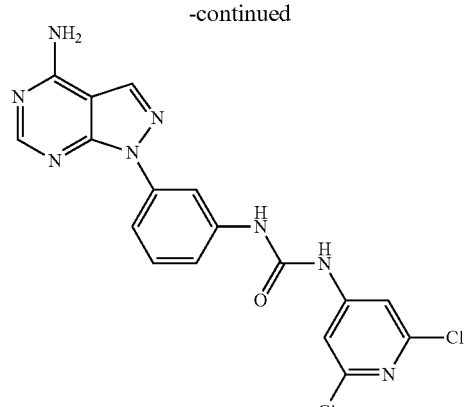

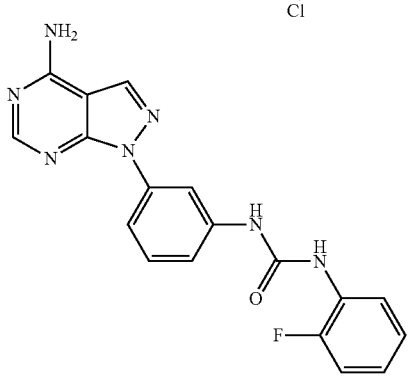

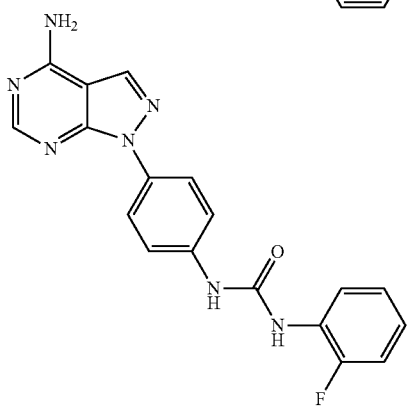

1-(1H-indazol-5-yl)-1H-pyrazolo[3,4-d]pyrimidin-4-ylamine,
1-(4-phenoxy-phenyl)-1H-pyrazolo[3,4-d]pyrimidin-4-ylamine,
3-(4-amino-pyrazolo[3,4-d]pyrimidin-1-yl)-bezamide,
1-[3-(3H-imidazol-4-yl)-phenyl]-1H-pyrazolo[3,4-d]pyrimidin-4-ylamine,
1-(4-fluoro-phenyl)-1H-pyrazolo[3,4-d]pyrimidin-4-ylamine,
1-(1H-indazol-6-yl)-1H-pyrazolo[3,4-d]pyrimidin-4-ylamine,
5-(4-amino-pyrazolo[3,4-d]pyrimidin-1-yl)-2-chloro-benzamide,
3-(4-amino-pyrazolo[3,4-d]pyrimidin-1-yl)-benzoic acid,
1-(3-difluoromethoxy-phenyl)-1H-pyrazolo[3,4-d]pyrimidin-4-ylamine,
1-(3-methoxy-phenyl)-1H-pyrazolo[3,4-d]pyrimidin-4-ylamine,
1-(3-fluoro-phenyl)-1H-pyrazolo[3,4-d]pyrimidin-4-ylamine,
1-pyrindin-2-yl-1H-pyrazolo[3,4-d]pyrimidin-4-ylamine, 1-benzooxazol-2yl-1H-pyrazolo[3,4-d]pyrimidin-4-ylamine,
1-quinoxalin-2-yl-1H-pyrazolo[3,4-d]pyrimidin-4-ylamine,
1-benzothiazol-2-yl-1H-prazolo[3,4-d]pyrimidin-4-ylamine,
1-pyridin-4-yl-1H-pyrazolo[3,4-d]pyrimidin-4-ylamine,
1-(3,5-dimethyl-1H-pyrazol-4-yl)-1H-pyrazolo[3,4-d]pyrimidin-4-ylamine,
1-(4-methyl-oxazol-2-yl)-1H-pyrazolo[3,4-d]pyrimidin-4-ylamine,
1-thiazol-2-yl-1H-pyrazolo[3,4-d]pyrimidin-4-ylamine,
1-(4-methyl-thiazol-2-yl)-1H-pyrazolo[3,4-d]pyrimidin-4-ylamine,
1-(4-tert-butyl-thiazol-2-yl)-1H-pyrazolo[3,4-d]pyrimidin-4-yl-amine,
1-(4H-[1,2,4]triazol-3-yl)-1H-pyrazolo[3,4-d]pyrimidin-4-ylamine,
1-pyridin-3-yl-1H-pyrazolo[3,4-d]pyrimidin-4-ylamine,
1-pyrimidin-5-yl-1H-pyrazolo[3,4-d]pyrimidin-4-ylamine,
1-pyrimidin-2-yl-1H-pyrazolo[3,4-d]pyrimidin-4-ylamine,
1-pyrimidin-4-yl-1H-pyrazolo[3,4-d]pyrimidin-4-ylamine,
2-(4-amino-pyrazolo[3,4-d]pyrimidin-1-yl)-thiazole-4-carboxylic acid,
2-(4-amino-pyrazolo[3,4-d]pyrimidin-1-yl)-thiazole-4-carboxylic acid methyl ester,
2-(4-amino-pyrazolo[3,4-d]pyrimidin-1-yl)-thiazole-4-carboxylic acid amide,
2-(4-amino-pyrazolo[3,4-d]pyrimidin-1-yl)-thiazole-5-carboxylic acid,
2-(4-amino-pyrazolo[3,4-d]pyrimidin-1-yl)-thiazole-5-carboxylic acid methyl ester,
2-(4-amino-pyrazolo[3,4-d]pyrimidin-1-yl)-thiazole-5-carboxylic acid amide,
[2-(4-amino-pyrazolo[3,4-d]pyrimidin-1-yl)-thiazol-4-yl]-acetic acid,
[2-(4-amino-pyrazolo[3,4-d]pyrimidin-1-yl)-thiazol-4-yl]-acetic acid methyl ester,
2-[2-(4-amino-pyrazolo[3,4-d]pyrimidin-1-yl)-thiazol-4-yl]-acetamide,
[2-(4-amino-pyrazolo[3,4-d]pyrimidin-1-yl)-thiazol-5-yl]-acetic acid,
[2-(4-amino-pyrazolo[3,4-d]pyrimidin-1-yl)-thiazol-5-yl]-acetic acid methyl ester,
[2-(4-amino-pyrazolo[3,4-d]pyrimidin-1-yl)-thiazol-5-yl]-acetamide,
1-benzo[b]thiophen-3-yl-1H-pyrazolo[3,4-d]pyrimidin-4-ylamine,
1-(5-fluoro-benzo[b]thiophen-3-yl)-1H-pyrazolo[3,4-d]pyrimidin-4-ylamine,
1-(6-chloro-benzo[b]thiophen-3-yl)-1H-pyrazolo[3,4-d]pyrimidin-4-ylamine,
1-(7-chloro-benzo[b]thiophen-3-yl)-1H-pyrazolo[3,4-d]pyrimidin-4-ylamine,
1-(5-chloro-benzo[b]thiophen-3-yl)-1H-pyrazolo[3,4-d]pyrimidin-4-ylamine,
1-benzofuran-3-yl-1H-pyrazolo[3,4-d]pyrimidin-4-ylamine,
1-(5-fluoro-benzofuran-3-yl)-1H-pyrazolo[3,4-d]pyrimidin-4-ylamine,
1-(5-chloro-benzofuran-3-yl)-1H-pyrazolo[3,4-d]pyrimidin-4-ylamine,
1-(6-chloro-benzofuran-3-yl)-1H-pyrazolo[3,4-d]pyrimidin-4-ylamine,
1-(7-chloro-benzofuran-3-yl)-1H-pyrazolo[3,4-d]pyrimidin-4-ylamine,
1-(1H-indol-3-yl)-1H-pyrazolo[3,4-d]pyrimidin-4-ylamine,
1-(5-fluoro-1H-indol-3-yl)-1H-pyrazolo[3,4-d]pyrimidin-4-ylamine,
1-(5-chloro-1H-indol-3-yl)-1H-pyrazolo[3,4-d]pyrimidin-4-ylamine,
1-(6-chloro-1H-indol-3-yl)-1H-pyrazolo[3,4-d]pyramidin-4-ylamine,
1-(7-chloro-1H-indol-3-yl)-1H-pyrazolo[3,4-d]pyrimidin-4-ylamine,
1-(1H-pyrrolo[2,3-b]pyridine-3-yl)-1H-pyrazolo[3,4-d]pyrimidin-4-ylamine,
1-(1H-pyrrolo[2,3-c]pyridine-3-yl)-1H-pyrazolo[3,4-d]pyrimidin-4-ylamine,
1-(1H-pyrrolo[3,2-c]pyridine-3-yl)-1H-pyrazolo[3,4-d]pyrimidin-4-ylamine,
1-(1H-Pyrrolo[3,2-b]pyridine-3-yl)-1H-pyrazolo[3,4-d]pyrimidin-4-ylamine,
1-quinazolin-4-yl-1H-pyrazolo[3,4-d]pyrimidin-4-ylamine,
6-(4-amino-pyrazolo[3,4-d]pyrimidin-1-yl)-pyridazin-3-ol,
1-(6-amino-pyridazin-3-yl)-1H-pyrazolo[3,4-d]pyrimidin-4-ylamine,
1-(6-dimethylamino-pyridazin-3-yl)-1H-pyrazolo[3,4-d]pyrimidin-4-ylamine,
1-(6-phenylamino-pyridazin-3-yl)-1H-pyrazolo[3,4-d]pyrimidin-4-ylamine,
1-(6-phenoxy-pyridazin-3-yl)-1H-pyrazolo[3,4-d]pyrimidin-4-ylamine,

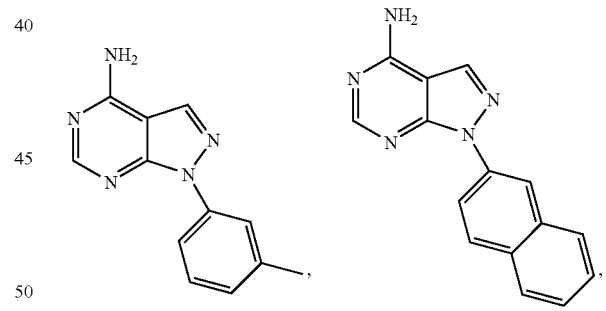

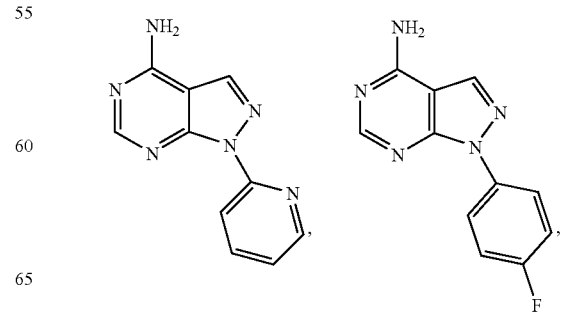

-continued
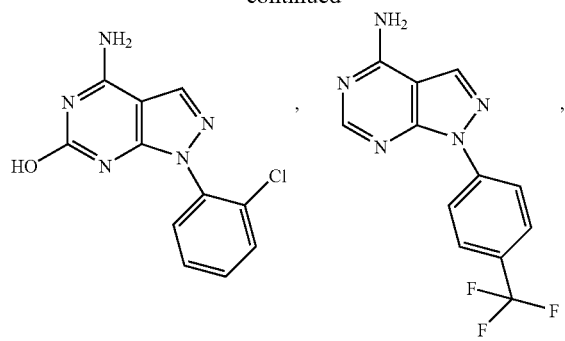
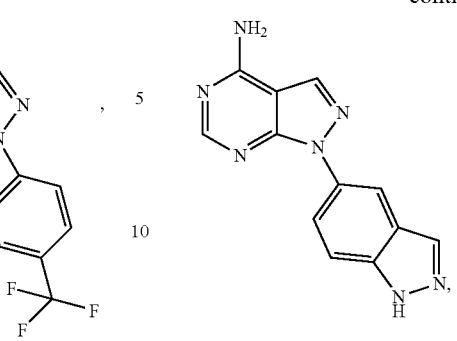
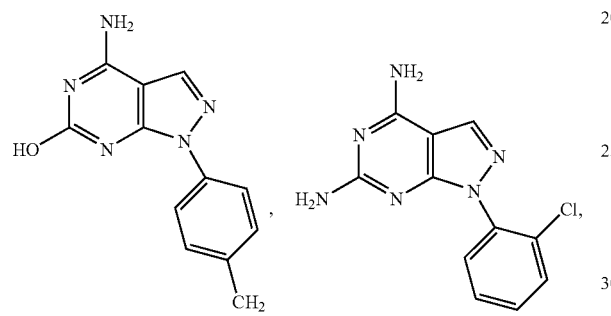
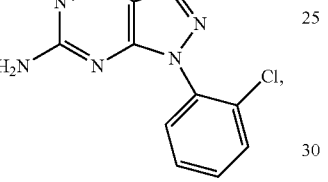
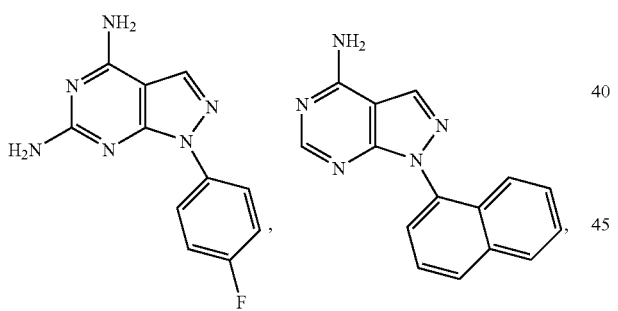
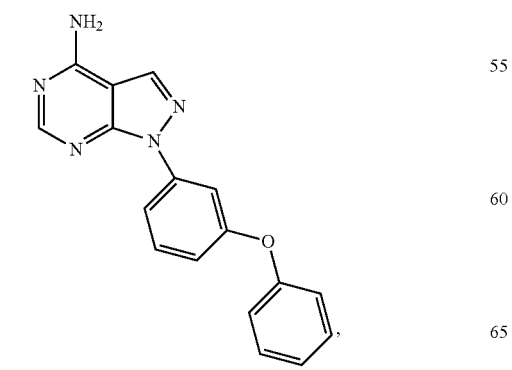
-continued
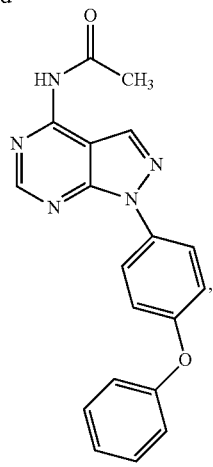
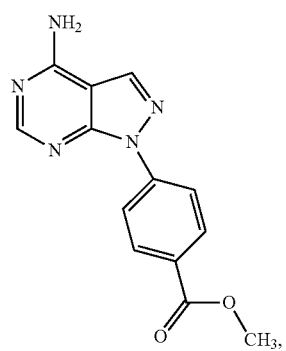
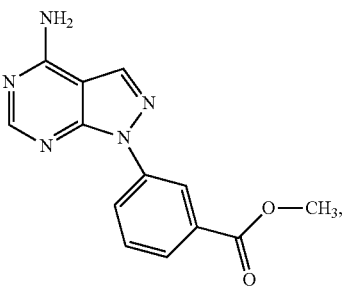
② indicates text missing or illegible when filed
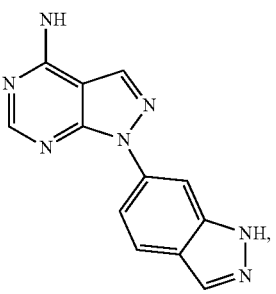

-continued

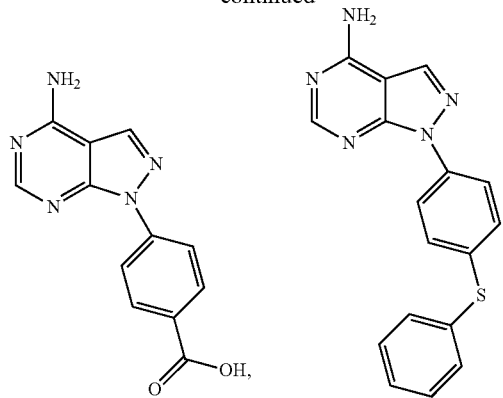

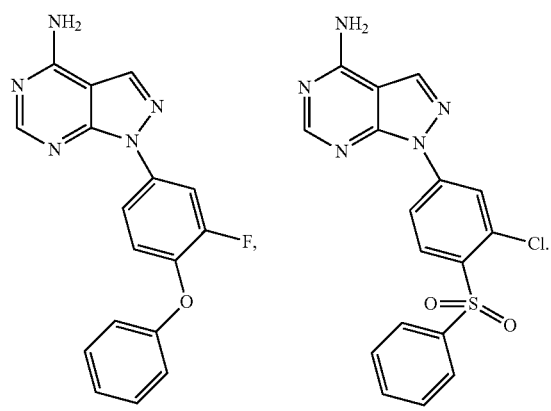

12. The method of claim 1, wherein the compound is selected from

-continued

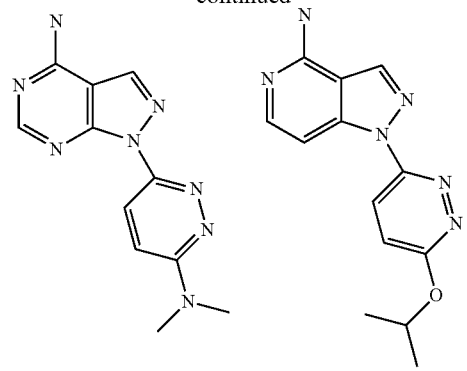

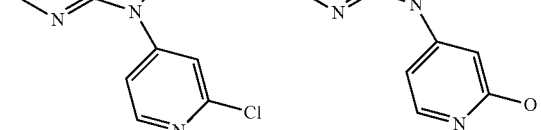

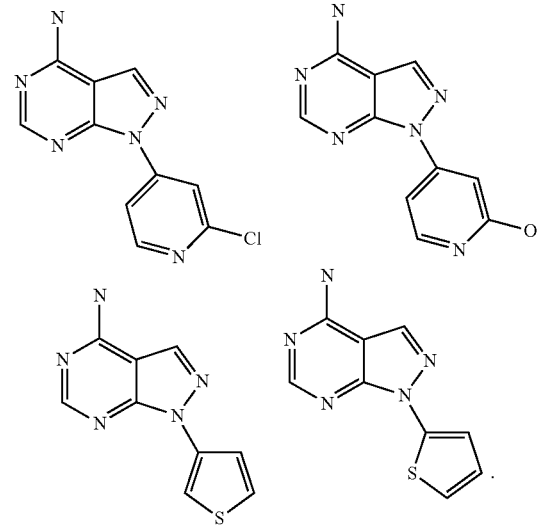

2-(4-amino-pyrazolo[3,4-d]pyrimidin-1-yl)-thiazole-4-carboxylic acid amide,
2-(4-amino-pyrazolo[3,4-d]pyrimidin-1-yl)-thiazole-5-carboxylic acid,
2-(4-amino-pyrazolo[3,4-d]pyrimidin-1-yl)-thiazole-5-carboylic acid methyl ester,
2-(4-amino-pyrazolo[3,4-d]pyrimidin-1-yl)-thiazole-5-carboxylic acid amide,
[2-(4-amino-pyrazolo[3,4-d]pyrimidin-1-yl)-thiazol-4-yl]-acetic acid,
[2-(4-amino-pyrazolo[3,4-d]pyrimidin-1-yl)-thiazol-4-yl]-acetic acid methyl ester,
2-[2-(4-amino-pyrazolo[3,4-d]pyrimidin-1-yl)-thiazol-4-yl]-acetamide,
[2-(4-amino-pyrazolo[3,4-d]pyrimidin-1-yl)-thiazol-5-yl]-acetic acid,
[2-(4-amino-pyrazolo[3,4-d]pyrimidin-1-yl)-thiazol-5-yl]-acetic acid methyl ester,
[2-(4-amino-pyrazolo[3,4-d]pyrimidin-1-yl)-thiazol-5-yl]-acetamide,
1-benzo[b]thiophen-3-yl-1H-pyrazolo[3,4-d]pyrimidin-4-ylamine,
1-(5-fluoro-benzo[b]thiophen-3-yl)-1H-pyrazolo[3,4-d]pyrimidin-4-ylamine,
1-(6-chloro-benzo[b]thiophen-3-yl)-1H-pyrazolo[3,4-d]pyrimidin-4-ylamine,
1-(7-chloro-benzo[b]thiophen-3-yl)-1H-pyrazolo[3,4-d]pyrimidin-4-ylamine,
1-(5-chloro-benzo[b]thiophen-3-yl)-1H-pyrazolo[3,4-d]pyrimidin-4-ylamine, 1-benzofuran-3-yl-1H-pyrazolo[3,4-d]pyrimidin-4-ylamine,
1-(5-fluoro-benzofuran-3-yl)-1H-pyrazolo[3,4-d]pyrimidin-4-ylamine,
1-(5-chloro-benzofuran-3-yl)-1H-pyrazolo[3,4-d]pyrimidin-4-ylamine,
1-(6-chloro-benzofuran-3-yl)-1H-pyrazolo[3,4-d]pyrimidin-4-ylamine,
1-(7-chloro-benzofuran-3-yl)-1H-pyrazolo[3,4-d]pyrimidin-4-ylamine,
1-(1H-indol-3-yl)-1H-pyrazolo[3,4-d]pyrimidin-4-ylamine,
1-(5-fluoro-1H-indol-3-yl)-1H-pyrazolo[3,4-d]pyrimidin-4-ylamine,
1-(5-chloro-1H-indol-3-yl)-1H-pyrazolo[3,4-d]pyrimidin-4-ylamine,
1-(6-chloro-1H-indol-3-yl)-1H-pyrazolo[3,4-d]pyramidin-4-ylamine,
1-(7-chloro-1H-indol-3-yl)-1H-pyrazolo[3,4-d]pyrimidin-4-ylamine,
1-(1H-pyrrolo[2,3-b]pyridin-3-yl)-1H-pyrazolo[3,4-d]pyrimidin-4-ylamine,
1-(1H-pyrrolo[2,3-c]pyridin-3-yl)-1H-pyrazolo[3,4-d]pyrimidin-4-ylamine,
1-(1H-pyrrolo[3,2-c]pyridin-3-yl)-1H-pyrazolo[3,4-d]pyrimidin-4-ylamine,
1-(1H-pyrrolo[3,2-b]pyridin-3-yl)-1H-pyrazolo[3,4-d]pyrimidin-4-ylamine,
1-quinazolin-4-yl-1H-pyrazolo[3,4-d]pyrimidin-4-ylamine,
6-(4-amino-pyrazolo[3,4-d]pyrimidin-1-yl)-pyridazin-3-ol,
1-(6-amino-pyridazin-3-yl)-1H-pyrazolo[3,4-d]pyrimidin-4-ylamine,
1-(6-dimethylamino-pyridazin-3-yl)-1H-pyrazolo[3,4-d]pyrimidin-4-ylamine,
1-(6-phenylamino-pyridazin-3-yl)-1H-pyrazolo[3,4-d]pyrimidin-4-ylamine,
1-(6-phenoxy-pyridazin-3-yl)-1H-pyrazolo[3,4-d]pyrimidin-4-ylamine,
1-(1H-indazol-5-yl)-1H-pyrazolo[3,4-d]pyrimidin-4-ylamine,
1-(1H-indazol-6-yl)-1H-pyrazolo[3,4-d]pyrimidin-4ylamine,
1-pyrindin-2-yl-1H-pyrazolo[3,4-d]pyrimidin-4-ylamine,
1-benzooxazol-2yl-1H-pyrazolo[3,4-d]-pyrimidin-4-ylamine,
1-quinoxalin-2-yl-1H-pyrazolo[3,4-d]pyrimidin-4-ylamine,
1-benzothiazol-2-yl-1H-prazolo[3,4-d]pyrimidin-4-ylamine,
1-pyridin-4-yl-1H-pyrazolo[3,4-d]pyrimidin-4-ylamine,
1-(3,5-dimethyl-1H-pyrazol-4-yl)-1H-pyrazolo[3,4-d]pyrimidin-4-ylamine,
1-(4-methyl-oxazol-2-yl)-1H-pyrazolo[3,4-d]pyrimidin-4-ylamine,
1-thiazol-2-yl-1H-pyrazolo[3,4-d]pyrimidin-4-ylamine,
1-(4-methyl-thiazol-2-yl)-1H-pyrazolo[3,4-d]pyrimidin-4-ylamine,
1-(4-tert-butyl-thiazol-2-yl)-1H-pyrazolo[3,4-d]pyrimidin-4-yl-amine,
1-(4H-[1,2,4]triazol-3-yl)-1H-pyrazolo[3,4-d]pyrimidin-4-ylamine,
1-pyridin-3-yl-1H-pyrazolo[3,4-d]pyrimidin-4-ylamine,
1-pyrimidin-5-yl-1H-pyrazolo[3,4-d]pyrimidin-4-ylamine,
1-pyrimidin-2-yl-1H-pyrazolo[3,4-d]pyrimidin-4-ylamine,
1-pyrimidin-4-yl-1H-pyrazolo[3,4-d]pyrimidin-4-ylamine,
2-(4-amino-pyrazolo[3,4-d]pyrimidin-1-yl)-thiazole-4-carboxylic acid,
2-(4-amino-pyrazolo[3,4-d]pyrimidin-1-yl)-thiazole-4-carboxylic acid methyl ester.

13. The method of claim 1, wherein the compound is selected from

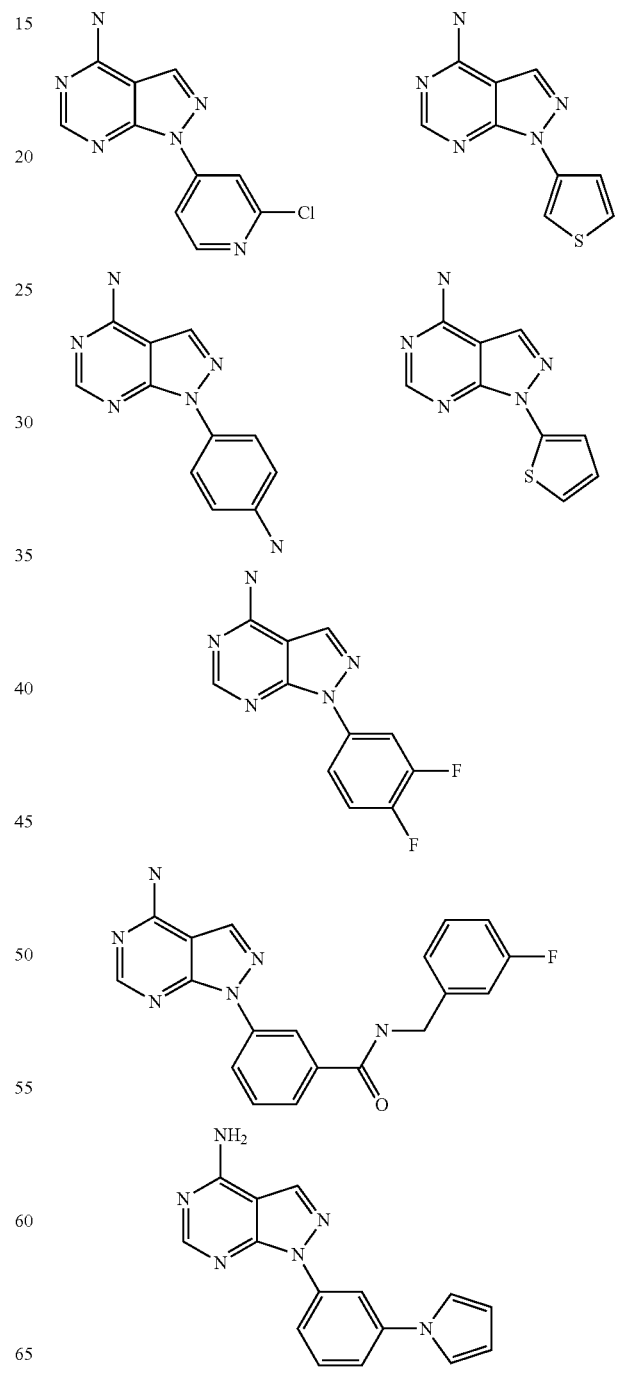

111
-continued
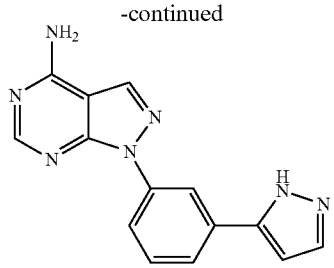
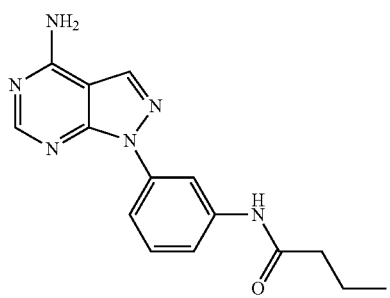
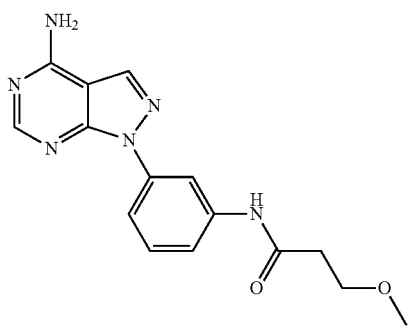
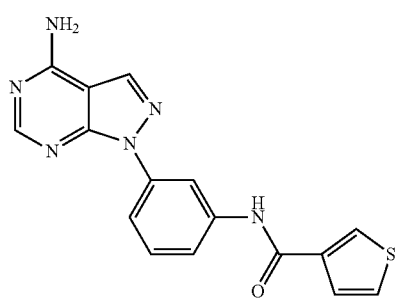
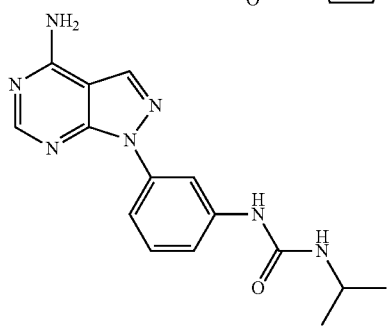
112
-continued
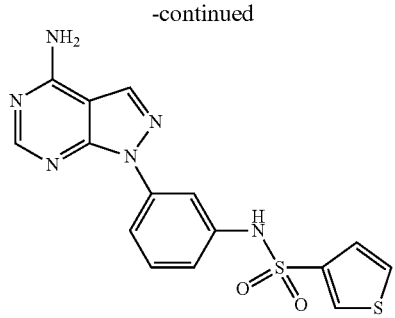
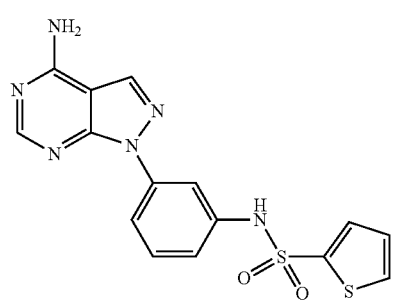
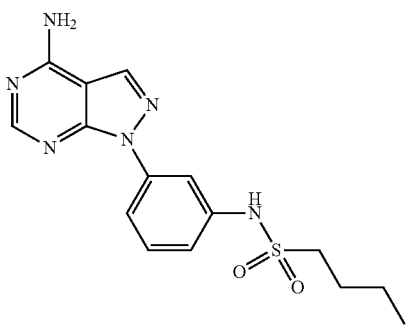
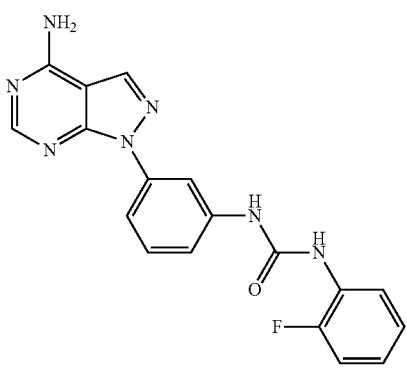
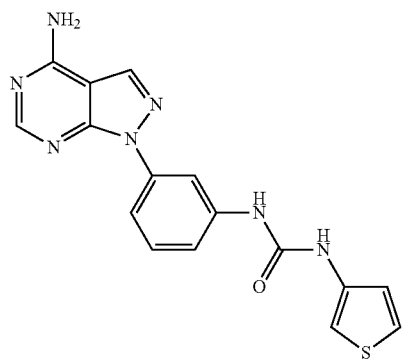

113
-continued
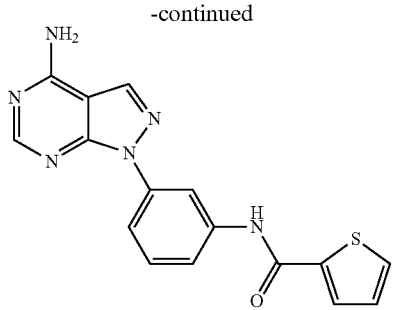
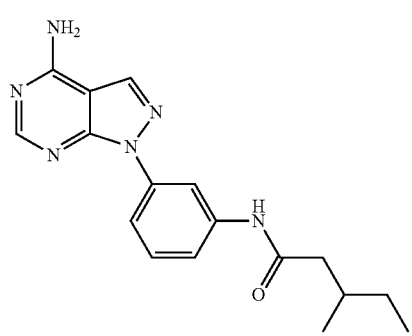
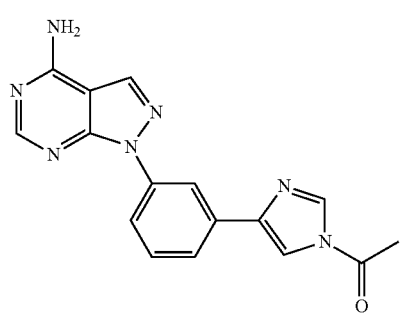
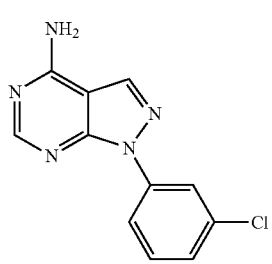
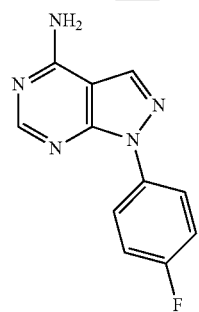
114
-continued
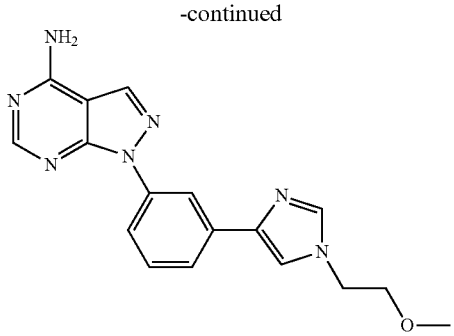
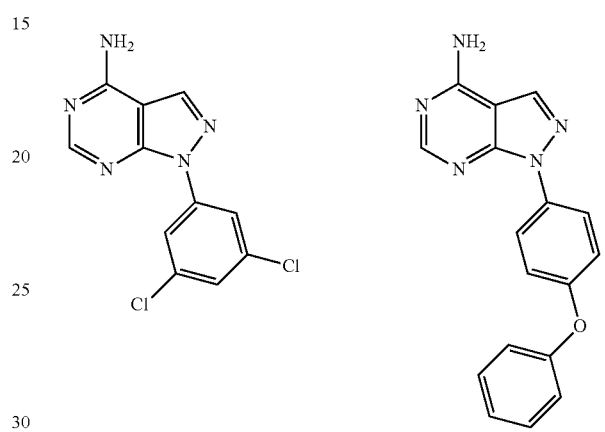

115
-continued
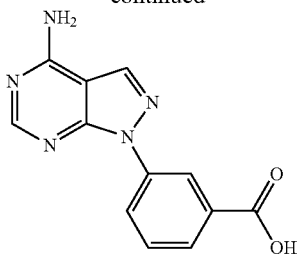
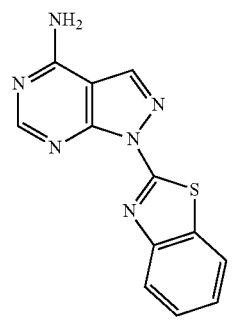
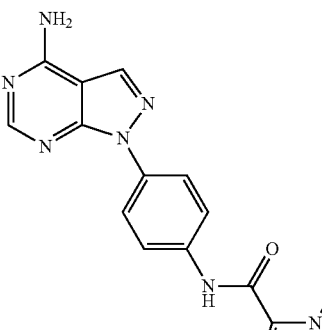
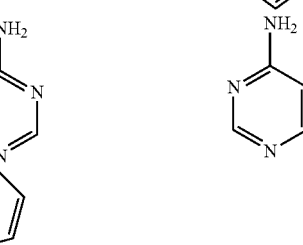
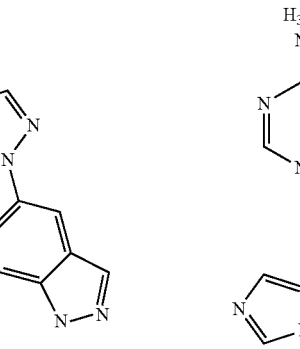
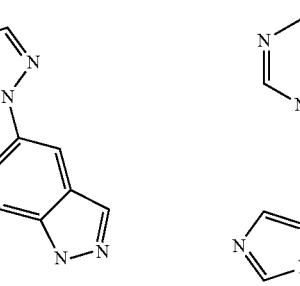
116
-continued
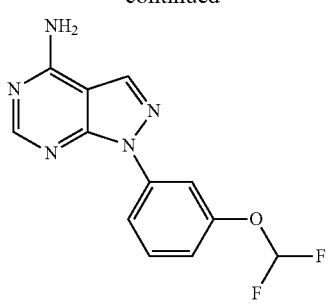
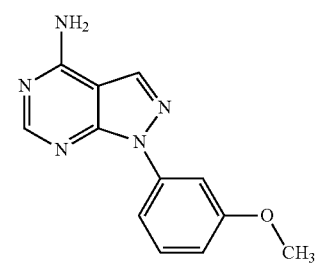
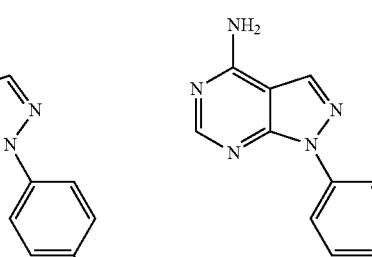
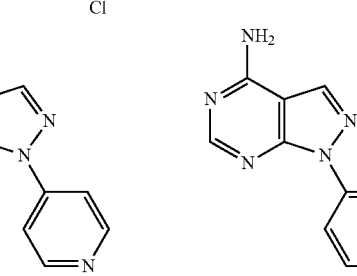
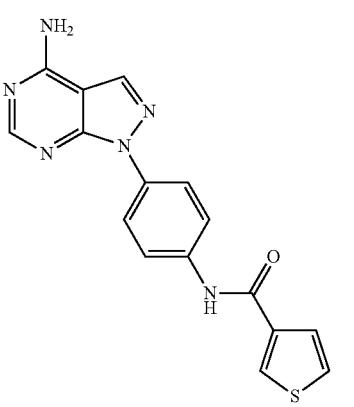

-continued
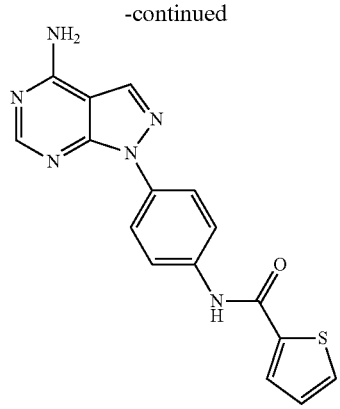
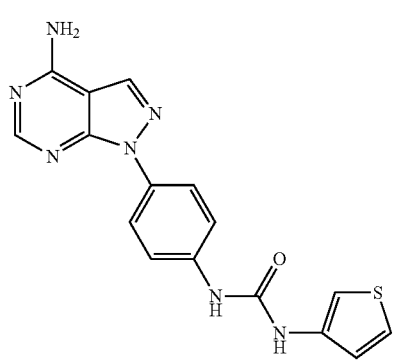
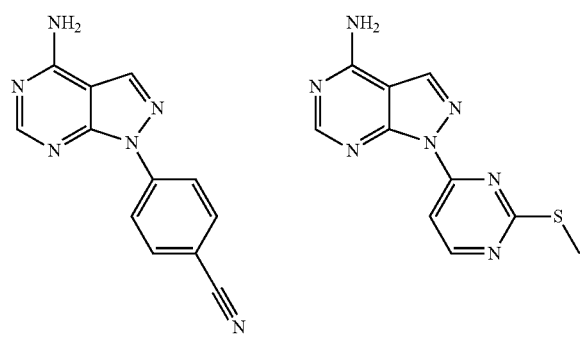
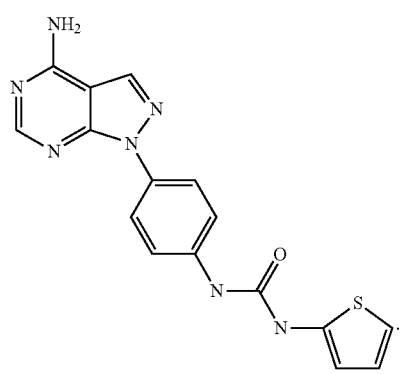
14. The method of claim 1, wherein the compound is selected from
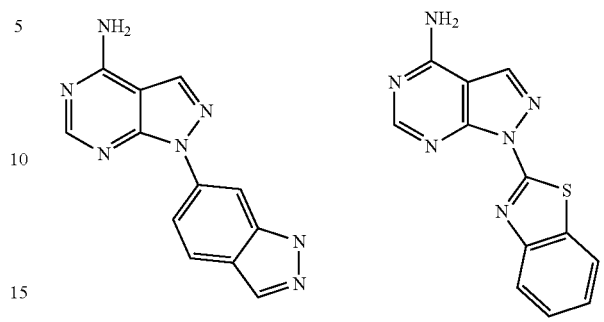
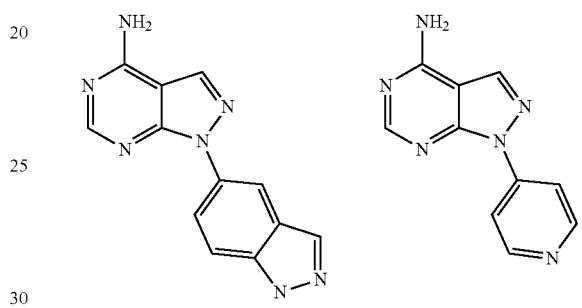
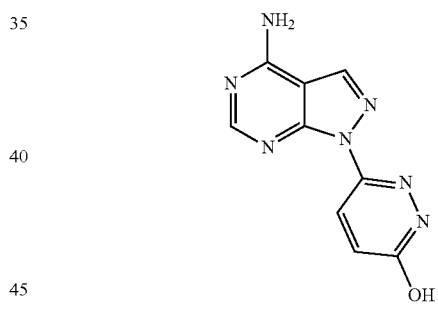
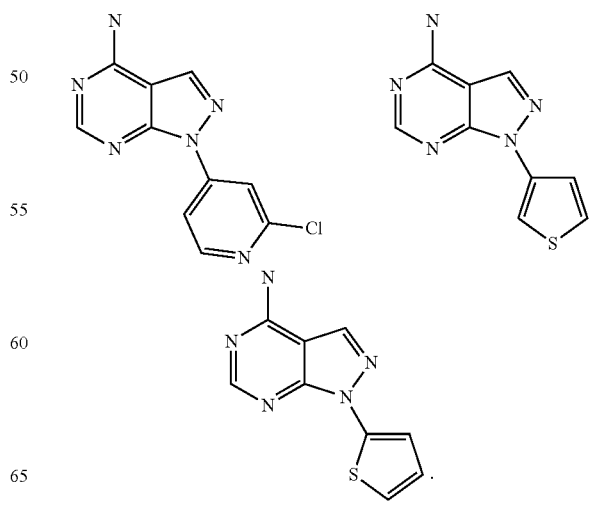

15. The method of claim 1, wherein the compound is selected from
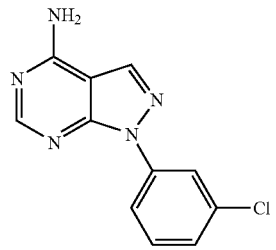
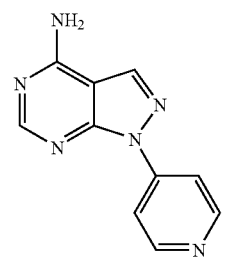
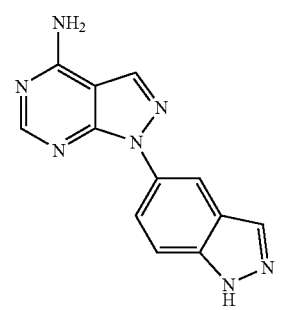
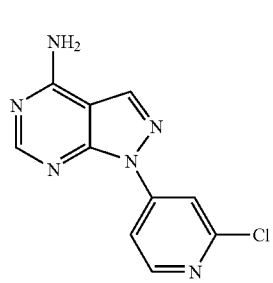
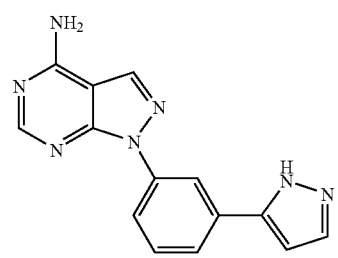
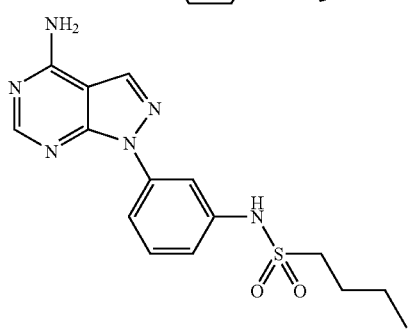
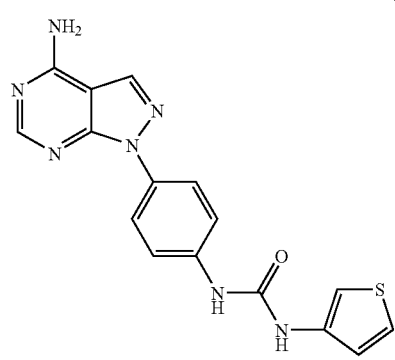
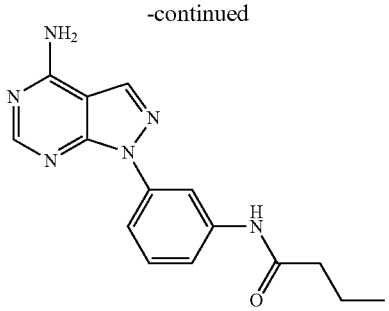
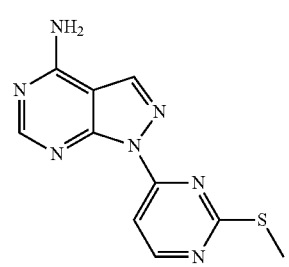
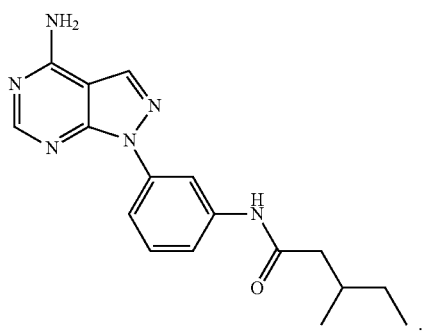
16. The method of claim 1, wherein the compound is selected from
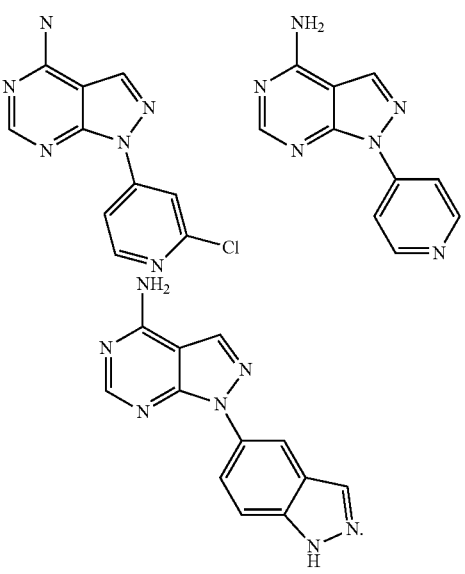

17. The method of claim 1, wherein the pharmaceutical composition is for oral, parenteral, local or topical administration.

18. The method of claim 1, wherein the subject is treated for diabetes mellitus type II.

19. The method of claim 1, wherein the subject is treated for obesity.

* * * * *